US009592392B2

(12) United States Patent
Demmer et al.

(10) Patent No.: US 9,592,392 B2
(45) Date of Patent: Mar. 14, 2017

(54) SENSING AND ATRIAL-SYNCHRONIZED VENTRICULAR PACING IN AN INTRACARDIAC PACEMAKER

(71) Applicant: Medtronic, Inc., Minneapolis, MN (US)

(72) Inventors: Wade M Demmer, Coon Rapids, MN (US); Todd J Sheldon, North Oaks, MN (US); Margaret G Guo, Cambridge, MA (US)

(73) Assignee: Medtronic, Inc., Minneapolis, MN (US)

( * ) Notice: Subject to any disclaimer, the term of this patent is extended or adjusted under 35 U.S.C. 154(b) by 21 days.

(21) Appl. No.: 14/821,141

(22) Filed: Aug. 7, 2015

(65) Prior Publication Data

US 2016/0114168 A1 Apr. 28, 2016

Related U.S. Application Data

(60) Provisional application No. 62/068,363, filed on Oct. 24, 2014.

(51) Int. Cl.
| | |
|---|---|
| A61N 1/36 | (2006.01) |
| A61N 1/365 | (2006.01) |
| A61N 1/37 | (2006.01) |
| A61B 5/04 | (2006.01) |

(52) U.S. Cl.
CPC ...... *A61N 1/36592* (2013.01); *A61B 5/04017* (2013.01); *A61N 1/3704* (2013.01)

(58) Field of Classification Search
CPC .. A61N 1/368; A61N 1/36514; A61N 1/3702; A61B 5/04012; A61B 5/04052

USPC .......................................................... 600/510
See application file for complete search history.

(56) References Cited

U.S. PATENT DOCUMENTS

| | | | |
|---|---|---|---|
| 4,411,271 | A | 10/1983 | Markowitz |
| 5,312,445 | A | 5/1994 | Nappholz et al. |
| 5,507,782 | A | 4/1996 | Kieval et al. |
| 5,593,431 | A | 1/1997 | Sheldon |
| 5,683,425 | A | 11/1997 | Hauptmann |
| 5,683,432 | A | 11/1997 | Goedeke et al. |
| 5,709,215 | A | 1/1998 | Perttu et al. |

(Continued)

FOREIGN PATENT DOCUMENTS

DE 4444144 A1 6/1996

OTHER PUBLICATIONS (PCT/US2015/055845) PCT Notification of Transmittal of the International Search Report and the Written Opinion of the International Searching Authority, mailed Mar. 30, 2016, 11 pages.

(Continued)

*Primary Examiner* — Paula J Stice

(57) ABSTRACT

A pacemaker implantable in a chamber of a patient's heart is configured to produce a filtered cardiac electrical signal by filtering a raw cardiac signal by an adjustable filter of a sensing module of the pacemaker. The sensing module is configured to receive the raw cardiac electrical signal comprising R-waves, T-waves and P-waves via electrodes coupled to the sensing module. The pacemaker is further configured to determine if the T-waves are distinct from the P-waves in the filtered cardiac electrical signal and adjust the filter to increase a difference between a feature of the P-waves and a feature of the T-waves in the filtered cardiac signal when the T-waves are not distinct from the P-waves.

22 Claims, 17 Drawing Sheets

(56) References Cited

U.S. PATENT DOCUMENTS

| | | |
|---|---|---|
| 5,755,739 A | 5/1998 | Sun et al. |
| 5,778,881 A | 7/1998 | Sun et al. |
| 6,377,844 B1 | 4/2002 | Graen |
| 6,418,346 B1 | 7/2002 | Nelson et al. |
| 6,442,433 B1 | 8/2002 | Linberg |
| 6,480,745 B2 | 11/2002 | Nelson et al. |
| 6,599,250 B2 | 7/2003 | Webb et al. |
| 6,625,490 B1 | 9/2003 | McClure et al. |
| 6,711,438 B1 | 3/2004 | McClure et al. |
| 7,024,243 B1 | 4/2006 | Bornzin et al. |
| 7,031,772 B2 | 4/2006 | Condie et al. |
| 7,047,073 B2 | 5/2006 | Hoijer et al. |
| 8,032,219 B2 | 10/2011 | Neumann et al. |
| 8,433,409 B2 | 4/2013 | Johnson et al. |
| 8,532,785 B1 | 9/2013 | Crutchfield et al. |
| 8,541,131 B2 | 9/2013 | Lund et al. |
| 8,600,490 B1 | 12/2013 | Bharmi et al. |
| 2004/0049120 A1 | 3/2004 | Cao et al. |
| 2009/0281587 A1 | 11/2009 | Pei |
| 2012/0172892 A1 | 7/2012 | Grubac et al. |
| 2013/0035748 A1 | 2/2013 | Bonner et al. |
| 2013/0116738 A1 | 5/2013 | Samade et al. |
| 2013/0123872 A1 | 5/2013 | Bornzin et al. |
| 2013/0138006 A1 | 5/2013 | Bornzin et al. |
| 2013/0325081 A1 | 12/2013 | Karst et al. |
| 2014/0121720 A1 | 5/2014 | Bonner et al. |

OTHER PUBLICATIONS (PCT/US2015/055846) PCT Notification of Transmittal of the International Search Report and the Written Opinion of the International Searching Authority, mailed Feb. 10, 2016, 9 pages.

(PCT/US2015/055854) PCT Notification of Transmittal of the International Search Report and the Written Opinion of the International Searching Authority, mailed Feb. 10, 2016, 9 pages.

U.S. Appl. No. 14/832,047, Notice of Allowance mailed Jun. 22, 2016.

SENSING AND ATRIAL-SYNCHRONIZED VENTRICULAR PACING IN AN INTRACARDIAC PACEMAKER

CROSS REFERENCE TO RELATED APPLICATIONS

This application claims the benefit of U.S. Provisional Application No.:62/068,363, filed on Oct. 24, 2014. The disclosure of the above application is incorporated herein by reference in its entirety.

The present application is commonly-assigned U.S. patent application Ser. No. 14/821,141 which is entitled SENSING AND ATRIAL-SYNCHRONIZED VENTRICULAR PACING IN AN INTRACARDIAC PACEMAKER; and U.S. Pat. No. 9,468,766, which is entitled SENSING AND ATRIAL-SYNCHRONIZED VENTRICULAR PACING IN AN INTRACARDIAC PACEMAKER, both of which are filed concurrently herewith and all of which are incorporated herein 15 by reference in their entireties.

TECHNICAL FIELD

The disclosure relates to an implantable medical device system and associated method for sensing cardiac events by an intracardiac pacemaker configured to deliver atrial-synchronized ventricular pacing.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one medical lead for positioning electrodes in one heart chamber, atrial or ventricular, or a dual chamber pacemaker coupled to two leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some patient conditions, other conditions may require atrial and ventricular (dual chamber) sensing for providing atrial-synchronized ventricular pacing and/or atrial and ventricular (dual chamber) pacing in order to maintain a regular heart rhythm.

SUMMARY

In general, the disclosure is directed to an intracardiac pacemaker capable of dual chamber sensing for providing atrial-synchronized ventricular pacing therapy to a patient. A pacemaker operating according to the techniques disclosed herein filters a raw cardiac signal including P-waves, T-waves and R-waves to increase a difference between the P-waves and the T-waves and R-waves in time, waveform morphology and/or amplitude to support reliable P-wave sensing. In various examples, P-wave sensing by an intracardiac pacemaker enables atrial-synchronized ventricular pacing to be delivered.

In one example, the disclosure provides a method including producing a filtered cardiac electrical signal by an adjustable filter of a sensing module of a medical device configured to receive a raw cardiac electrical signal comprising R-waves, T-waves and P-waves via electrodes coupled to the sensing module, determining if the T-waves are distinct from the P-waves in the filtered cardiac electrical signal, adjusting the filter to increase a difference between a feature of the P-waves and a feature of the T-waves in the filtered cardiac signal when the T-waves are not distinct from the P-waves, determining P-wave sensing criteria based on the difference, sensing a P-wave from the filtered cardiac electrical signal when the P-wave sensing criteria are met, and setting a ventricular pacing escape interval in response to sensing the P-wave.

In another example, the disclosure provides an implantable medical device including a sensing module, a pulse generator and a control module coupled to the sensing module and the pulse generator. The sensing module includes an adjustable filter and is configured to receive a raw cardiac electrical signal comprising R-waves, T-waves and P-waves via electrodes coupled to the sensing module, filter the raw cardiac electrical signal by the adjustable filter to produce a filtered cardiac electrical signal, determine if the T-waves are distinct from the P-waves in the filtered cardiac electrical signal, adjust the filter to increase a difference between a feature of the P-waves and a feature of the T-waves in the filtered cardiac signal when the T-waves are not distinct from the P-waves, determine P-wave sensing criteria based on the difference; and sense a P-wave from the filtered cardiac electrical signal when the P-wave sensing criteria are met. The pulse generator is configured to generate and deliver a ventricular pacing pulse via electrodes coupled to the pulse generator. The control module is configured to set a ventricular pacing escape interval in response to the sensing module sensing the P-wave to control the pulse generator to deliver a ventricular pacing pulse when the ventricular pacing escape interval expires.

In yet another example, the disclosure provides a non-transitory, computer-readable medium storing a set of instructions which, when executed by an implantable medical device cause the device to produce a filtered cardiac electrical signal by an adjustable filter of a sensing module of the medical device configured to receive a raw cardiac electrical signal comprising R-waves, T-waves and P-waves via electrodes coupled to the sensing module, determine if the T-waves are distinct from the P-waves in the filtered cardiac electrical signal, adjust the filter to increase a difference between a feature of the P-waves and a feature of the T-waves in the filtered cardiac signal when the T-waves are not distinct from the P-waves, determine P-wave sensing criteria based on the difference, sense a P-wave from the filtered cardiac electrical signal when the P-wave sensing criteria are met, and set a ventricular pacing escape interval in response to sensing the P-wave.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
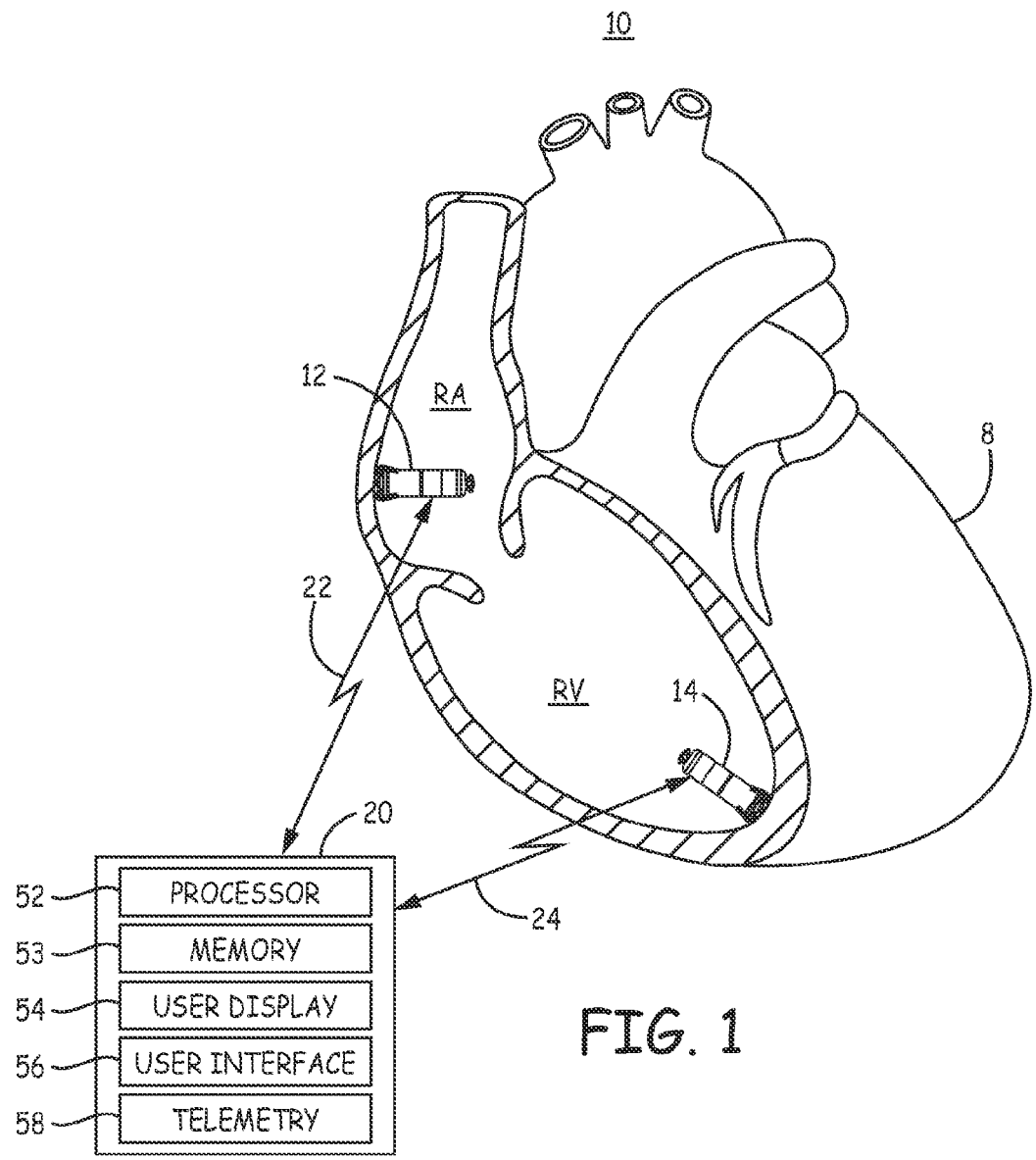
FIG. 1 is a conceptual diagram illustrating an intracardiac pacing system that may be used to sense cardiac electrical signals and provide therapy to a patient's heart.

An implantable medical device (IMD) system is disclosed herein that includes a ventricular intracardiac pacemaker configured to be implanted wholly in a ventricular chamber of the patient's heart. In various examples, the IMD system may include an atrial intracardiac pacemaker and a ventricular intracardiac pacemaker that do not require transvenous leads but are enabled to provide coordinated atrial and ventricular pacing without wireless or wired communication signals between the two intracardiac pacemakers. The ventricular intracardiac pacemaker establishes P-wave sensing criteria for reliably distinguishing P-waves from R-wave and T-waves to enable the ventricular pacemaker to deliver atrial-synchronized ventricular pacing.

A dual chamber pacemaker positioned in an implant pocket and coupled to transvenous atrial and ventricular leads may be programmed to deliver only atrial pacing (AAI(R)), only ventricular pacing (VVI(R)) or both (DDD (R)) according to patient need. The dual chamber pacemaker is able to control the delivery of pacing pulses in both atrial and ventricular chambers because the pacemaker will receive sensed event signals from both atrial and ventricular chambers and control when a pacing pulse is delivered in both chambers relative to the sensed events using the electrodes positioned in both chambers. In other words, the dual chamber pacemaker knows when both sensed and paced events have occurred in both atrial and ventricular sensing and pacing channels since all sensing and pacing control is happening in the one device, i.e., the dual chamber pacemaker.

Intracardiac pacemakers have been introduced that are adapted to be implanted wholly within a heart chamber. Elimination of transvenous, intracardiac leads has several advantages. For example, complications due to infection associated with a lead extending from a subcutaneous pacemaker pocket transvenously into the heart can be eliminated. Other complications such as "twiddler's syndrome", lead fracture or poor connection of the lead to the pacemaker are eliminated in the use of an intracardiac pacemaker.

An intracardiac pacemaker may operate in a single chamber pacing and sensing mode, e.g., AAI or VVI, by delivering pacing pulses and inhibiting pacing when an intrinsic event is sensed in the chamber that the pacemaker is implanted in. While some patients may require only single chamber pacing and sensing, patients having AV conduction defects may require a pacing system capable of delivering ventricular pacing pulses that are synchronized to atrial events, including atrial paced events (if an atrial pacemaker is present) and sensed intrinsic atrial events (i.e., P-waves attendant to the depolarization of the atria). When ventricular pacing pulses, are properly synchronized to atrial events, the ventricle is paced at a target atrioventricular (AV) interval following an atrial event. Maintaining a target AV interval is important in maintaining proper filling of the ventricles for promoting optimal hemodynamic function.

FIG. 1 is a conceptual diagram illustrating an intracardiac pacing system 10 that may be used to sense cardiac electrical signals and provide therapy to a patient's heart 8. IMD system 10 includes a right ventricular (RV) intracardiac pacemaker 14 and may optionally include a right atrial (RA) intracardiac pacemaker 12. Pacemakers 12 and 14 are transcatheter intracardiac pacemakers adapted for implantation wholly within a heart chamber, e.g., wholly within the RV, wholly within the left ventricle (LV), wholly within the RA or wholly within the left atrium (LA) of heart 8. In the example of FIG. 1, pacemaker 12 is positioned along an endocardial wall of the RA, e.g., along the RA lateral wall or RA septum. Pacemaker 14 is positioned along an endocardial wall of the RV, e.g., near the RV apex. The techniques disclosed herein, however, are not limited to the pacemaker locations shown in the example of FIG. 1 and other positions and relative locations from each other are possible. In some examples, a ventricular intracardiac pacemaker 14 is positioned in the LV for delivering atrial-synchronized ventricular pacing using the techniques disclosed herein.

Pacemakers 12 and 14 are reduced in size compared to subcutaneously implanted pacemakers and are generally cylindrical in shape to enable transvenous implantation via a delivery catheter. In other examples, pacemakers 12 and 14 may be positioned at any other location inside or outside heart 8, including epicardial locations. For example, pacemaker 12 may be positioned outside or within the right atrium or left atrium to provide respective right atrial or left atrial pacing. Pacemaker 14 may be positioned outside or within the right ventricle or left ventricle to provide respective right ventricular or left ventricular pacing.

Pacemakers 12 and 14 are each capable of producing electrical stimulation pulses, i.e., pacing pulses, delivered to heart 8 via one or more electrodes on the outer housing of the pacemaker. RA pacemaker 12 is configured to sense an intracardiac electrogram (EGM) signal in the RA using the housing based electrodes and deliver RA pacing pulses. RV pacemaker 14 is configured to sense an EGM signal in the RV using housing based electrodes and deliver RV pacing pulses.

In some examples, a patient may only require RV pacemaker 14 for delivering atrial-synchronized ventricular pacing, e.g., in the case of atrio-ventricular (AV) block. In other examples, depending on individual patient need, RA pacemaker 12 may be implanted first, and RV pacemaker 14 may be implanted at a later time after the patient develops a need for ventricular pacing, e.g., if the patient develops AV conduction defects. In other examples, the patient may receive the RV pacemaker 14 first and later receive RA pacemaker 12, or the patient may receive both RA pacemaker 12 and RV pacemaker 14 during the same implant procedure.

The RV pacemaker 14 is configured to control the delivery of ventricular pacing pulses to the RV in a manner that promotes maintaining a target AV interval between atrial and ventricular events, e.g., between P-waves (intrinsic or pacing-evoked) and ventricular pacing pulses or the resulting pacing-evoked R-waves. A target AV interval may be a programmed value selected by a clinician. A target AV interval may be identified as being hemodynamically optimal for a given patient based on clinical testing or assessments of the patient or based on clinical data from a population of patients. Each of the RA pacemaker 12 and RV pacemaker 14 include a control module that controls functions performed by the respective pacemaker. According to the techniques disclosed herein, the control module of the RV pacemaker 14 is configured to automatically adjust P-wave sensing criteria and dynamically adjust a ventricular pacing escape interval based on EGM signal analysis performed to discriminate P-waves from R-waves and T-waves.

Pacemakers 12 and 14 may each be capable of bidirectional wireless communication with an external device 20. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemakers 12 and 14. External device 20 may be located in a clinic, hospital or other medical facility. External device 20 may alternatively be embodied as a home monitor or a handheld device that may be used in a medical facility, in the patient's home, or another location. Operating parameters, such as sensing and therapy delivery control parameters, may be programmed into pacemakers 12 and 14 using external device 20.

External device 20 includes a processor 52 and associated memory 53, user display 54, user interface 56 and telemetry module 58. Processor 52 controls external device operations and processes data and signals received from pacemakers 12 and 14. According to techniques disclosed herein, processor 52 receives EGM and marker channel data transmitted to telemetry module 58 from RV pacemaker 14. Processor 52 provides user display 54 with the EGM and marker channel data for display to a user.

The user display 54 produces a display of EGM signal data, which may be delayed from real time as described below in conjunction with FIGS. 11A and 11B, and marker channel markers based on data received from RV pacemaker 14. The display may be a part of a graphical user interface that facilitates programming of sensing control parameters by a user interacting with external device 20. External device 20 may display other data and information relating to pacemaker functions to a user for reviewing pacemaker operation and programmed parameters as well as EGM signals or other physiological data that is retrieved from pacemakers 12 and 14 during an interrogation session. User interface 56 may include a mouse, touch screen, keyboard and/or keypad to enable a user to interact with external device 20 to initiate a telemetry session with pacemakers 12 and/or 14 for retrieving data from and/or transmitting data to pacemakers 12 and/or 14 for selecting and programming desired sensing and therapy delivery control parameters.

Telemetry module 58 is configured for bidirectional communication with implantable telemetry modules included in each of pacemakers 12 and 14. External device 20 establishes a wireless radio frequency (RF) communication link 22 with RA pacemaker 12 and wireless RF communication link 24 with RV pacemaker 14 using a communication protocol that appropriately addresses the targeted pacemaker 12 or 14. An example RF telemetry communication system that may be implemented in system 10 is generally disclosed in U.S. Pat. No. 5,683,432 (Goedeke, et al.), hereby incorporated herein by reference in its entirety.

Telemetry module 58 is configured to operate in conjunction with processor 52 for sending and receiving data relating to pacemaker functions via communication link 22 or 24. Communication links 22 and 24 may be established between respective RA pacemaker 12 and RV pacemaker 14 and external device 20 using an RF link such as BLUETOOTH®, Wi-Fi, Medical Implant Communication Service (MICS) or other RF bandwidth. In some examples, external device 20 may include a programming head that is placed proximate pacemaker 12 or 14 to establish and maintain a communication link, and in other examples external device 20 and pacemakers 12 and 14 may be configured to communicate using a distance telemetry algorithm and circuitry that does not require the use of a programming head and does not require user intervention to maintain a communication link.

It is contemplated that external device 20 may be in wired or wireless connection to a communications network via telemetry module 58 for transferring data to a remote database or computer to allow remote management of the patient 12. Remote patient management systems may be configured to utilize the presently disclosed techniques to enable a clinician to review EGM and marker channel data and authorize programming of sensing control parameters after viewing a visual representation of EGM and marker channel data. Reference is made to commonly-assigned U.S. Pat. No. 6,599,250 (Webb et al.), U.S. Pat. No. 6,442,433 (Linberg, et al.), U.S. Pat. No. 6,418,346 (Nelson, et al.), and U.S. Pat. No. 6,480,745 (Nelson, et al.) for general descriptions and examples of remote patient management systems that enable remote patient monitoring and device programming. Each of these patents is incorporated herein by reference in their entirety.

For example, neither RA pacemaker 12 nor RV pacemaker 14 may be configured to initiate an RF communication session with the other device. Both pacemakers 12 and 14 may be configured to periodically "listen" for a valid "wake up" telemetry signal from external device 20 and power up its own telemetry module to establish a communication link 22 or 24 in response to a valid telemetry signal (or go back to "sleep" if no valid telemetry signal is received). However, pacemaker 12 and pacemaker 14 may or may not be configured to communicate directly with each other. In some cases, pacemakers 12 and 14 may be configured to communicate with each other, but, in order to conserve battery life of the intracardiac pacemakers 12 and 14, communication may be minimized. As such, communication does not occur on a beat-by-beat basis between the RA pacemaker 12 and RV pacemaker 14 for communicating when the other pacemaker is sensing cardiac events or when it is delivering pacing pulses. RV pacemaker 14, however, is configured to sense atrial events and automatically adjust P-wave sensing criteria for reliably discriminating P-waves from R-waves and T-waves of an intracardiac ventricular EGM signal, without requiring communication signals from RA pacemaker 12.

Figure 2A:
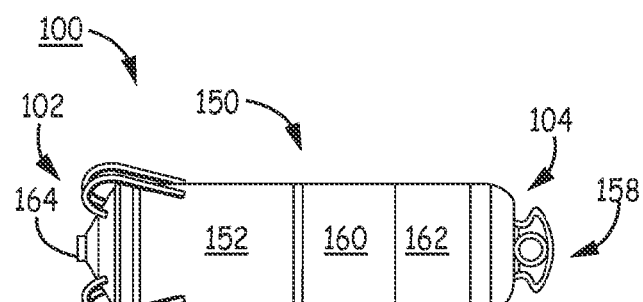
FIG. 2A is a conceptual diagram of an intracardiac pacemaker.

FIG. 2A is a conceptual diagram of an intracardiac pacemaker 100 that may correspond to RA pacemaker 12 or RV pacemaker 14 shown in FIG. 1. Pacemaker 100 includes electrodes 162 and 164 spaced apart along the housing 150 of pacemaker 100 for sensing cardiac EGM signals and delivering pacing pulses. Electrode 164 is shown as a tip electrode extending from a distal end 102 of pacemaker 100, and electrode 162 is shown as a ring electrode along a mid-portion of housing 150, for example adjacent proximal end 104. Distal end 102 is referred to as "distal" in that it is expected to be the leading end as it advanced through a delivery tool, such as a catheter, and placed against a target pacing site.

Electrodes 162 and 164 form an anode and cathode pair for bipolar cardiac pacing and sensing. Electrodes 162 and 164 may be positioned on or as near as possible to respective proximal and distal ends 104 and 102 to increase the inter-electrode spacing between electrodes 162 and 164. Relatively greater inter-electrode spacing will increase the likelihood of sensing far-field (FF) signals occurring in a different heart chamber than the chamber in which pacemaker 100 is implanted. For example, an increased inter-electrode spacing between electrodes 162 and 164 when pacemaker 100 is used as an RV pacemaker may improve reliable sensing of FF atrial events by pacemaker 100 for use in controlling the timing of ventricular pacing pulses.

In alternative embodiments, pacemaker 100 may include two or more ring electrodes, two tip electrodes, and/or other types of electrodes exposed along pacemaker housing 150 for delivering electrical stimulation to heart 8 and sensing EGM signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 100 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as an electrode instead of providing a localized electrode such as electrode 162. Alternatively, electrode 162 may be electrically isolated from the other portions of the housing 150. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 100. Tip electrode 164 may be coupled via a feedthrough to circuitry within control electronics subassembly 152, e.g., a pacing pulse generator and sensing module, to serve as the pacing cathode electrode.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to patient tissue, e.g., by actively engaging with the ventricular endocardium and/or interacting with the ventricular trabeculae. Fixation tines 166 are configured to anchor pacemaker 100 to position electrode 164 in operative proximity to a targeted tissue for delivering therapeutic electrical stimulation pulses. Numerous types of active and/or passive fixation members may be employed for anchoring or stabilizing pacemaker 100 in an implant position. Pacemaker 100 may include a set of fixation tines as disclosed in commonly-assigned, pre-grant publication U.S. 2012/0172892 (Grubac, et al.), hereby incorporated herein by reference in its entirety.

Pacemaker 100 may further include a delivery tool interface 158. Delivery tool interface 158 may be located at the proximal end 104 of pacemaker 100 and is configured to connect to a delivery device, such as a catheter, used to position pacemaker 100 at an implant location during an implantation procedure, for example within a heart chamber.

A reduced size of pacemaker 100 enables implantation wholly within a heart chamber. In FIG. 1, RA pacemaker 12 and RV pacemaker 14 may have different dimensions. For example, RA pacemaker 12 may be smaller in volume than pacemaker 14, e.g., by reducing battery size, to accommodate implantation in the smaller heart chamber. As such, it is recognized that pacemaker 100 may be adapted in size, shape, electrode location or other physical characteristics according to the heart chamber or location in which it will be implanted.

Figure 2B:
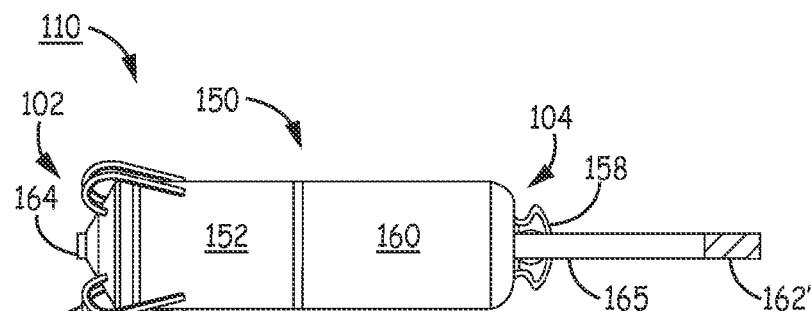
FIGS. 2B and 2C are conceptual diagrams of alternative embodiments of an intracardiac pacemaker.

FIG. 2B is a conceptual diagram of an alternative embodiment of an intracardiac pacemaker 110. Pacemaker 110 includes a housing 150, control electronics subassembly 152, battery subassembly 160, fixation member 166 and electrode 164 along a distal end 102, and may include a delivery tool interface 158 along the proximal end 104 as described above in conjunction with FIG. 2A. Pacemaker 110 is shown to include an electrode 162' extending away from housing 150 along an extender 165. As such, instead of carrying a pair of electrodes along the housing 150, which limits the maximum possible inter-electrode spacing, an extender 165 may be coupled to the housing 150 for positioning the anode electrode 162' at an increased inter-electrode distance from distal tip electrode 164. The increased distance may position a sensing electrode in or near the atrium for improved P-wave sensing. The techniques disclosed herein may be implemented in a pacemaker with a proximal sensing extension as generally disclosed in U.S. Pat. Application No. 62/025,690 , filed provisionally on Jul. 17, 2014, incorporated herein by reference in its entirety.

Figure 2C:
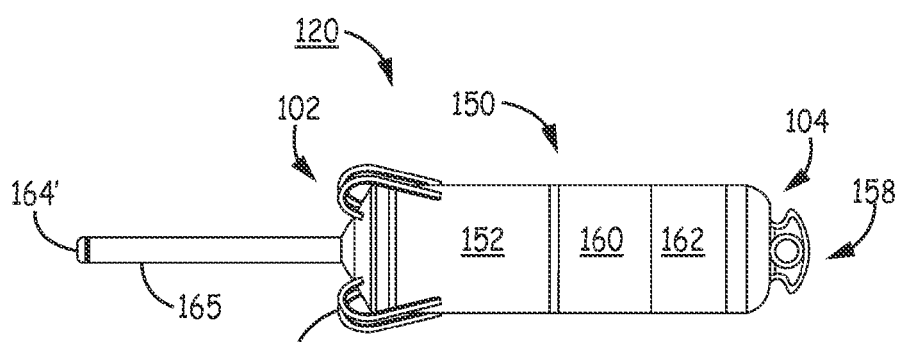

FIG. 2C is a conceptual diagram of an alternative embodiment of intracardiac pacemaker 120 having extender 165 coupled to the distal end 102 of pacemaker housing 150 to extend distal electrode 164' away from electrode 162 positioned along housing 150 near or at proximal end 104. Extender 165 is an insulated electrical conductor that may electrically couple electrode 164' to pacemaker circuitry via an electrical feedthrough crossing housing 150. Pacemaker 120 having an insulated, electrically conductive extender 165 for increasing the inter-electrode spacing may correspond generally to the implantable device and flexible conductor disclosed in commonly-assigned, pre-grant U.S. Publication No. 2013/0035748 (Bonner, et al.), hereby incorporated herein by reference in its entirety.

Figure 3:
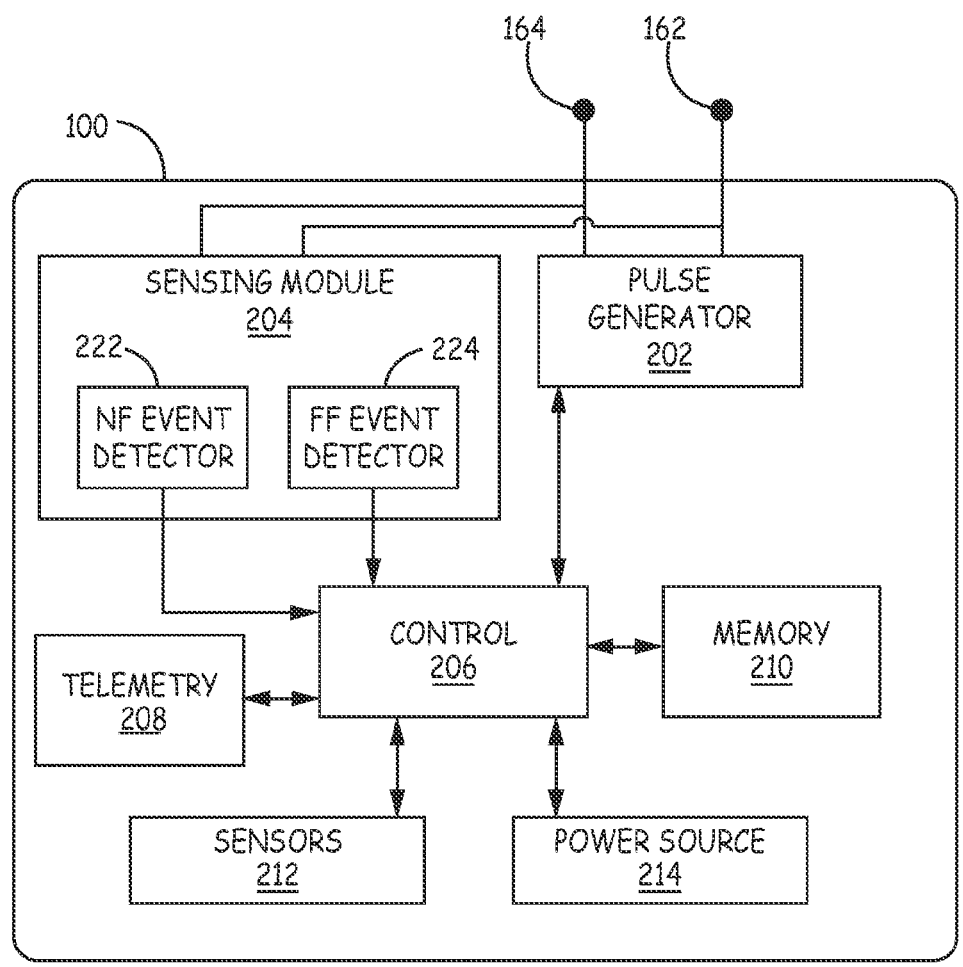
FIG. 3 is a functional block diagram of an example configuration of the intracardiac pacemaker shown in FIG. 2A.

FIG. 3 is a functional block diagram of an example configuration of pacemaker 100 shown in FIG. 2A. Pacemaker 100 includes a pulse generator 202, a sensing module 204, a control module 206, memory 210, telemetry module 208 and a power source 214. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. Each of RA pacemaker 12 and RV pacemaker 14 will include similar modules as represented by the pacemaker 100 shown in FIG. 3; however it is understood that the modules are configured differently as needed to perform the functionality of the separate RA and RV pacemakers 12 and 14.

When pacemaker 100 is configured to operate as RV pacemaker 14, control module 206 is configured to set various ventricular pacing escape intervals used to control delivery of ventricular pacing pulses as disclosed herein. When pacemaker 100 is embodied as RA pacemaker 12, control module 206 is configured to set atrial pacing escape intervals to control delivery of RA pacing pulses. Adaptations of the hardware, firmware or software of the various modules of pacemaker 100 necessary to meet the described functionality of the intracardiac pacemakers positioned in different heart chambers as disclosed herein is understood to be included in the various modules of pacemaker 100 according to the intended implant location.

The functions attributed to pacemaker 100 herein may be embodied as one or more processors, controllers, hardware, firmware, software, or any combination thereof. Depiction of different features as specific circuitry or modules is intended to highlight different functional aspects and does not necessarily imply that such functions must be realized by separate hardware or software components or by any particular architecture. Rather, functionality associated with one or more modules, processors, or circuits may be performed by separate hardware or software components, or integrated within common hardware or software components. For example, pacing control operations performed by pacemaker 100 may be implemented in control module 206 executing instructions stored in associated memory 210 and relying on input from sensing module 204.

The functional operation of pacemaker 100 as disclosed herein should not be construed as reflective of a specific form of software or hardware necessary to practice the methods described. It is believed that the particular form of software, hardware and/or firmware will be determined primarily by the particular system architecture employed in the pacemaker 100 and by the particular sensing and therapy delivery methodologies employed by the pacemaker 100. Providing software, hardware, and/or firmware to accomplish the described functionality in the context of any modern pacemaker system, given the disclosure herein, is within the abilities of one of skill in the art.

Pulse generator 202 generates electrical stimulation pulses that are delivered to heart tissue via electrodes 162 and 164. Electrodes 162 and 164 may be housing-based electrodes as shown in FIG. 2A, but one or both electrodes 162 and 164 may alternatively be carried by an insulated, electrical conductor extending away from the pacemaker housing as described in conjunction with FIGS. 2B and 2C.

Pulse generator 202 may include one or more capacitors and a charging circuit to charge the capacitor(s) to a programmed pacing pulse voltage. At appropriate times, as controlled by a pace timing and control module included in control module 206, the capacitor is coupled to pacing electrodes 162 and 164 to discharge the capacitor voltage and thereby deliver the pacing pulse. Pacing circuitry generally disclosed in the above-incorporated U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 100 for charging a pacing capacitor to a predetermined pacing pulse amplitude under the control of control module 206 and delivering a pacing pulse.

Control module 206 controls pulse generator 202 to deliver a pacing pulse in response to expiration of a pacing escape interval according to programmed therapy control parameters stored in memory 210. The pace timing and control module included in control module 206 includes an escape interval timer that is set to various pacing escape intervals used for controlling the timing of pacing pulses relative to a paced or sensed event. Upon expiration of a pacing escape interval, a pacing pulse is delivered. If a cardiac event is sensed during the pacing escape interval by sensing module 204, the scheduled pacing pulse may be inhibited, and the pacing escape interval may be reset to a new time interval. Control of pacing escape intervals by control module 206 is described below in conjunction with the various flow charts presented herein.

Sensing module 204 includes cardiac event detectors 222 and 224 for receiving cardiac EGM signals developed across electrodes 162 and 164. A cardiac event may be sensed by sensing module 204 when the EGM signal crosses a sensing threshold of a cardiac event detector 222 or 224. The sensing threshold may be an auto-adjusting sensing threshold that may be initially set based on the amplitude of a sensed event and decays at a predetermined decay rate thereafter. In response to a sensing threshold crossing, sensing module 204 passes a sensed event signal to control module 206.

Sensing module 204 may include a near-field (NF) event detector 222 and a far-field (FF) event detector 224. NF cardiac events are events that occur in the heart chamber where the electrodes 162 and 164 are located. FF cardiac events are events that occur in a different heart chamber than the heart chamber where electrodes 162 and 164 are located.

The NF cardiac event detector 222 of RV pacemaker 12 may be programmed with a sensing threshold appropriate for sensing R-waves attendant to the depolarization of the ventricles. NF cardiac event detector 222 of RV pacemaker 100 produces a NF sensed event signal, also referred to herein as an "R-sense signal," provided to control module 206 in response to detecting an R-wave sensing threshold crossing The terms "sensed cardiac events" or "sensed events" as used herein refer to events sensed by sensing module 204 in response to the EGM signal crossing a sensing threshold, which may be an amplitude threshold, a frequency threshold, a slew rate threshold, or any combination thereof. Sensed cardiac events may include intrinsic events and evoked events caused by a delivered pacing pulse. Intrinsic events are events arising in the heart in the absence of a pacing pulse. Intrinsic events include intrinsic P-waves, such as sinus P-waves originating from the sino-atrial node of the heart, and intrinsic R-waves, such as sinus R-waves conducted through the heart's normal conduction pathway to the ventricles from the atria via the atrioventricular node. Intrinsic events can also include non-sinus intrinsic events, such as premature atrial contractions (PACs) or premature ventricular contractions (PVCs) that arise intrinsically from the heart but are ectopic in origin.

FF event detector 224 may be configured to sense FF atrial events when pacemaker 100 is embodied as RV pacemaker 14. A FF atrial event sensing threshold may be used by FF event detector 224 for sensing FF atrial events. The FF atrial event sensing threshold is different than the sensing threshold used by NF event detector 222 but is applied to the same EGM signal developed across electrodes 162 and 164 to enable sensing module 204 to distinctly sense FF atrial events and NF R-waves. FF event detector 224 produces a FF sensed event signal, also referred to herein as a "P-sense signal," passed to control module 206 in response to sensing a FF atrial event. FF atrial events sensed by FF event detector 224 may include atrial pacing pulses delivered by RA pacemaker 12 and/or P-waves, intrinsic or evoked. The FF event detector 224 may or may not be configured to discriminate between sensed FF atrial events that are pacing pulses and sensed FF atrial events that are P-waves. The atrial events sensed by RV pacemaker 14 are referred to as "far-field" events because they are events occurring in a heart chamber different than the RV, where pacemaker 14 is implanted. It is recognized that when a proximal sensing extension is used as show in FIG. 2B, at least one electrode may be positioned proximate the atrium so that the signal itself may approach near-field atrial signal sensing.

FF P-waves are relatively small amplitude signals compared to NF R-waves and may be similar in amplitude to NF T-waves, associated with the repolarization of the ventricular myocardium. P-waves may be challenging to distinguish from T-waves and baseline noise on the ventricular EGM signal. The inter-electrode spacing of sensing electrodes 162 and 164 may be increased to enhance sensing of small amplitude FF P-waves by FF event detector 224. As described in conjunction with the flow charts disclosed herein, RV pacemaker 14 is configured to establish P-wave sensing criteria to reliably sense FF P-waves from the ventricular EGM signal received by sensing module 204 via electrodes 162 and 164.

FF P-waves may be distinguishable from NF R-waves and T-waves based on amplitude, timing, frequency content, slope, the shape of the overall P-wave morphology or specific features of the P-wave morphology. An R-wave sensing threshold used by NF event detector 222 in RV pacemaker 14 may be set greater than an expected FF P-wave amplitude so that R-waves are sensed when the EGM signal developed across electrodes 162 and 164 crosses the R-wave sensing threshold. FF P-waves may be sensed by FF event detector 224 of the RV pacemaker 14 using a different sensing threshold that is lower than the NF R-wave sensing threshold.

When available, P-sense signals produced by FF event detector 224 in RV pacemaker 14 may be used by control module 206 of RV pacemaker 14 to deliver atrial-synchronized ventricular pacing. FF atrial events, however, may be absent or undersensed by RV pacemaker 14, e.g., due to changes in position of the electrodes 162 and 164 or other conditions that alter the P-wave morphology. In some cases, the T-wave and the P-wave may become indistinguishable. Using the techniques disclosed herein, RV pacemaker 14 is configured to adjust P-wave sensing criteria used by FF event detector 224 to improve the reliability of P-wave sensing over time and control ventricular pacing in a manner that maintains a target AV interval when reliable P-sense signals are produced by FF event detector 224 and switch to a VVI or VVIR pacing mode when reliable P-sense signals are not available.

Memory 210 may include computer-readable instructions that, when executed by control module 206 and/or sensing module 204, cause control module 206 and/or sensing module 204 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores timing intervals, counters, or other data used by control module 206 to control the delivery of pacing pulses by pulse generator 202, e.g., by setting a pacing escape interval timer included in control module 206, according to the techniques disclosed herein.

Pacemaker 100 may further include one or more physiological sensors 212 used for monitoring the patient. Sensors 212 may include a pressure sensor, an acoustical sensor, an oxygen sensor, or any other sensor used to monitor a patient. In some examples, physiological sensors 212 include at least one physiological sensor producing a signal indicative of the metabolic demand of the patient. The signal indicative of the patient's metabolic demand is used by control module 206 for determining a sensor indicated pacing rate used to control the heart rate to meet the patient's metabolic demand.

For example, sensors 212 may include an accelerometer for producing a patient activity signal passed to control module 206. An accelerometer included in sensors 212 may be embodied as a piezoelectric crystal for producing a signal correlated to patient body motion. The use of an accelerometer in an intracardiac device for obtaining a patient activity signal is generally disclosed in U.S. patent application Ser. No. 14/174,514 filed on Feb. 6, 2014 (Nikolski, et al.), incorporated herein by reference in its entirety. The use of a patient activity signal for providing rate-responsive pacing is generally disclosed in U.S. Pat. No. 7,031,772 (Condie, et al.), incorporated herein by reference in its entirety.

In other examples, sensors 212 may include a posture sensor for detecting changes in patient body posture. A multi-dimensional accelerometer for detecting patient posture changes is generally disclosed in U.S. Pat. No. 5,593,431 (Sheldon), incorporated herein by reference in its entirety. Posture changes may be detected for use in triggering an evaluation of P-wave sensing criteria used by the FF event detector 224.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries. The connections between power source 214 and other pacemaker modules and components are not shown in FIG. 3 for the sake of clarity.

Telemetry module 208 includes a transceiver and associated antenna for transferring and receiving data via a radio frequency (RF) communication link. Telemetry module 208 may be capable of bi-directional communication with external device 20 (FIG. 1) as described above.

Figure 4A:
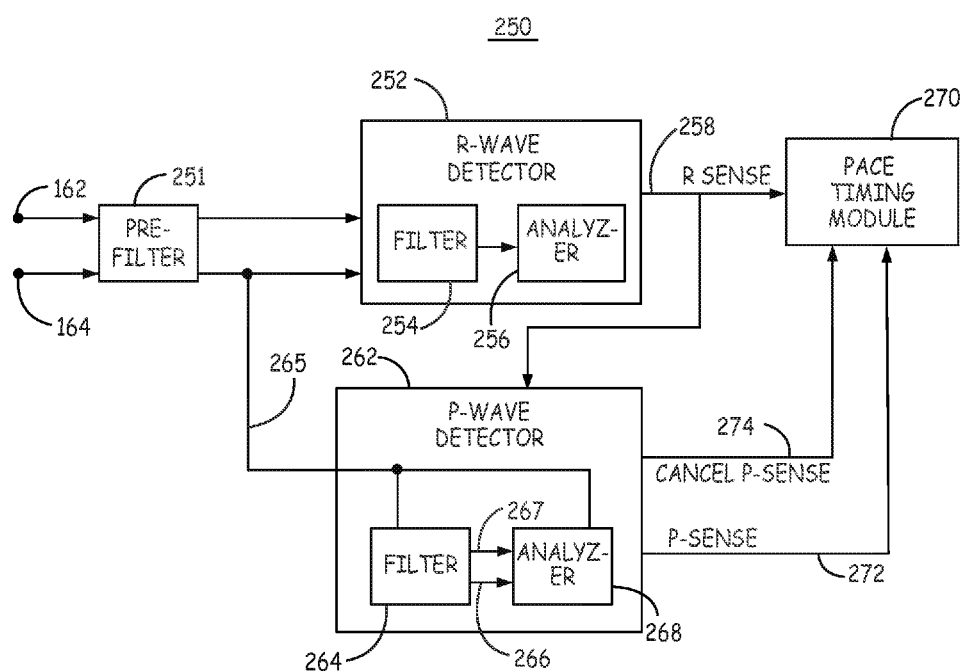
FIG. 4A is a functional block diagram of sensing and pacing control circuitry included in the right ventricular (RV) pacemaker shown in FIG. 1 according to one example.

FIG. 4A is a functional block diagram 250 of sensing and pacing control circuitry included in RV pacemaker 14 according to one example. RV pacemaker 14 includes an R-wave detector 252, which may correspond to NF event detector 222 in FIG. 3, and P-wave detector 262, which may correspond to FF event detector 224 in FIG. 3. Both R-wave detector 252 and P-wave detector 262 receive the ventricular EGM signal developed across electrodes 162 and 164, which may be passed through a pre-filter 251, e.g., 2.5 to 5 Hz high pass filter or a wideband filter having a passband of 2.5 Hz to 100 Hz to remove DC offset and high frequency noise. The signal passed by pre-filter 251 is referred to herein as a "raw cardiac electrical signal" or "raw unfiltered EGM signal" 265 because the signal 265 is minimally filtered by a wideband filter and is not yet filtered by a filter included in P-wave detector 262 or R-wave detector 252. In other words, optimal filtering for sensing cardiac electrical signals has not been applied to the raw, unfiltered EGM signal 265. Pre-filter 251 may pass a differential or single-ended signal to R-wave detector 252 and P-wave detector 262.

R-wave detector 252 includes a bandpass filter 254 for filtering the raw unfiltered EGM signal 265 within a bandwidth including expected R-wave frequencies. R-wave detector filter 254 passes a filtered signal to an analyzer 256 that may include a sense amplifier or other event detector that compares the filtered EGM signal to R-wave sensing criteria. Expected R-wave frequencies may be in the range of approximately 30 Hz to 50 Hz. Filter 254 may have a center frequency between 30 Hz and 50 Hz and a bandwidth as low as 20 Hz and as high as 70 Hz in one example. An R-wave may be sensed by analyzer 256 when the amplitude of the filtered EGM signal crosses an R-wave sensing threshold, which may be auto-adjusting sensing threshold. R-wave detector 252 passes an R-sense signal 258 to pace timing and control module 270, which may be included in control module 206 of FIG. 3. The R-sense signal 258 may also be passed to P-wave detector 262 for use by analyzer 268 for sensing and discriminating P-waves (far-field events) from R-waves and T-waves (both near field events).

Pace timing and control module 270 may include a pacing escape interval timer that is set to a ventricular pacing escape interval in response to receiving sense event signals from R-wave detector 252 and P-wave detector 262. In response to receiving R-sense signal 258 from R-wave detector 252, the pace timing and control module 270 inhibits a scheduled pacing pulse and resets the pacing escape interval timer to a VV pacing escape interval. The VV pacing escape interval is set to control the ventricular rate. If the VVacing escape interval expires before pace timing and control module 270 receives an R-sense signal 258 or P-sense signal 272, a ventricular pacing pulse is delivered by pulse generator 202 (FIG. 3). Pacing pulse delivery will start another VV pacing escape interval. The VVacing escape interval may be set according to a base pacing rate to provide bradycardia pacing or may be shortened from the base pacing rate interval to a sensor-indicated rate response interval to provide a faster pacing rate to meet the patient's metabolic demand.

It is recognized that R-wave detector 252 may set appropriate blanking and/or refractory intervals to avoid oversensing. For example, after an R-sense signal 258 is produced, a short ventricular blanking interval, e.g., up to 150 ms, may be applied to analyzer 256 such that the same R-wave is not sensed more than once. A ventricular refractory interval, e.g., up to 500 ms, may be applied after the blanking interval to inhibit T-wave oversensing leading to false R-sense signals. In various examples, with no limitation intended, a ventricular refractory interval may be between 300 ms and 400 ms.

P-wave detector 262 includes a bandpass filter 264 for filtering the raw, unfiltered EGM signal 265 within a bandwidth including expected P-wave frequencies and may include expected T-wave frequencies and R-wave frequencies. P-wave detector filter 264 may be an adjustable bandpass filter that is automatically adjusted by sensing module 204 (under the control of control module 206 in some examples) to promote separation of P-wave signals from T-wave and R-wave signals. Separation of P-wave signals from T- and R-wave signals may be based on peak signal amplitude, slew rate or other morphology features, and/or time of occurrence in the filtered EGM signal 266.

Generally, T-waves may have a lower frequency, e.g., 10 Hz or lower, than the frequencies of P-waves and R-waves, e.g., 15 Hz or higher and 30 Hz or higher respectively. In one example, filter 264 is nominally adjusted to be a 20 to 70 Hz bandpass filter, but both the high and low ends of the bandpass can be adjusted. However, a "typical" signal frequency may change with changes in electrode position, electrode spacing or other factors. By adjusting a center frequency and bandwidth for filter 264, the P-wave signal may be enhanced and the T-wave signal may be attenuated such that P-wave and T-wave discrimination is reliable. In other words, if the filter bandpass largely eliminates the T-wave from filtered signal 266, a P-wave sensing threshold may be used to detect P-waves when the amplitude of T-waves is distinctly smaller due to optimal filtering of T-waves.

In other examples, the center frequency and/or bandpass width of filter 264 may be adjusted to intentionally increase the T-wave amplitude in filtered EGM signal 266 so that the P-wave amplitude is distinctly lower than the T-wave amplitude. Analyzer 268 receives the filtered EGM signal 266 and includes a rectifier for rectifying the filtered EGM signal 266 and a sense amplifier or other cardiac event detector that receives the rectified, filtered signal for comparison to a P-wave sensing threshold used for sensing P-waves from the filtered EGM signal 266. The cardiac event detector included in analyzer 268 may further apply a T-wave sensing threshold that is higher than the P-wave sensing threshold to enable sensing of P-waves when the filtered EGM signal 266 exceeds the P-wave sensing threshold but not the T-wave sensing threshold. A P-sense signal 272 is produced in response to sensing a P-wave.

It is recognized that P-wave detector 262 may set relevant blanking and/or refractory periods used by analyzer 268 to avoid oversensing. For example, after a P-sense signal 272 is produced, an atrial refractory period, e.g., up to 500 ms, may be applied, during which P-sense signals 272 are not used by pace timing and control module 270 for setting the escape interval timer. Additionally, P-wave detector 262 may set an atrial blanking period in response to R-sense signal 258 during which no P-sense signals 272 are produced, followed by a post-ventricular atrial refractory period during which a P-sense signal 272 is ignored by pace timing and control module 270.

The filtered EGM signal 266 and/or the raw, unfiltered EGM signal 265 received from electrodes 162 and 164 may be passed to analyzer 268 for comparison to P-wave sensing criteria. Analyzer 268 may compare the filtered EGM signal 266 to amplitude criteria, frequency criteria, timing criteria relative to an R-sense signal 258 received from R-wave detector 252, morphology criteria, or any combination thereof for sensing a P-wave. Analyzer 268 may include a digital converter for obtaining multi-bit digital EGM signal samples used for determining and comparing EGM signal features to P-wave sensing criteria.

In some examples, analyzer 268 receives the raw, unfiltered EGM signal 265 from electrodes 162 and 164 to perform comparisons between suspected T-waves and suspected P-waves present in the filtered EGM signal 266 to P-waves and T-waves that can be identified in the unfiltered EGM signal 265. Comparisons of the raw, unfiltered EGM signal P-waves and T-waves may be used to establish P-wave sensing criteria that distinguish P-waves from T-waves as described in greater detail below. Analyzer 268 may automatically adjust the P-wave sensing criteria used by analyzer 268 as needed to discriminate P-waves from T-waves based on analysis of the raw unfiltered EGM signal 265 and/or filtered EGM signal 266.

In some examples, filter 264 may provide filtered EGM signal 266 and another alternate filtered EGM signal 267 for comparison to the filtered EGM signal 266 for identifying P-waves and T-waves. For example, alternate filtered EGM signal 267 may have the same or a different center frequency and broader bandwidth than filtered EGM signal 266. As described below in conjunction with FIG. 8, the filtered EGM signal 266 may be analyzed to confirm that P-waves are being discriminated from T-waves. If P-wave sensing cannot be confirmed based on analyzing filtered EGM signal 266 alone, the unfiltered EGM signal 265 or an alternate filtered EGM signal 267 may be analyzed to identify P-waves and/or T-waves and compare the occurrence of P-waves and/or T-waves in the unfiltered or alternate filtered EGM signals 265 and 267, respectively, to the filtered EGM signal 266 to improve P-wave sensing criteria and confirm P-wave discrimination from T-waves by P-wave detector 262.

Comparisons between P-waves and T-waves identified on the unfiltered EGM signal 265 by analyzer 268 may be made to improve discrimination and separation of P-waves and T-waves in the filtered EGM signal 266. For example, sensing module 204 may adjust filter 264 for increasing amplitude separation of P-waves and T-waves and/or adjust a T-wave sensing window to separate P-waves and T-waves based on time.

Comparisons between the P-waves and T-waves within and between the unfiltered EGM signal 265 and filtered EGM signal 266 may be used by analyzer 268 to automatically adjust the center frequency and/or bandwidth of filter 264 to increase amplitude separation of P-waves and T-waves by reducing the T-wave signal strength and/or increase the P-wave signal strength in the filtered EGM signal 266. The bandpass of filter 264 may be narrowed for example, to reduce the signal strength of the T-wave in the filtered EGM signal 266. If the P-wave frequency is approximately 20 Hz and the T-wave frequency is approximately 10 Hz, for example, the center frequency of filter 264 may be set at 20 Hz. If the P-wave is relatively narrow, e.g., due to the electrodes being closer to the atria, a higher center frequency, e.g., 30 Hz may be used. If the P-wave is relatively wide, e.g., due to the electrodes being further from the atria, a lower center frequency, for example less than 20 Hz may be used. The bandwidth may be set to attenuate lower frequencies, e.g., 10 Hz and lower, which are more typical of T-waves.

In other examples, filter 264 is adjusted to increase the T-wave amplitude in the filtered EGM signal 266 to provide greater amplitude separation between P-waves and T-waves. T-wave amplitude may be intentionally increased by adjusting the center frequency of filter 264 to a lower center frequency, e.g., 10 Hz, or increasing its bandwidth in the lower frequency range, e.g., frequencies less than 15 Hz. If T-waves and P-waves have similar amplitudes on the unfiltered EGM signal 265 but different signal widths, the P-wave detector filter 264 may be adjusted to increase the T-wave amplitude to allow amplitude thresholds to be used to discriminate between P- and T-waves in the filtered EGM signal 266.

Analyzer 268 may set a T-wave sensing window in response to R-sense signal 258 to encompass a time interval that a T-wave is likely to occur (and a P-wave is less likely to occur) for discriminating T-waves from P-waves. The start time and/or duration of a T-wave sensing window set in response to the R-sense signal 258 may be adjusted, automatically by analyzer 268, to separate P-waves from T-waves. For example, analyzer 268 may shorten the duration of the T-wave sensing window in response to an increase in the sensed or paced ventricular rate.

A P-sense signal 272 is passed to pace timing and control module 270 in response to P-wave sensing criteria being met. Pace timing and control module 270 starts the pacing escape interval timer in response to the P-sense signal 272 by setting the pacing escape interval timer to an AV interval. As described below, an initial P-sense signal 272 may be passed to pace timing and control module 270 in response to the amplitude of the filtered EGM signal 266 crossing a P-wave sensing threshold. The P-wave sensing threshold is set lower in amplitude than an R-wave sensing threshold. As such, a signal crossing the P-wave sensing threshold may be a P-wave, an R-wave or a T-wave. Analyzer 268 analyzes the signal after a crossing of the P-wave sensing threshold occurs to confirm that the signal is a true P-wave.

Confirmation of a sensed P-wave may be delayed following the crossing of the P-wave sensing threshold due to additional time needed to verify that the sensed signal is not an R-wave or a T-wave. For example, subsequent to the crossing of the P-wave sensing threshold, analyzer 268 may wait for a T-wave sensing threshold crossing and/or an R-wave sensing threshold crossing to verify that the sensed P-wave threshold crossing is a true P-wave. During the AV interval started upon the P-sense signal 272 produced when the filtered EGM signal 266 crossed the P-wave sensing threshold, analyzer 268 may determine one or more EGM signal features such as a peak amplitude, frequency content, slew rate, morphology, timing relative to an R-sense signal 258 and/or perform other signal analysis to confirm that the crossing of the P-wave sensing threshold is a true P-wave.

In some examples, analyzer 265 includes a differentiator and/or an integrator for producing a differential EGM signal from the raw unfiltered signal 265 and/or from the filtered EGM signal 266 for use in confirming a sensed P-wave. For example, a slew rate and/or amplitude of the differential signal may reliably discriminate a sensed P-wave from a T-wave because the T-wave may be strongly attenuated in the differential signal making the slew rate of the differential signal a strong discriminator in some instances. In another example, the integrated T-wave signal may be a larger wider signal than the integrated P-wave signal facilitating identification and clear discrimination of a T-wave from a P-wave. Examples of a raw, unfiltered signal 265, a filtered signal 266, a differential signal and an integrated signal produced by analyzer 268 are shown in FIG. 7B and described below.

If the signal sensed by P-wave detector 262 is not confirmed as a true P-wave, a Cancel P-sense signal 274 may be passed to pace timing and control module 270. Pace timing and control module 270 may reset, adjust or cancel the AV pacing escape interval in response to the Cancel P-sense signal 274. If the crossing of the P-wave sensing threshold is confirmed to be a true P-wave signal by analyzer 268, the pace timing and control module 270 controls pulse generator 202 to deliver a pacing pulse upon expiration of the AV pacing escape interval.

In some cases, the P-waves and T-waves are indistinguishable from each other on the raw unfiltered EGM signal 265 and filtered EGM signals 266 and 267 based on frequency, amplitude, morphology and timing. If analyzer 268 determines that P-waves and T-waves are indistinguishable, the P-wave detector 262 may be temporarily disabled and/or pace timing module 270 may be disabled from receiving or using P-sense signals 272 for the purposes of setting the ventricular pacing escape interval timer. The RV pacemaker 14 operates in a single chamber ventricular pacing and sensing mode until analyzer 268 determines that P-waves and T-waves are distinguishable again.

The techniques disclosed herein are described in the context of RV pacemaker 14 having a NF event detector 222 shown in FIG. 3 for detecting NF R-waves (which may correspond to R-wave detector 252 in FIG. 4A) and a FF event detector 224 shown in FIG. 3 for detecting FF P-waves (which may correspond to P-wave detector 262 in FIG. 4A). It is understood that the disclosed techniques described in the context of a RV pacemaker implementation may be adapted for use in RA pacemaker 12. In such embodiments, the NF event detector 222 is configured to detect NF P-waves and the FF event detector 224 is configured to detect FF R-waves (and optionally FF T-waves). In this case, R-wave detector 252 may correspond to the FF event detector 224 and may have an adjustable filter 254 that is automatically adjusted to increase separation of FF R-waves from NF P-waves and FF T-waves in time, amplitude and/or morphology in the filtered cardiac electrical signal.

In the examples described below in conjunction with FIGS. 5A, 5B and 5C, cardiac event sensing thresholds are described based on detecting FF P-waves from a cardiac electrical signal received by RV pacemaker 14. In RA pacemaker implementations, the relative amplitudes of these cardiac event sensing thresholds may change based on the expected relative amplitudes of the NF P-wave, FF R-wave and FF T-wave in a filtered cardiac electrical signal produced by the RA pacemaker FF event detector 224.

Figure 4B:
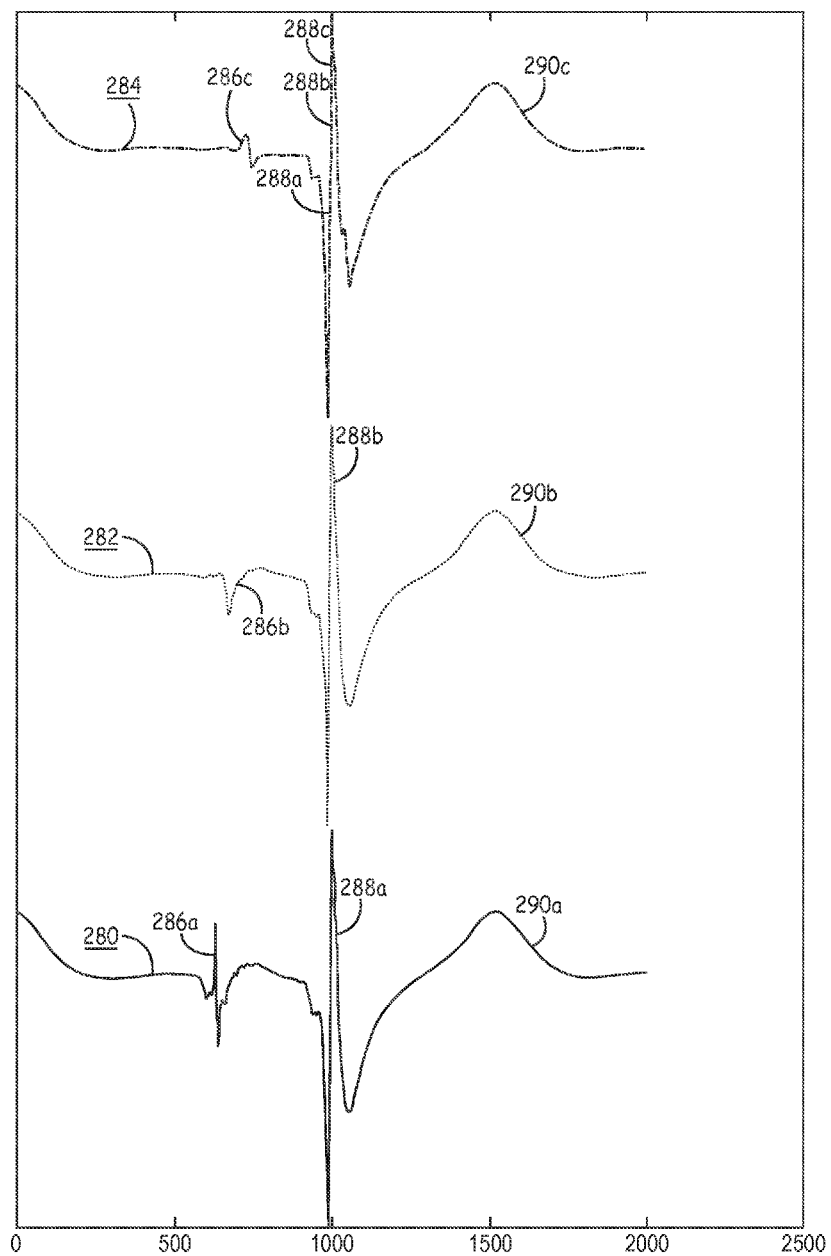
FIG. 4B is a depiction of raw unfiltered EGM signals received by the P-wave detector of FIG. 4A.

FIG. 4B is a depiction of raw unfiltered EGM signals 280, 282 and 284 received by P-wave detector 262. The raw unfiltered EGM signals 280, 282, and 284 may correspond to raw, unfiltered EGM signal 265 shown in FIG. 4A passed by pre-filter 251 after wideband filtering to remove DC offset and high frequency noise. The three raw, unfiltered EGM signals 280, 282, and 284 are acquired using electrodes positioned at three different inter-electrode spacings. Signal 280 is acquired using an inter-electrode spacing of 131 mm. Signal 282 is acquired using an inter-electrode spacing of 100 mm, and signal 284 is acquired using an inter-electrode spacing of 60 mm in this example. The greater inter-electrode spacing may be achieved using a sensing extension, e.g., as shown in FIG. 2B.

As observed in FIG. 4B, the amplitude and morphology of the P-waves 286a, 286b and 296c may change substantially with increasing inter-electrode distance. The R-waves 288a, 288b and 288c, and T-waves 290a, 290b, and 290c do not change as substantially with inter-electrode distance in the examples shown. The effect of inter-electrode spacing on the P-wave and the relative differences between P-waves, R-waves T-waves may vary with implant position of electrodes 162 and 164 as well as inter-electrode spacing.

In the example shown, the maximum peak amplitude and maximum slope of P-waves 286a, 286b, and 286c are observed to increase with increasing inter-electrode spacing because the proximal return electrode 162 may be positioned closer to atrial tissue. The increased inter-electrode spacing may therefore be used to acquire P-waves having a higher amplitude that is more easily detected by a P-wave sensing threshold crossing applied by P-wave detector analyzer 268. The higher amplitude of P-wave 286a, for example, is still easily distinguishable from the R-wave amplitude, e.g., by using a P-wave sensing threshold set well above EGM baseline variation but lower than the R-wave peak amplitude as described in greater detail below. In some cases, analyzer 268 may further apply an intermediate T-wave sensing threshold greater than the P-wave sensing threshold and less than the R-wave sensing threshold to distinguish the P-wave 286a, 286b or 286c from the T-wave 290a, 290b, or 290c. In other cases, the enhanced peak amplitude of P-wave 286a and high slew rate or other distinct morphology features of the P-wave 286a may enable sensing of P-wave 286a by analyzer 268 without requiring an intermediate T-wave sensing threshold.

Figure 4C:
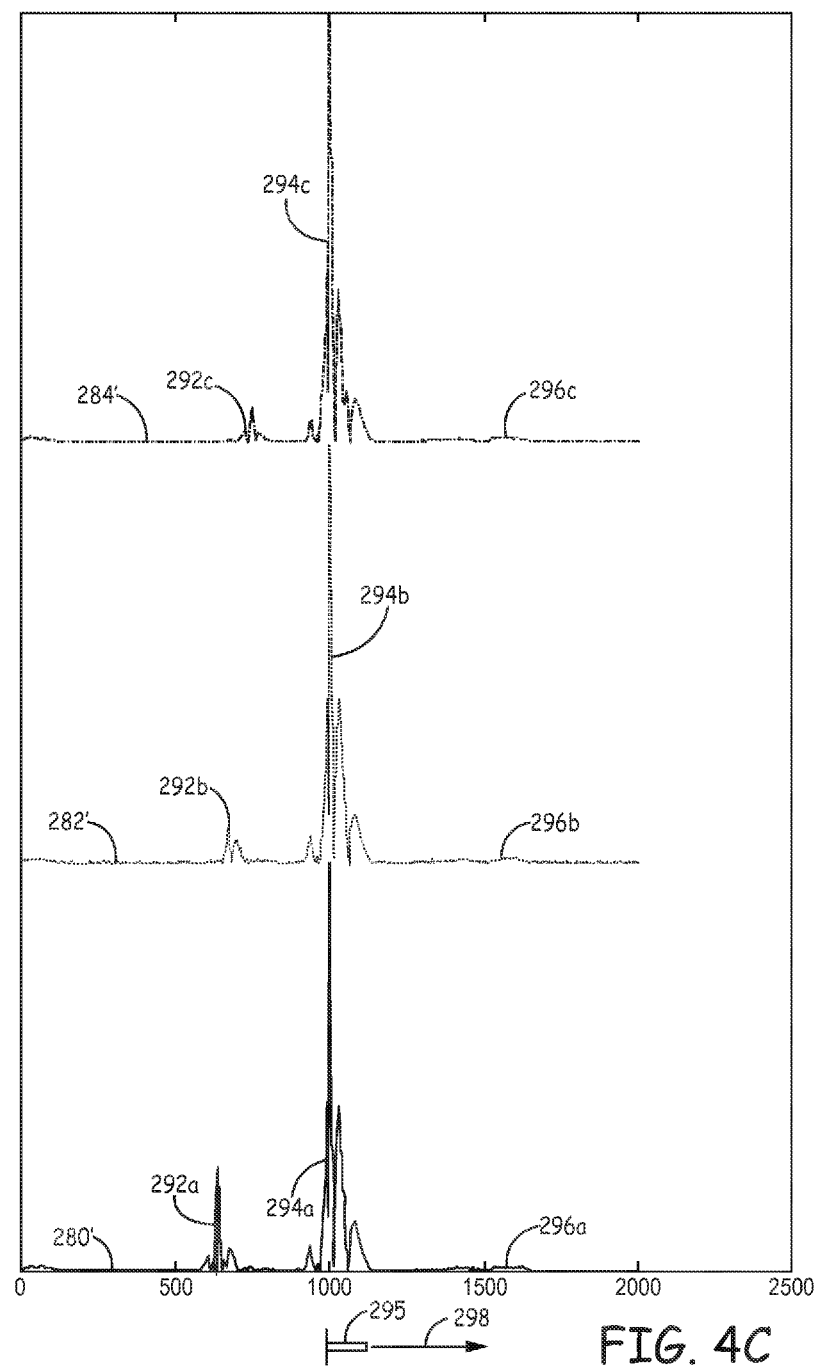
FIG. 4C is a depiction of filtered, rectified EGM signals produced after filtering and rectifying the respective unfiltered EGM signals of FIG. 4B.

FIG. 4C is a depiction of filtered, rectified EGM signals 280', 282', and 284' produced after filtering and rectifying the respective unfiltered EGM signals 280, 282 and 284 of FIG. 4B by P-wave detector 262. Signals 280', 282' and 284' are filtered by a 20 Hz highpass filter in this example, resulting in significant attenuation of T-waves 296a, 296b and 296c compared to respective raw, unfiltered T-waves 290a, 290b and 290c shown in FIG. 4B. As described below, in some examples sensing of P-waves 292a, 292b or 292c from the filtered EGM signal 266 received by analyzer 268 may be confirmed when a T-wave 290a, 290b or 290c can be identified from the raw, unfiltered EGM signal 265 (e.g., T-wave 290a, 290b, or 290c of raw, unfiltered EGM signals 282, 284 or 286, respectively) that is not coincident with a P-sense signal 272.

In other examples, the T-wave may still be present in the filtered EGM signal 266 with an amplitude that interferes with amplitude-based P-wave sensing in which case additional P-wave sensing criteria may be applied by analyzer 268 for sensing P-waves. Additional P-wave sensing criteria may be based on the higher slope (i.e., slew rate), narrow signal width or other waveform morphology differences of the P-wave 292a, 292b or 292c compared to the lower slope and higher signal width of the T-wave 296a, 296b or 296c.

P-wave detector analyzer 268 may additionally or alternatively apply a T-wave sensing window 298, also referred to herein as a "T-wave window," for confirming a P-wave sensing threshold crossing as a P-wave. T-wave window 298 may be applied after a post-sense blanking period 295 following an R-sense signal 258 produced by R-wave detector 252 (or upon detecting an R-wave sensing threshold crossing of filtered EGM signal 266 by P-wave detector analyzer 268 as described below in conjunction with FIG. 5B). Post-sense blanking period 295 may be applied by R-wave detector 252 (or P-wave detector 262) to avoid double-sensing of R-wave 294*a*, 294*b* or 294*c*. A maximum peak amplitude may be determined during blanking period 295 for setting the starting value of an auto-adjusting R-wave sensing threshold used by R-wave detector 252 and/or P-wave detector 262.

The T-wave window 298 may be applied to exclude P-wave sensing threshold crossings during T-wave window 298 from being sensed as P-waves in some examples. As described in greater detail below, T-wave window 298 may be adjusted to provide temporal discrimination of P-waves 292*a-c* from T-waves 296*a-c*, respectively. T-wave sensing window 298 may be adjusted in response to heart rate changes, in response to changes between a ventricular paced rhythm and a sensed intrinsic ventricular rhythm, and as needed to provide reliable P-wave sensing and discrimination from T-waves.

Figure 5A:
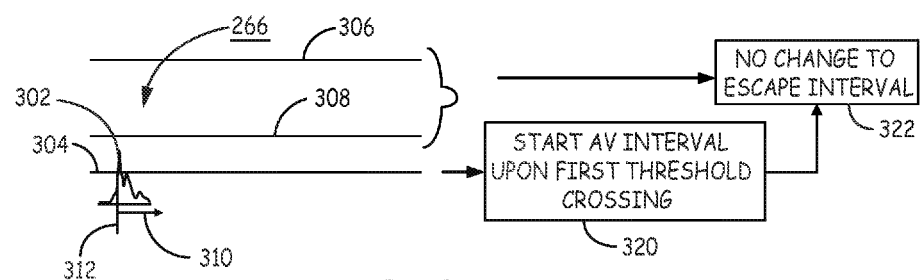
FIG. 5A is a conceptual diagram of a P-wave portion of a ventricular EGM signal.
Figure 5B:
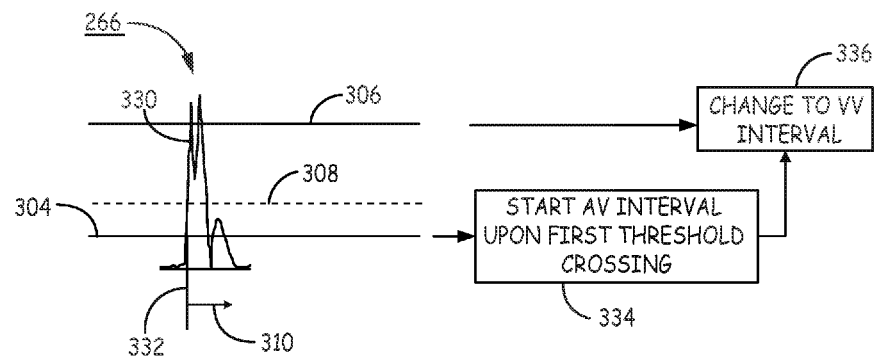
FIG. 5B is a conceptual diagram of an R-wave portion of the ventricular EGM signal of FIG. 5A.
Figure 5C:
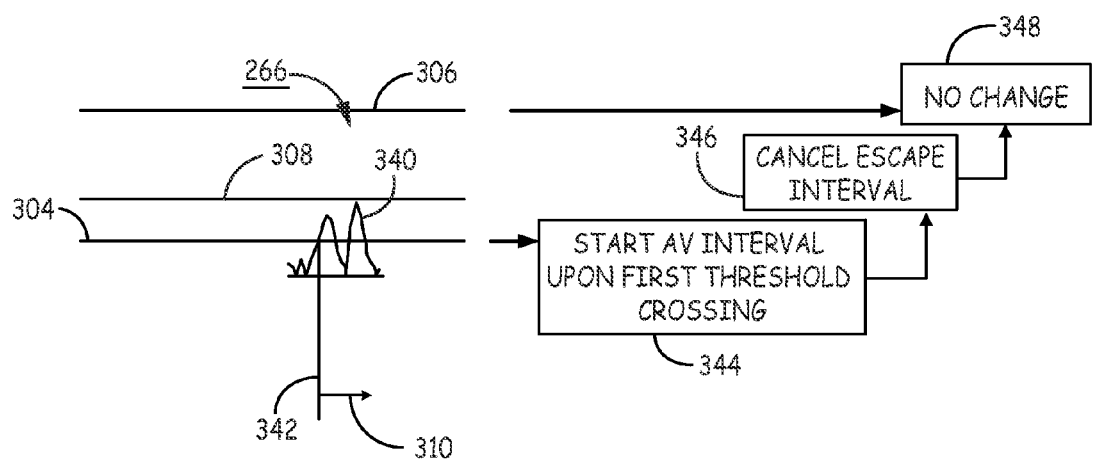
FIG. 5C is a conceptual diagram of a T-wave portion of the ventricular EGM signal of FIG. 5A.

FIGS. 5A, 5B, and 5C are diagrams of a P-wave, R-wave and T-wave of a filtered EGM signal 266 after rectification by analyzer 268. Various sensing thresholds 304, 306 and 308 used by the sensing and pacing control circuitry shown in FIG. 4A for sensing P-waves and controlling a pacing escape interval timer are shown. FIG. 5A is a conceptual diagram of a P-wave 302 of filtered ventricular EGM signal 266 after rectification by analyzer 268 of FIG. 4A. The analyzer 268 of P-wave detector 262 may apply at least two sensing thresholds 304 and 306 to the amplitude of EGM signal 266 and may apply a third intermediate threshold 308. The first sensing threshold 304 is a relatively lower, P-wave sensing threshold and enables relatively low amplitude P-wave 302 to be sensed. Sensing module 204 may set the P-wave sensing threshold 304 to a value that is expected to be less than a maximum peak amplitude of P-waves of the EGM signal 266, such as P-wave 302.

As the filtered EGM signal 266 begins to rise from a baseline, it will cross the lowest amplitude P-wave sensing threshold 304 first. The filtered EGM signal 266 may continue to increase to cross the second, R-wave sensing threshold 306. The second, R-wave sensing threshold 306 is greater than the P-wave sensing threshold 304. An intermediate, T-wave sensing threshold 308 may be defined that is greater than the P-wave sensing threshold 304 and less than the R-wave sensing threshold 306.

In some examples, the P-wave detector filter 264 is tuned to eliminate T-waves from the EGM signal 266 or reduce the maximum T-wave signal amplitude to be consistently less than P-wave sensing threshold 304. In such cases, the intermediate threshold 308 is not required. In other examples, P-wave detector filter 264 is tuned to enhance or maximize T-wave amplitude so that it is consistently greater than the amplitude of P-wave 302. The intermediate, T-wave sensing threshold 308 may be defined to discriminate between the P-wave 302 and T-waves having consistently higher amplitude.

When the filtered EGM signal 266 crosses the P-wave sensing threshold 304 at 312, it is unknown whether the EGM signal 266 will continue to increase in amplitude and cross the R-wave sensing threshold 306 or T-wave sensing threshold 308. The early increasing portion of the EGM signal 266 could be a P-wave, T-wave or R-wave. The P-wave sensing threshold crossing alone is not enough evidence to confirm P-wave 302.

If the EGM signal 266 crosses the P-wave sensing threshold 304 outside of any atrial blanking period, atrial sensing refractory period, or T-wave window, the threshold crossing at 312 is preliminarily determined to be a P-wave signal. A P-sense signal 272 may be produced by P-wave detector 262 and used by pace timing and control 270 to start a ventricular pacing escape interval set equal to the target AV interval at block 320. In one example, if the EGM signal 266 does not cross the R-wave sensing threshold 306 or the T-wave sensing threshold 308 (if used) during a predetermined time limit 310, the P-wave threshold crossing at 312 is determined to be evidence of a P-wave. The AV pacing escape interval timer started upon P-wave threshold crossing 312 is allowed to continue without adjustment at block 322.

In some examples, EGM signal 266 is determined to cross the higher R-wave sensing threshold 306 or T-wave sensing threshold by determining the maximum peak amplitude of the rectified filtered EGM signal 266 after the first threshold crossing 312 and comparing the maximum peak amplitude to the respective higher threshold 308 or 306. If the maximum peak amplitude of the signal 302 after crossing the P-wave sensing threshold 304 is not greater than at least one of the higher thresholds 306 or 308, the threshold crossing 312 is confirmed to be a P-wave and the AV pacing escape interval timer continues to run.

If the AV escape interval expires a ventricular pacing pulse is delivered at the target AV interval. In other examples, as described below, P-wave detector 262 may perform additional signal analysis to confirm that the P-wave threshold crossing is a P-wave during the AV interval. The cancel P-sense signal 274 may be produced by P-wave detector 262 if additional signal analysis fails to confirm the P-wave.

The time limit 310 may be set by the sensing module 204 to a nominal value, e.g., 120 ms or based on an expected cardiac event width or slope of the filtered cardiac electrical signal, e.g., an R-wave width, R-wave slope, T-wave width, or T-wave slope, such that if the EGM signal crossing of the P-wave sensing threshold is actually an R-wave or T-wave, a higher R-wave sensing threshold or T-wave sensing threshold will be crossed within the time limit following the P-wave sensing threshold crossing. The time limit is set shorter than an expected P-R interval to reduce the likelihood of two different events, e.g., one P-wave and one R-wave, being sensed within the time limit.

For example if time limit 310 is set to at least half the expected T-wave width or at least half of the expected R-wave width of the filtered cardiac electrical signal, e.g., up to 80 ms, the EGM signal 266 will cross the respective T-wave sensing threshold 308 or R-wave sensing threshold 306 within the time limit 310 if the rising amplitude of the EGM signal is actually due to a T-wave or R-wave instead of P-wave 302. Time limit 310 may be established by analyzer 268 of P-wave detector 262 by determining the lowest slope or the widest signal width of a T-wave or R-wave in the filtered EGM signal 266. Alternatively time limit 310 is a nominal value stored in RV pacemaker memory 210, which may be based on clinical data and any expected delays in the filtered cardiac electrical signal.

FIG. 5B is a conceptual diagram of an R-wave 330 of a ventricular EGM signal 266. When EGM signal 266 crosses the P-wave sensing threshold 304 at time 332, the escape interval timer is set to an AV interval at block 334. If the EGM signal 266 crosses the R-wave amplitude 306 within the time limit 310, the escape interval timer started at block 334 is adjusted to a VV interval at block 336 in response to the R-wave sensing threshold crossing.

In some examples, the P-wave detector analyzer 268 may set the R-wave sensing threshold 306. Alternatively, the separate R-wave detector 252 (shown in FIG. 4A) produces an R-sense signal 258 in response to an R-wave 330, which causes the pace timing and control module 270 to reset the pacing escape interval timer to the VV interval at block 336, effectively cancelling the relatively shorter AV interval started at block 334.

FIG. 5C is a conceptual diagram of a T-wave 340 of the filtered EGM signal 266. In some examples, P-wave detector filter 264 is adjusted to minimize the T-wave amplitude in the filtered EGM signal 266 such that only a P-wave sensing threshold 304 and R-wave sensing threshold 306 are used for controlling the ventricular escape interval as described in conjunction with FIGS. 5A and 5B. In other examples, the T-wave amplitude may be higher than the P-wave amplitude in the filtered EGM signal 266. In this case, the T-wave threshold 308, intermediate the P-wave amplitude 304 and R-wave amplitude 306, is used to discriminate between P-waves 302 and T-waves 340. The amplitude of T-wave 340 may be intentionally increased through adjusting the center frequency and bandwidth of filter 264 to provide amplitude discrimination between P-waves 302 and T-waves 340.

When EGM signal 266 crosses the P-wave sensing threshold 304 at time 342, the escape interval timer is set to an AV interval at block 344. If the EGM signal 266 crosses the intermediate T-wave amplitude 308 within the time limit 310, the AV escape interval is cancelled at block 346 without setting a new pacing escape interval. If the EGM signal 266 does not cross the R-wave sensing threshold 306, no change is made at block 348, i.e., the escape interval remains cancelled and no new escape interval is started. In this way, the T-wave 340 is ignored for the purposes of starting an escape interval and detection of the T-wave threshold crossing with no R-wave threshold crossing within time limit 310 cancels the AV interval started upon the P-wave threshold crossing. If the EGM signal 266 crosses R-wave threshold 306 during time limit 310 after crossing T-wave threshold 308, a pacing escape interval set to a desired VV interval may be started.

Alternatively, instead of waiting for another threshold crossing, a maximum peak amplitude of the filtered EGM signal 266 (after rectification) is determined in response to the P-wave sensing threshold crossing 342. If the maximum amplitude of the signal peak occurring after the P-wave sensing threshold crossing 304 is greater than the R-wave sensing threshold 306, the AV pacing escape interval is changed to a VV pacing escape interval. If the maximum peak amplitude is greater than the T-wave sensing threshold 308, when used as an intermediate threshold, but not greater than the R-wave sensing threshold 306, the AV pacing escape interval is canceled.

In the examples of FIGS. 5A, 5B, and 5C the P-wave sensing threshold 304, T-wave sensing threshold 308 and R-wave sensing threshold 306 are each shown as constant values. It is contemplated that a cardiac event sensing threshold is an auto-adjusting threshold that has a starting threshold amplitude that decays at one or more decay rates to a sensing floor. In some examples, the cardiac event sensing thresholds described herein may be automatically adjusted by the sensing module 204 based on maximum peak cardiac event amplitude determined during a post-sense blanking interval and optionally using one or more decay rates and intervals and/or step-drop times.

In the example described above, the pace timing and control module 270 responds to a P-wave threshold crossing, T-wave threshold crossing and R-wave threshold crossing as it occurs by starting an AV escape interval, cancelling the AV escape interval or changing to a VV escape interval respectively. In other examples, the pace timing and control module 270 may wait for the time limit 310 to expire before responding to a threshold crossing and/or P-wave detector 262 may wait for time limit 310 to expire before producing the P-sense signal 272. If only a P-wave sensing threshold crossing occurs during time limit 310, the P-sense signal 272 is produced at the expiration of time limit 310. The pace timing and control module 270 starts the escape interval timer set to the target AV interval (less time limit 310) in order to deliver the ventricular pacing pulse at the target AV interval after P-wave 302. If the R-wave sensing threshold 306 is crossed before time limit 310 expires, pace timing and control module 270 starts a VV interval at block 336 at the expiration of the time limit 310. If the intermediate T-wave sensing threshold 308 is crossed during time limit 310 but R-wave sensing threshold 306 is not crossed, no P-sense signal 272 is produced and no escape interval is started.

The initial crossing of the P-wave sensing threshold 304 is invalidated as a true P-wave signal if the EGM signal amplitude reaches the higher T-wave sensing threshold 308 or R-wave sensing threshold 306 within time limit 310. The P-wave detector 262 may produce the Cancel P-sense signal 274 in response to a crossing of the T-wave sensing threshold 308 or R-wave sensing threshold 306 to cause pace timing and control module 270 to cancel an AV interval started at block 344.

In some cases, it may be possible to adjust filter 264 to cause the amplitude of T-wave 340 to be greater than the amplitude of R-wave 330, depending on the location of electrodes 162 and 164. The T-wave threshold would be the highest threshold and the R-wave threshold would be the intermediate threshold in this case. If the EGM signal 266 crosses the P-wave threshold, the AV interval is started. If the intermediate R-wave threshold is crossed, the AV interval is changed to a VV interval. If the highest, T-wave threshold is crossed, the VV interval is cancelled.

Figure 6:
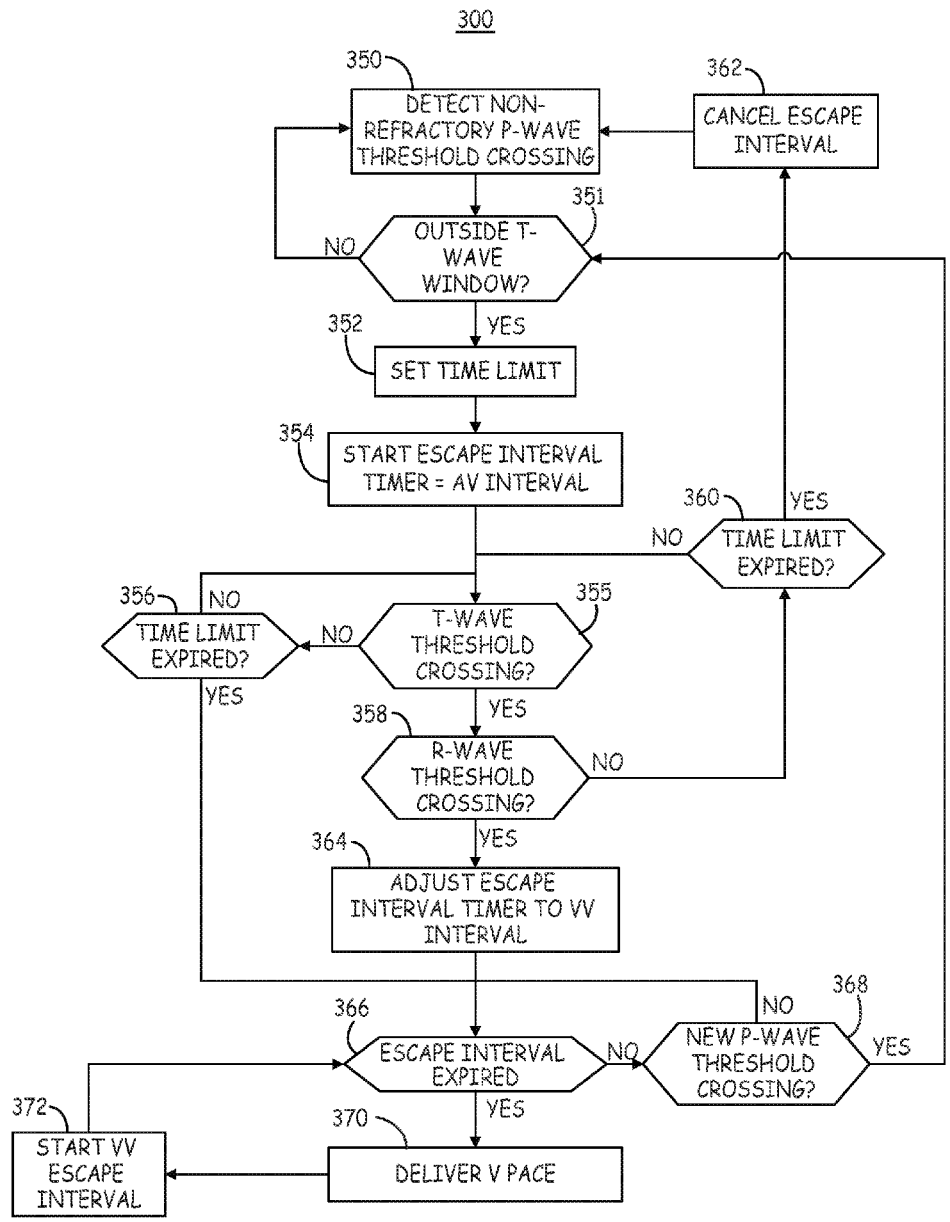
FIG. 6 is a flow chart of a method for controlling ventricular pacing pulse delivery using far-field P-wave sensing by RV pacemaker of FIG. 1.

FIG. 6 is a flow chart 300 of a method for controlling ventricular pacing pulse delivery using FF P-wave sensing by RV pacemaker 14. Methods described in conjunction with flow chart 300 and other flow charts presented herein may be implemented in a computer-readable medium that includes instructions for causing a programmable processor to carry out the methods described. The instructions may be implemented as one or more software modules, which may be executed by themselves or in combination with other software.

At block 350, a P-wave threshold crossing is detected by P-wave detector 262. It is recognized that the P-wave threshold crossing detected at block 350 used for setting an AV pacing escape interval may be required to occur outside an atrial blanking interval and outside a post-ventricular atrial refractory period.

Furthermore, a T-wave window may be established by P-wave detector 262 for discriminating between P-waves and T-waves based on relative timing from an R-wave. After receiving an R-sense signal 258, P-wave detector 262 may start a T-wave window during which any P-wave sensing threshold crossings are ignored as most likely being T-waves. As such, if the P-wave sensing threshold crossing detected at block 350 is during a T-wave window as determined at block 351, the P-wave detector 262 may return to block 350 to wait for the next P-wave threshold crossing.

The T-wave window may begin upon receiving the R-sense signal 258 (or upon delivering a ventricular pacing pulse) and expire at a time interval after the R-sense signal 258 (or ventricular pacing pulse) that is expected to encompass a T-wave but not the P-wave of the next cardiac cycle. The T-wave window may be approximately 300 to 600 ms long in some examples, and may extend at least approximately 500 ms after the R-wave during resting heart rates. The T-wave window may be adjusted based on heart rate and/or based on whether the T-wave window is set in response to an R-sense signal 258 or in response to a ventricular pacing pulse.

If a non-refractory P-wave threshold crossing is detected outside a T-wave window ("yes" branch of block 351), the P-wave detector 262 starts the time limit 310 (shown in FIGS. 5A-5C) at block 352. The P-wave detector 262 may produce a P-sense signal 272, and pace timing and control module 270 responds to the P-sense signal by setting the ventricular pacing escape interval timer to an AV interval at block 354. If a T-wave sensing threshold crossing is detected at block 355 before the time limit 310 expires (block 356), P-wave detector 262 may produce a Cancel P-sense signal 274 (FIG. 4A) causing pace timing and control 270 to immediately cancel the pacing escape interval at block 362.

Alternatively, the pace timing and control module 270 may wait for the time limit 310 to expire to determine if an R-wave sensing threshold crossing is detected at block 358. If the T-wave sensing threshold is crossed (block 355), but the R-wave sensing threshold is not reached (block 358) before the time limit expires (block 360), the AV pacing escape interval started at block 354 is cancelled at block 362. It is to be understood that in some examples, the P-wave detector filter 264 eliminates or significantly attenuates T-wave signals so that the peak T-wave amplitude is significantly smaller than the peak P-wave amplitude. In this case, a T-wave sensing threshold may not be required. Pace timing and control module 270 may monitor only for an R-wave sensing threshold crossing at block 358 within the time limit 310 after the P-wave sensing threshold crossing.

If the R-wave sensing threshold is crossed within the time limit at block 358, the pace timing and control module 270 changes the pacing escape interval timer from the AV interval set at block 354 to a VV interval at block 364. The crossing of an R-wave sensing threshold may be determined by R-wave detector 252 at block 358, resulting in an R-sense signal 258, or by P-wave detector 262 causing a Cancel P-sense signal 274 to be produced.

As indicated above, rather than waiting for a T-wave threshold crossing at block 355 or an R-wave threshold crossing at block 358, the P-wave detector 262 may determine a maximum peak amplitude of the filtered EGM signal 266 after the P-wave threshold crossing and compare the maximum peak amplitude to a T-wave threshold and/or R-wave threshold at respective blocks 355 and 358.

During the VV pacing escape interval, the R-wave detector 252 and P-wave detector 262 may continue to monitor for R-waves and P-waves at block 368 by monitoring for a new P-wave sensing threshold crossing outside any applicable atrial blanking or refractory periods. For example an atrial blanking interval and a post-ventricular atrial refractory period may be set after the R-wave sensing threshold crossing is detected at block 358. If a new crossing of the P-wave sensing threshold is detected at block 368, during the currently running escape interval but outside any atrial blanking or refractory, and outside the T-wave window as determined at block 351, the pace timing and control module 270 restarts the time limit at block 352. The ventricular pacing escape interval timer is reset to the target AV interval at block 354. The process of waiting to confirm the threshold crossing as a P-wave based on no higher sensing threshold crossings within the time limit repeats.

If the AV pacing escape interval set at block 354 expires at block 366, the pace timing and control module 270 controls the pulse generator 202 to deliver a ventricular pacing pulse at block 370. In some examples, the AV pacing escape interval is set up to a maximum AV pacing escape interval limit to prevent delivering a ventricular pacing pulse during the T-wave following a premature ventricular contraction (PVC). A PVC may meet the P-wave sensing criteria and be falsely sensed as a P-wave, causing an AV pacing escape interval to be started. If the AV interval is longer than a maximum limit, e.g., longer than 200 to 300 ms, the ventricular pacing pulse may be delivered during the T-wave which can be arrhythmogenic in some patients.

If the VV pacing escape interval started at block 364 in response to a crossing of the R-wave sensing threshold expires at block 366, a ventricular pacing pulse is delivered at block 370 by the pulse generator 202 under the control of pace timing and control module 270.

A ventricular pulse delivery causes pace timing and control 270 to reset the escape interval timer to a VV pacing escape interval at block 372. The process returns to block 366 after starting the VV pacing escape interval to wait for the escape interval to expire while monitoring for a new P-wave sensing threshold crossing at block 368 during the escape interval but outside any relevant blanking or refractory window.

Figure 7A:
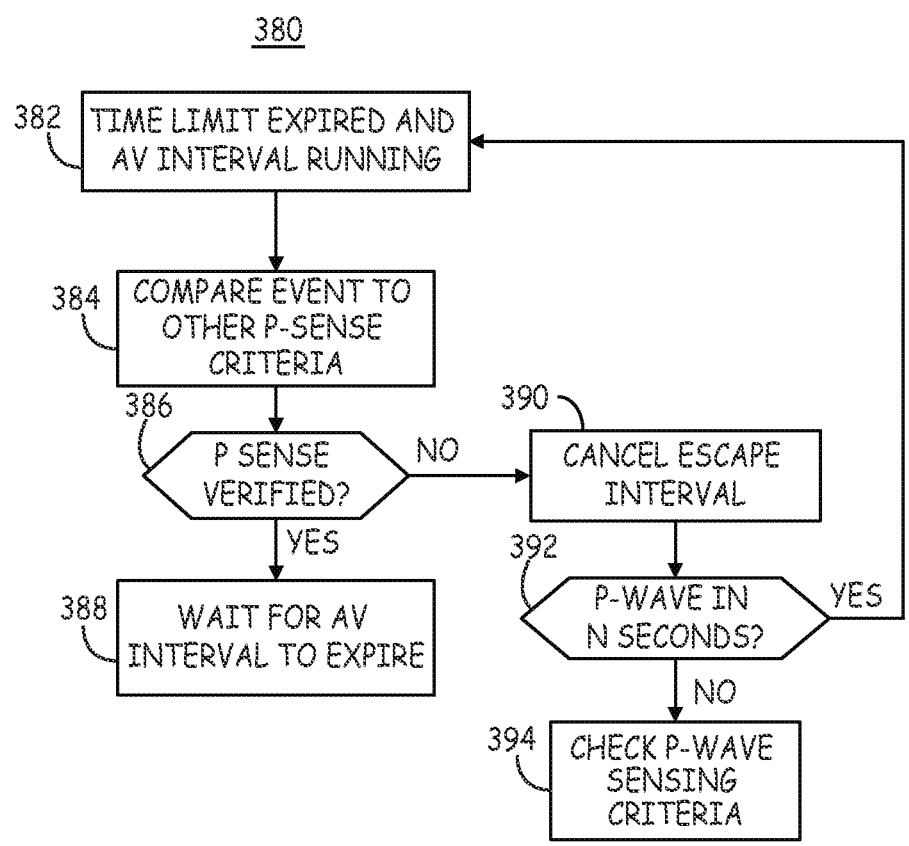
FIG. 7A is a flow chart of a method for controlling ventricular pacing pulse delivery by the RV pacemaker according to another example.
Figure 7B:
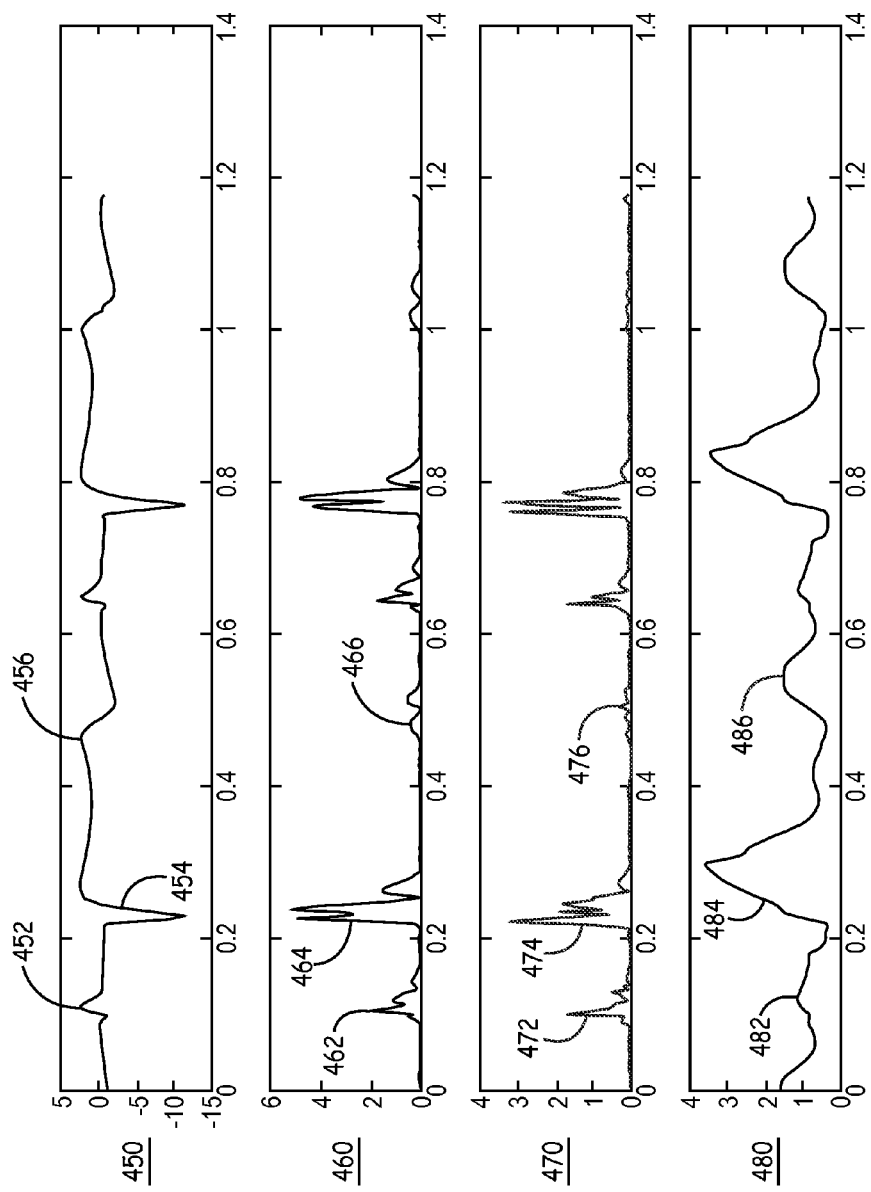
FIG. 7B is a depiction of a raw, unfiltered EGM signal, a filtered, rectified EGM signal, a differential EGM signal and an integrated EGM signal.

FIG. 7A is a flow chart 380 of a method for verifying a P-wave sense event during an AV interval set in response to a P-wave sensing threshold crossing. As described in conjunction with FIG. 6, P-wave detector 262 detects a P-wave sensing threshold crossing and starts a time limit for sensing a next, higher sensing threshold. The pace timing and control module 270 sets the escape interval timer to the target AV pacing escape interval. If the time limit expires without sensing a higher sensing threshold crossing, the AV interval will be running as indicated at block 382. During this AV interval, additional operations may be performed by P-wave detector 262 to verify that the P-wave sensing threshold crossing is a true P-wave. The process shown in FIG. 7A may therefore be performed after the time limit 310 expires and before the AV interval expires to confirm that the signal is a P-wave before delivering a ventricular pacing pulse at block 370 of FIG. 6.

P-wave sensing criteria may be applied to the filtered EGM signal 266 and/or the raw unfiltered EGM signal 265 at block 384. In one example, a P-wave analysis segment may be digitized and stored extending from the P-wave sensing threshold crossing (or a defined time interval or number of sample points earlier) until a defined time interval after the P-wave sensing threshold crossing. The P-wave analysis segment may be set based on an expected P-wave width for example. The signal during the P-wave analysis segment is compared to P-wave sensing criteria at block 384.

P-wave sensing criteria may include a maximum and/or minimum signal width, signal slope, number of inflection points, frequency content or other signal feature threshold. One or more EGM signal features during the P-wave analysis segment, of either the filtered EGM signal 266 or the raw unfiltered EGM signal 265, not meeting the P-wave sensing criteria may disqualify the P-wave sensing threshold crossing as a true P-wave.

In other examples, P-wave sensing criteria may include time interval ranges relative to a previous T-wave or R-wave sensing threshold crossing, or relative to an R-sense signal 258, to discriminate between the expected timing of a P-wave (after a preceding R-wave or a T-wave) and the expected timing of a T-wave (after the preceding R-wave). For example, if the P-wave sensing threshold crossing occurs within a T-wave window set relative to an R-wave sense event signal, this timing evidence may be used to disqualify the P-wave sensing threshold crossing as a true P-wave. If the P-wave sensing threshold crossing occurs outside the T-wave sensing window, the crossing of the P-wave sensing threshold may be confirmed as a P-wave as long as the EGM signal meets any other P-wave sensing criteria requirements.

In still other examples, P-wave sensing criteria applied at block 384 may include criteria applied to a comparison of the P-wave signal analysis segment to an overall waveform morphology template. Sample points of the filtered, digitized EGM signal acquired at regular sampling intervals across the entire signal analysis segment may be compared to a previously stored known P-wave morphology template and/or a previously stored known T-wave morphology template in order to confirm a high correlation of the unknown EGM signal with the P-wave morphology template and/or a low correlation with the T-wave morphology template. If the signal analysis segment is highly correlated with a T-wave morphology template or is poorly correlated with a P-wave morphology template, the P-wave threshold crossing may be disqualified as a true P-wave.

If a P-wave sense event is verified at block 386 based on the comparison of the EGM signal to other P-wave sensing criteria, pace timing and control module 270 waits for the AV pacing escape interval to expire at block 388. It is recognized that an R-wave sensed during the AV interval will cause the escape interval timer to be reset to a VV interval. Otherwise, a ventricular pacing pulse will be delivered upon expiration of the AV pacing escape interval following the verified P-wave.

If a P-wave sense event is not verified in response to the comparison made at block 384, the AV pacing escape interval is cancelled at block 390 prior to its expiration. At block 392, the control module 206 of RV pacemaker 14 may determine if a P-wave sense event has been verified within the previous n seconds, minutes, hours or other predetermined time interval.

In one example, if a P-wave has not been sensed in the past 20 seconds, the P-wave sensing criteria used by the analyzer 268 of P-wave detector 262 is checked and updated if needed at block 394. A time interval up to one minute, for example, may be set after which an absence of a verified P-wave will trigger the P-wave sensing criteria check at block 394. In still other examples, the time interval after which the P-wave sensing criteria is checked if no P-waves have been verified during the time interval may be a progressively increasing time interval. The first time interval may be relative short, e.g., 30 seconds and the next time interval may be doubled or increased by a predetermined increment from the first time interval. To illustrate, as long as at least one or another required minimum number of P-waves are verified within a current time interval, the next time interval is doubled such that the time interval series may include intervals of 30 seconds, 60 seconds, 2 minutes, 4 minutes and so on up to a maximum time interval of one hour for example. After the maximum time interval is reached, the maximum time interval is repeatedly used at block 392. If a required number of P-waves are not sensed during the time interval, P-wave sensing criteria are checked and updated if needed. The time interval series begins again at the first, shortest time interval after an update of the P-wave sensing criteria. Processing power and time are conserved by using relatively longer or progressively increasing time intervals between checking and updating P-wave sensing criteria.

If a P-wave has been confirmed recently based on the P-wave sensing criteria applied at block 384 being satisfied within the N-second interval (block 392), the pace timing and control module 270 returns to block 382 to wait for the next time limit to expire during the next running AV interval. The P-wave sensing criteria used at block 384 is deemed valid if a minimum number of P-waves have been confirmed during the most recent n-seconds.

If a P-wave has not been confirmed within the n-second time interval as determined at block 392, the P-wave sensing criteria used at block 384 to verify a true P-wave may need updating. A change in RV pacemaker position, myocardial substrate, a prescription medication, heart rate, patient position, patient activity or other change or condition may alter the EGM signal such that the P-wave sensing criteria requires updating. Accordingly, the P-wave sensing criteria are checked and updated if needed at block 394 as further described in conjunction with FIG. 8.

FIG. 7B is a depiction of a raw, unfiltered EGM signal 450, a filtered, rectified EGM signal 460, a differential EGM signal 470 and an integrated EGM signal 480. Raw, unfiltered EGM signal 450 corresponds to the wideband pre-filtered EGM signal 265 received by P-wave detector 262 in FIG. 4A and includes a P-wave 452, R-wave 454, and T-wave 456. Filtered, rectified EGM signal 460 corresponds to the filtered EGM signal 266 after rectification by P-wave detector analyzer 268 and includes P-wave 462, R-wave 464 and T-wave 466.

Analyzer 268 may include a differentiator to produce a differential EGM signal 470, which is the differential signal of filtered, rectified EGM signal 460 in this example. In other examples, either one or both of unfiltered EGM signal 450 and filtered EGM signal 460 are differentiated to produce a differential signal used to discriminate P-waves 472 from R-waves 474 and T-waves 476. The T-wave 476 of the differential signal is largely attenuated in the differential signal 470 compared to P-wave 472.

Analyzer 268 may further include an integrator to produce an integrated EGM signal 480. In the example shown, integrated EGM signal 480 is the integrated signal of filtered, rectified EGM signal 460. Analyzer 268 may be configured to produce an integrated signal from one or both of raw, unfiltered EGM signal 450 and filtered EGM signal 460, before and/or after rectification. In the integrated signal 480, P-wave 482 is largely attenuated compared to R-wave 484 and T-wave 486.

P-wave detector 262 may be configured to apply other P-sense criteria at block 384 of FIG. 7A to one or more of the unfiltered EGM signal 450, filtered rectified EGM signal 460, differential signal 470 and/or integrated signal 480.

In some examples, P-wave detector 262 is configured to determine the maximum peak amplitude of the filtered rectified EGM signal 460 in response to a P-wave sensing threshold crossing and compare the maximum peak amplitude to T-wave and/or R-wave sensing thresholds in parallel to applying one or more additional P-wave sensing criteria to the unfiltered EGM signal 450, filtered rectified EGM signal 460, differential signal 470 and/or integrated signal 480.

For example, the differential signal 470 may be determined in parallel to the filtered, rectified EGM signal 460. This differential signal 470 filters the T-wave 476. The P-wave 462 of filtered, rectified EGM signal 460 may cross both a P-wave and T-wave sensing threshold, but only the P-wave 472 of differential signal 470 will cross the P-wave sensing threshold on the differential signal. In this way, a signal that crosses both the P-wave and T-wave sensing thresholds in the filtered, rectified signal 460 can identified as a T-wave if the differential signal 470 does not cross a P-wave sensing threshold and identified as a P-wave if the differential signal 470 does cross a P-wave sensing threshold.

In another example, a slew rate may be determined from unfiltered EGM signal 450 or from differential signal 470 and compared to a P-wave slew rate threshold by analyzer 268 to discriminate a P-wave sensing threshold crossing from a T-wave. The T-wave 476 of differential signal 470 is expected to be significantly attenuated compared to P-wave 472. The high slew rate of the P-wave 472 in differential signal 470 may be a strong discriminator between P-wave 472 and T-waves 476. If the slew rate of raw, unfiltered EGM signal 450 or of differential signal 470, which may be determined using signal sample points before and/or after the P-wave sensing threshold crossing of filtered EGM signal 460, is greater than a P-wave slew rate threshold, the P-wave sensing threshold crossing is confirmed as a sensed P-wave as long as an R-wave sensing threshold is not crossed within a time limit.

The polarity of the differential signal determined from a non-rectified signal may be useful for discriminating P-waves from R-waves in some cases. The P-wave and R-wave may have opposite polarities as shown in raw unfiltered EGM signal 450. When the absolute peak amplitudes and slopes of the P-wave and R-wave approach each other, the P-wave of the differential signal determined from raw unfiltered signal 450 may have a polarity that is distinct from the R-wave.

In another example, the maximum peak amplitude and/or signal width of the integrated signal 480 may be determined after the filtered EGM signal 460 crosses the P-wave sensing threshold. The maximum peak amplitude and/or signal width of the integrated signal 480 may be compared to a maximum P-wave amplitude sensing threshold and/or maximum P-wave signal width sensing threshold. Since the T-wave 486 is increased in amplitude and signal width compared to the P-wave 482 in the integrated signal 480, a maximum peak amplitude and/or signal width of integrated signal 480 that exceeds the respective maximum P-wave amplitude or signal width sensing threshold invalidates the P-wave sensing threshold crossing of the filtered EGM signal as being a true P-wave (and may be used to sense a T-wave 486 or R-wave 484 based on timing relative to an R-sense signal 258).

When the P-wave 452 in the raw unfiltered signal 450 has a low slew rate, the P-wave detector filter 264 may need to be adjusted to a lower low-frequency cut-off, e.g., from 20 Hz to 10 Hz in order to avoid significant attenuation of the P-wave in filtered EGM signal 460. T-wave 466 may be less attenuated in the filtered EGM signal 460 when the filter bandpass is lowered. As a result, T-waves 466 may be oversensed as P-waves due to P-wave sensing threshold crossings by T-waves 466 when the P-wave 462 and T-wave 466 are similar in amplitude. In this situation, the analysis of the differential signal 470 and/or integrated signal 480 may enable identification and discrimination of the P-waves 472 or 482 from T-waves 476 or 486, respectively.

The differential signal 470 and the integrated signal 480 shown or described above need not be determined continuously, but may be determined over a predetermined time interval when the filtered EGM signal 460 crosses the P-wave sensing threshold, e.g., over an interval of approximately 100 ms to 200 ms. The criteria established for detecting and confirming P-waves and distinguishing P-waves from T-waves and R-waves in the methods described herein may be based on particular features of any combination of the unfiltered EGM signal 450 received by P-wave detector analyzer 268, the filtered EGM signal 460, differential signal 470 and/or integrated signal 480, and may include rectified and/or unrectified signals of any of the foregoing signals.

In some examples, the alternate signals, such as differential signal 470 and integrated signal 480, are determined for verifying P-wave sensing during an AV interval on a beat-by-beat or less frequent basis. Additionally or alternatively, one or more alternate signals, e.g., raw unfiltered signal 450 or a differential or integrated signal thereof, differential signal 460 and/or integrated signal 470, are used only during a process for rechecking and establishing P-wave sensing criteria at block 394 of FIG. 7A. A feature, such as a threshold crossing, peak amplitude, slew rate, signal width or other signal feature of the alternate signal at a time of a first P-wave sensing threshold crossing by filtered EGM signal 460 may be compared to the same feature of the alternate signal at the time of the next P-wave sensing threshold crossing by the filtered EGM signal 460 to verify that both events are P-waves or to discriminate one crossing as being a P-wave and one crossing as being a T-wave.

The alternate signal may be used to discriminate the P- and T-waves to enable sensing module 204 (and/or control module 206) to establish P-wave sensing criteria based only on filtered EGM signal 460 or any combination of the filtered EGM signal 460 and/or one or more alternate signal as listed above. Established P-wave sensing criteria may then be applied to the filtered EGM signal 460 (and/or alternate EGM signal) during P-wave sensing for atrial-ventricular synchronous pacing without requiring beat-to-beat determination of a differential and/or integrated signal.

Figure 8:
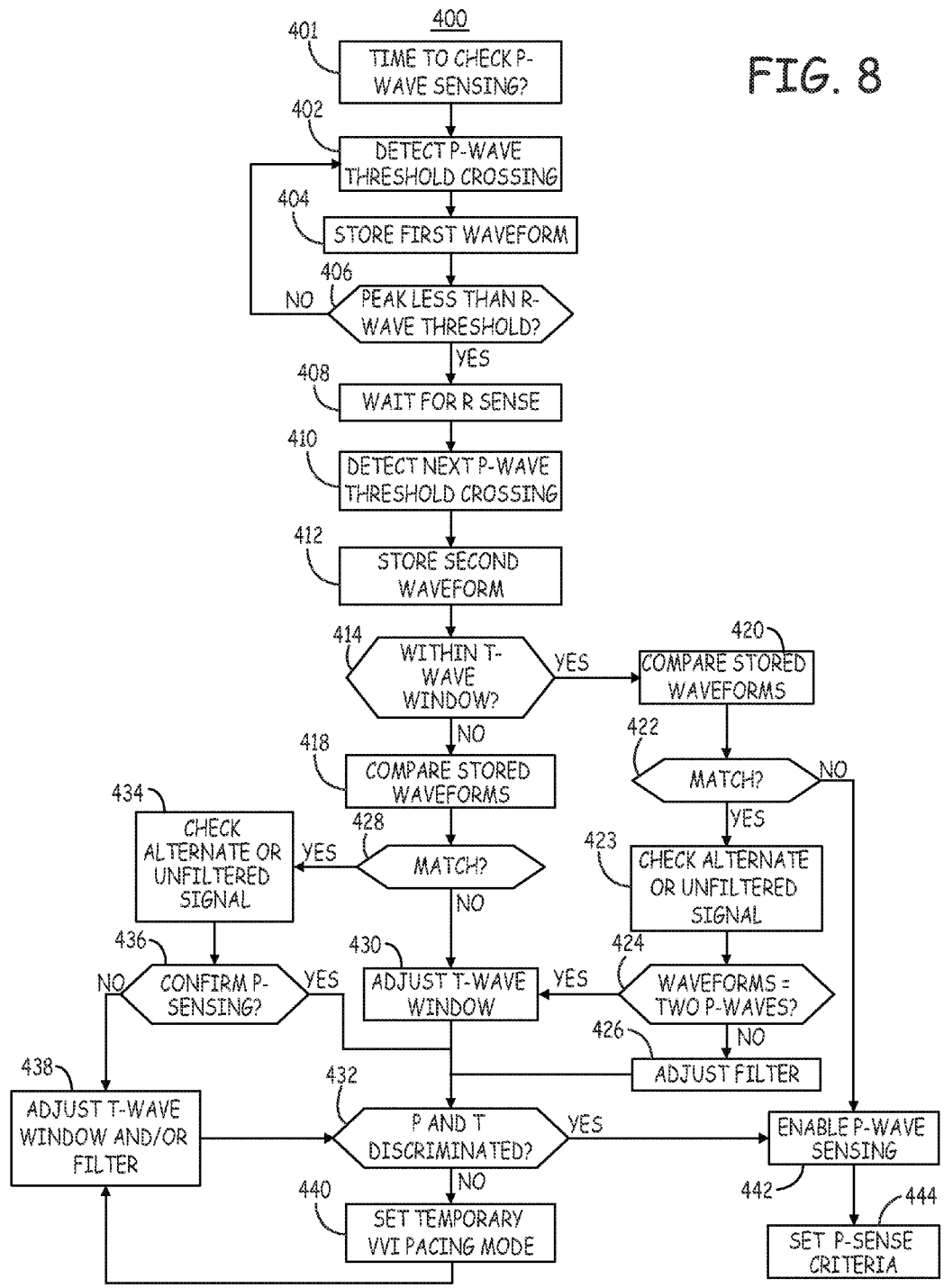
FIG. 8 is a flow chart of a method for establishing and re-checking P-wave sensing criteria by the RV pacemaker.

FIG. 8 is a flow chart 400 of a method for establishing and updating P-wave sensing criteria. The process shown in FIG. 8 may be performed by sensing module 204 and/or control module 206, e.g., by executing instructions stored in memory 210. In the techniques described in conjunction with FIG. 8 and other flow charts presented herein, analysis of the filtered EGM signal, an unfiltered EGM signal, and/or alternate EGM signal and adjustments made to the P-wave detector filter 264 and/or a T-wave sensing window based on the analysis may be executed by sensing module 204, under the control of control module 206 in some examples, or cooperatively by sensing module 204 and control module 206.

At block 401, the control module 206 determines if it is time to check P-wave sensing to verify reliable P-wave sensing and update P-wave sensing criteria if needed. The process may be started at block 401 manually any time using external device 20, automatically upon initial implantation of the RV pacemaker 14, and/or repeated automatically on a scheduled periodic basis. In other examples, the process is performed after a P-wave has not been verified for a predetermined time interval as described in conjunction with FIG. 7. In still other examples, control module 206 determines that a re-check is needed at block 401 in response to detecting a posture change, a change in patient activity level, a change in heart rate, a change between sustained R-wave sensing and sustained ventricular pacing or other change or condition that may alter the amplitude or morphology of the P-wave signal, which may be detected using sensors 212.

When control module 206 determines that it is time to check P-wave sensing, sensing module 204 starts the process of checking P-wave sensing by detecting a crossing of the P-wave sensing threshold by the filtered EGM signal 266 at block 402. The P-wave sensing threshold detected at block 402 is a non-blanking, non-refractory sensing threshold crossing and may be required to be outside a T-wave window. A first waveform of the filtered EGM signal 266 is stored over a first analysis window at block 404 in response to the threshold crossing. For example, the first analysis window may be started at the P-wave sensing threshold crossing, or a predetermined interval or number of sample points prior to the sensing threshold crossing, and extend a predetermined interval or number of sample points after the sensing threshold crossing. A maximum peak amplitude or peak-to-peak amplitude difference during the analysis window is compared to an R-wave threshold at block 406. If the peak amplitude or peak-to-peak difference reaches an R-wave threshold, the crossing of the P-wave sensing threshold is evidence of an R-wave instead of a P-wave. The process returns to block 402 to wait for the next P-wave sensing threshold crossing.

If the peak amplitude or peak-to-peak amplitude difference is less than the R-wave threshold at block 406, the sensing module 204 waits for the next R-sense signal 258 (or a ventricular pacing pulse when an R-sense signal is not received) at block 408. The P-wave threshold crossing at block 402 may be a P-wave or a T-wave but is presumed not to be an R-wave. After the next R-sense signal 258 (or ventricular pacing pulse), the next P-wave sensing threshold crossing is detected at block 410.

In the example shown, an analysis of the EGM signal is performed to check P-wave sensing criteria regardless of whether a T-wave sensing threshold is crossed. In some cases, a T-wave sensing threshold is not being used. In other examples, if a T-wave sensing threshold has been established that is greater than the P-wave sensing threshold, the P-wave detector 262 may set a time limit to determine if the T-wave sensing threshold is crossed within the time limit after the P-wave sensing threshold crossing at block 410. Checking of the P-wave sensing criteria may not be required as long as the EGM signal does not cross the T-wave sensing threshold during the first analysis window but does cross the T-wave sensing threshold within the time limit following the next P-wave sensing threshold crossing after the R-sense signal. The P-wave before the R-sense signal and the T-wave after the R-sense signal are discriminated based on amplitude. The control module may return to the process shown in FIG. 6 for controlling ventricular pacing using far-field P-wave sensing.

In other examples, the P-wave sensing criteria are checked by continuing to block 412 after detecting the next P-wave sensing threshold crossing at block 410 after the R-sense signal. At block 412, a second waveform of the filtered EGM signal 266 is stored over a second analysis window in response to the next P-wave sensing threshold crossing. The second analysis window may be analogous to the first analysis window in timing and duration. In this way, the P-wave detector analyzer 268 acquires a waveform of a sensed signal occurring before an R-sense signal and a waveform of a sensed signal after the R-sense signal. Further analysis of these waveforms will reveal whether P-waves are being properly sensed and discriminated from T-waves.

P-wave detector 262 determines if the next crossing of the P-wave sensing threshold detected at block 410 occurred within a T-wave sensing window after the R-sense signal at block 414. A T-wave sensing window may be defined to extend from the R-sense signal (or a ventricular pacing pulse) to a time point after the R-sense signal so that it is expected to encompass the T-wave but terminate prior to the next anticipated P-wave. The T-wave sensing window may be started when an R-wave sensing threshold crossing is detected by R-wave detector 252 or upon receiving the R-sense signal 258 by P-wave detector 262. The T-wave sensing window may also be started in response to delivering a ventricular pacing pulse when an R-wave is not sensed at block 408. The T-wave sensing window may be set to different intervals depending on the ventricular rate and depending on whether the initiating event is an R-sense signal or a ventricular pacing pulse.

If the next P-wave threshold crossing detected at block 410 is within a T-wave sensing window, as determined at block 414, the first and second waveforms stored during the first analysis window and the second analysis window are compared at block 420. The comparison made at block 420 may include a sample-by-sample morphology comparison of the two waveforms, wavelet morphology comparison, and/or determining one or more analogous features of the stored waveforms and comparing the analogous features to each other. Analogous features that may be determined and compared include, but are not limited to, peak amplitude, peak slope, signal width, number of peaks, a time interval from the P-wave sensing threshold crossing to a signal peak, time interval from the threshold crossing to a peak positive slope, time interval from the threshold crossing to a peak negative slope, time interval from the threshold crossing to another fiducial point or other time intervals between other fiducial points.

The two waveforms may be determined to match each other at block 422 if each comparison made at block 420 results in a difference that is less than predetermined matching criteria, e.g., a difference of less than 20% between each feature being compared. The particular matching criteria or matching thresholds used will depend on the morphology or feature comparisons being made.

If the two waveforms do not match as determined at block 422, based on at least one or more features not meeting the matching criteria, the first waveform preceding the R-sense signal is assumed to be a P-wave and the second waveform falling into the T-wave sensing window and not matching the first waveform is assumed to be a T-wave. The P-wave is distinguishable from the T-wave following the R-sense signal based on both time and morphology indicating reliable P-wave sensing and discrimination from T-waves.

P-wave sensing is enabled at block 442. P-wave sensing criteria are set at block 444 by sensing module 204 based on the one or more features determined to be distinct during the comparison of the first and second waveforms at block 420. For example, a threshold or range may be defined that is characteristic and inclusive of a given P-wave feature and exclusive of the analogous T-wave feature. To illustrate, a maximum P-wave signal width threshold may be defined as being 30 ms based on a measured P-wave signal width of 20 ms and a measured T-wave signal width of 40 ms during the comparison made at block 420. It is recognized that comparisons may be made between multiple P-waves and multiple T-waves to improve the confidence of P-wave sensing criteria set at block 444. The P-wave sensing criteria set at block 444 may be the same criteria previously used if the same criteria still discriminate well between P-waves and T-waves. Alternatively, the criteria set at block 444 may be new criteria established by sensing module 204 in response to the comparing performed at block 420 and based on differences identified during the comparing.

The "no" branch of block 422 as just described represents the situation of the P-wave and the T-wave being reliably distinguished based on the comparison of the first and second waveforms not matching and the second waveform falling in the T-wave sensing window. In other cases, the second threshold crossing may be outside the T-wave sensing window and/or the first and second waveforms may match. In these cases, both waveforms may be a P-wave (e.g., if the T-wave has been well-filtered from the EGM signal), both waveforms may be T-waves, or one waveform may be a P-wave and one a T-wave but indistinguishable from each other based on the current filtering and T-wave sensing window settings. The other branches of flow chart 400 handle these other situations as will now be described.

If the next P-wave threshold crossing detected at block 410 is within the T-wave sensing window ("yes" branch of block 414) but the two waveforms match at block 422, both waveforms could be P-waves. Alternatively, one may be a P-wave and one may be a T-wave but they are indistinct from each other in the filtered EGM signal 266. P-wave sensing by P-wave detector 262 may be unreliable under the current conditions for use in setting AV pacing escape intervals. Accordingly, to determine if both waveforms are P-waves or one is a P-wave and one is a T-wave, the raw, unfiltered EGM signal 265 (or an alternate filtered EGM signal 267) is analyzed at block 423 to determine if T-waves are present in the unfiltered EGM signal and are not present in the filtered EGM signal 266. Peak amplitudes, morphology, timing relative to an R-sense signal or other features may be used to identify T-waves present in the alternate filtered EGM signal 267 or unfiltered EGM signal 265.

If T-waves are identified in the alternate or unfiltered EGM signal that are not present in the filtered EGM signal 266, e.g., not coinciding or occurring at approximately the same time after an R-sense signal as one of the first or next P-wave sensing threshold crossings detected at blocks 402 and 410, P-wave sensing is confirmed at block 424. Both the first waveform and the second waveform are determined to be P-waves when T-waves can be identified from the unfiltered EGM signal 265 (or an alternate filtered EGM signal 267) and are not present in the filtered EGM signal 266 from which the first and second waveforms were obtained and not coinciding with either of the first or second waveforms. The T-wave is optimally filtered from the filtered EGM signal 266. P-wave sensing is deemed reliable, however the T-wave sensing window may be adjusted at block 430 by sensing module 204 so that the second waveform that is actually a P-wave does not fall in the T-wave sensing window. For example, the T-wave sensing window may be shortened at block 430. P-waves are determined to be reliably discriminated from T-waves at block 432 based at least on the effective filtering of the T-wave from the filtered EGM signal 266 and may be further discriminated based on timing by adjusting the T-wave sensing window at block 430. P-wave sensing is enabled at block 442 for use in synchronizing ventricular pacing with P-sense signals 272 using a target AV interval. P-wave sensing criteria are set at block 444 by sensing module 204 based on the P-wave features determined at block 420. These criteria may be used for confirming a P-wave during an AV interval started in response to a P-wave threshold crossing. Setting P-wave sensing criteria may include setting the P-wave sensing threshold based on an amplitude of the stored first and second waveforms.

The "yes" branch of block 424 just described is the situation that both of the first and second waveforms before and after the R-sense signal are P-waves, but the second P-wave is within the T-wave sensing window. This situation may be corrected by adjusting the T-wave sensing window. T-waves are being properly filtered so filter adjustment is not required.

The "no" branch of block 424, however, addresses the situation where the second waveform is a T-wave that occurs within the properly set T-wave window but the T-wave and the P-wave morphologies are too similar to be distinguishable based on waveform comparisons. In this case, the T-wave sensing window does not require adjusting, but adjustment of the P-wave detector filter 264 by sensing module 204 may provide greater discrimination between the P- and T-wave morphologies.

If T-waves are present in the unfiltered or alternate filtered EGM signal 265 or 267 and correspond in time to the second waveform of the filtered EGM signal 266 as determined at block 423, the two P-wave sensing threshold crossings of the filtered EGM signal 266 are not both P-waves ("no" branch of block 424). In response to not confirming both waveforms as being P-waves, the bandpass of filter 264 may be adjusted to alter the waveform of the T-wave at block 426. As described above, the center frequency and/or bandpass of filter 264 may be adjusted to intentionally increase the amplitude of the T-wave, decrease the amplitude of the T-wave, or otherwise modify the T-wave morphology to make the P-wave and T-wave distinct based on amplitude and/or waveform comparisons. Multiple filter adjustments may be made until a comparison of the P-wave and T-wave amplitudes, signal widths and/or other morphology feature(s) results in non-matching waveforms.

After filter adjustments, P-wave and T-wave discrimination is confirmed at block 432. The P-wave and T-wave were already discriminated based on the properly set T-wave sensing window so the result at block 432 will be "yes" based on this time distinction alone. However, if the adjusted filter frequency range provides further discrimination based on morphology or amplitude, independent of the timing of the T-wave sensing window, the adjusted filter center frequency and bandwidth is selected by the P-wave detector 262 for sensing P-waves for use in controlling escape intervals.

P-wave and T-wave discrimination determined at block 432 after filter adjustment may include elimination or significant attenuation of the T-wave, such that it no longer crosses the P-wave sensing threshold, or an increased T-wave amplitude that crosses a higher, T-wave sensing threshold. As such, filter adjustment may provide amplitude discrimination in addition to the timing discrimination provided by the T-wave sensing window.

Additionally or alternatively, the T-wave may be altered enough by a bandpass filter adjustment that the P-wave and T-wave waveforms are distinguishable based on morphology, slope or other waveform features other than peak amplitude. Filter adjustment may therefore provide morphology discrimination based on the overall wave shape or other signal features other than peak amplitude.

As long as at least one of the timing, peak amplitude, and waveform morphology provide P-wave and T-wave discrimination as determined at block 432, P-wave sensing may be enabled at block 442 for setting AV pacing escape intervals. The discriminatory features identified at bock 432 after filter adjustment may be used at block 444 to set P-wave sensing criteria that are used during AV intervals for confirming that a P-wave threshold crossing is a P-wave (e.g., for confirming a sensed P-wave at block 384 of FIG. 7).

Adjustment of the T-wave sensing window or the P-wave detector filter by sensing module 206 have now been described for addressing the situation of the second waveform being a P-wave but improperly falling into the T-wave sensing window ("yes" branch of block 424 leading to T-wave sensing window adjustment at block 430) and for the situation of the second waveform being a T-wave and properly falling into the T-wave sensing window) but having an indistinct morphology from the P-wave ("no" branch of block 424 leading to P-wave detector filter adjustment at block 426). Now techniques will be described that deal with the situation of the second waveform not falling into the T-wave sensing window, whether it is a true T-wave or not.

If the second waveform is not within the T-wave sensing window, "no" branch of block 414, the first and second waveforms are compared at block 418. If the waveforms do not match ("no" branch of block 428), the second waveform may be a T-wave, but the T-wave sensing window may need adjusting. The non-matching waveforms indicate that the P-wave detector filter 264 does not necessarily need adjusting since the waveforms are distinguishable based on the morphology. The T-wave sensing window may need to be adjusted at block 430, however, because the Q-T interval of the EGM signal may change over time, e.g., due to changes in heart rate, change in disease state or other factors. For example, the T-wave sensing window may be shortened by approximately 20 ms for every increase in heart rate of 10 beats per minute. The T-wave window may be adjusted by sensing module 204 at block 430 so that it would encompass the second waveform. A different T-wave window may be set when a ventricular pacing pulse is delivered than when an R-sense signal is received to account for differences in the Q-T interval on paced beats compared to intrinsic beats.

Since the first and second waveforms do not match based on the morphology comparison at block 428, discrimination of the P-waves and T-waves is confirmed at block 432. The T-wave sensing window adjustment may provide additional discrimination of the P-waves and T-waves based on timing. P-wave sensing for controlling pacing escape intervals is enabled by control module 206 at block 442. The P-wave sensing criteria may be adjusted at block 444 by sensing module 204 as needed based on the waveform features determined and compared at block 418.

Baseline P-wave and T-wave amplitude measurements and baseline T-P interval measurements may be determined and stored at block 444 after setting the P-sense criteria. As described in conjunction with FIG. 10A, the control module 206 may be configured in some examples to monitor an amplitude difference between P-wave and T-waves and/or a T-P interval to detect when the P-waves and T-waves are approaching each other in either amplitude or time. A baseline amplitude difference and/or a baseline T-P interval may be established at block 444 for use by control module 206 in detecting a decrease in either the amplitude difference or the T-P interval.

If the second waveform is not within the T-wave sensing window ("no" branch of block 414) and the first and second waveforms do match ("yes" branch of block 428), the waveforms could be two P-waves, two T-waves or a P-wave and a T-wave that are indistinct from each other. In this situation, an analysis of the unfiltered signal 265 or an alternate filtered signal 267 is performed at block 434 to determine if T-waves can be identified from the unfiltered signal 255 or alternate filtered signal 257 and whether they coincide in time with the first or next P-wave sensing threshold crossings detected at blocks 402 and 410, respectively. In other examples, the alternate signal analyzed at block 434 to identify a T-wave coinciding in time with the first or next P-wave sensing threshold crossings is an integrated signal, such as signal 480 in FIG. 7B, in which the T-wave 486 is enhanced compared to the T-wave 466 in the filtered EGM signal 460. A T-wave identified from the unfiltered signal 255, alternate filtered signal 257, or an integrated signal (of the filtered signal 266 or unfiltered signal 265) may be determined to coincide in time with the first or next P-wave sensing threshold crossings when the identified T-wave occurs within a predetermined interval of time from the P-wave sensing threshold crossing.

In some cases, a T-wave may not be readily identified from the unfiltered EGM signal 265. Filter 264 may be adjusted to increase the T-wave amplitude in an alternative filtered EGM signal 267. Multiple filter adjustments may be performed until a T-wave can be identified. For example up to six different center frequency and bandwidth combinations may be tested to determine if the T-wave can be identified from the alternate filtered EGM signal 267. Sensing module 202 may determine if T-waves can be identified within a maximum number of filter adjustments in some examples.

If a T-wave is identified from the unfiltered signal 265 or alternate filtered EGM signal 267 but is not identified from the filtered EGM signal 266 at approximately the same time, the P-wave detector filter 264 is optimally filtering T-waves from the filtered EGM signal 266. P-wave sensing is confirmed at block 436 in response to identifying T-waves from the unfiltered EGM signal 265 (or alternate filtered EGM signal 267) that are absent from the filtered EGM signal 266. Both of the P-wave sensing threshold crossings of the filtered EGM signal 266 are P-waves that match each other morphologically and both are properly detected outside the T-wave sensing window. No adjustment of the T-wave sensing window or the P-wave detector filter 264 is needed. Confirmation is made that P-waves are being properly sensed and discriminated from T-waves at block 432.

If T-waves can be identified and correspond in time to one or both of the first and next P-wave sensing threshold crossings of the filtered EGM signal 266, adjustment of the T-wave sensing window and/or the P-wave detector filter 264 is required to improve P-wave and T-wave discrimination based on at least one of timing, amplitude or morphology. If T-waves can be identified, and correspond in time to one or both P-wave sensing threshold crossings, T-waves are not being optimally filtered from the EGM signal and are confounding P-wave sensing. Sensing module 204 adjusts at least one of the T-wave sensing window and/or the P-wave detector filter 264 at block 438 to improve separation and discrimination of P-waves and T-waves.

In some cases, T-waves and P-waves may not be distinguished from each other based on comparisons made between the first and second waveforms of the filtered EGM signal 266 at block 418 or based on analysis of the unfiltered signal 265 or alternate EGM signal 267 at block 434 such that P-wave sensing cannot be confirmed at block 436. Adjustment of the T-wave sensing window may be performed at block 438 to improve separation of the signals, but in some cases T-wave sensing window adjustment may not improve discrimination between T-waves and P-waves. The T-wave and P-wave may be overlapping, particularly if the heart rate is elevated from a resting heart rate. The P-wave detector filter 264 may be adjusted at block 438 to improve the P-wave signal strength, diminish the T-wave signal strength or intentionally increase the T-wave amplitude to be greater than the P-wave amplitude in the filtered EGM signal 266. Adjustment to the P-wave detector filter 264 and/or T-wave sensing window are performed at block 438 so that P- and T-waves can be discriminated at block 432.

At block 438 (and block 426), adjustment to the P-wave detector filter 264 for increasing amplitude, waveform or timing separation of the P-wave and T-wave in the filtered EGM signal 266 may include adjustment of the center frequency and/or the bandpass width. For example, the filter may be adjusted to a bandpass centered on the T-wave frequency to intentionally increase T-wave amplitude but with a wide enough bandpass that includes P-waves, or centered on the P-wave frequency to increase P-wave amplitude with a narrow bandwidth that eliminates T-waves. The bandpass may be symmetrical or asymmetrical to intentionally increase signal strength of P-waves relative to T-waves or vice versa.

The center frequency may be selected in the range of 10 Hz to 50 Hz with a bandwidth including frequencies in the range of 5 Hz up to 70 Hz in some examples. The bandwidth may be relatively narrow or wide, e.g., a total bandwidth of up to 50 Hz or as narrow as 10 Hz. For example, filter 264 may initially be adjusted to a center frequency of 20 Hz with a symmetrical 30 Hz bandpass width for a total 3 dB range of 5 Hz to 35 Hz to maximize the P-wave amplitude. If the T-wave is indistinct from the P-wave using this filtering, the filter center frequency may be adjusted lower or higher, the bandpass width may be increased or decreased, and/or the bandpass may be shifted to an asymmetrical bandpass that has a greater range less than the center frequency or a greater range higher than the center frequency. For example, the filter 264 may be shifted to a center frequency of 25 Hz with a narrow bandpass width of 20 Hz for a total 3 dB range of 15 Hz to 35 Hz to remove or attenuate a lower frequency T-wave from the filtered EGM signal 266. In some examples, the P-wave may be a narrow signal having a higher than normal frequency, so that filter 264 may be adjusted to a 40 Hz center frequency in this situation with a relatively narrow bandwidth. In some instances, the center frequency of P-wave detector filter 264 is selected to include both P-waves and R-waves within the filter bandpass. In other instances, the P-wave detector center frequency may be centered on an expected P-wave frequency.

Once the P-wave detector filter 264 is adjusted to achieve P- and T-wave discrimination at block 432 based on amplitude, time, or other morphology features in the filtered EGM signal 266, which may include repeated adjustments of filter 264 until an optimal center frequency and bandpass is identified for separating P-wave and T-wave signals, P-wave sensing may be enabled at block 442. The P-wave sensing criteria may be set at block 444 based on the discrimination achieved by filter adjustments. After adjusting the P-wave detector filter 264, the P-wave signal may be altered. As such, the P-wave signal features used to define the P-wave sensing criteria may be re-determined, compared to analogous T-wave features and used to establish P-wave sensing criteria at block 444.

In some cases, reliable discrimination of P-waves and T-waves will not be achieved at block 432, despite multiple filter adjustments and/or one or more T-wave sensing window adjustments. If this occurs, the RV pacemaker 14 may be set to a temporary VVI pacing mode at block 440 by control module 206 in which P-wave sensing is disabled for use in setting AV pacing escape intervals. The control module 206 controls ventricular pacing pulse delivery by the pulse generator 202 in a single chamber ventricular pacing and sensing mode (i.e., a VVI mode) where VV escape intervals are set in response to R-sense signals 258 and ventricular pacing pulses. An R-sense signal 258 during a VV escape interval inhibits a scheduled pacing pulse and restarts the VV escape interval. P-wave detector 262 is either disabled by control module 206 or P-sense signals 272 produced by P-wave detector 262 are ignored by pace timing and control module 270 for setting ventricular pacing escape intervals.

The VVI pacing mode set at block 440 may be temporary. Periodically, the sensing module 204 may return to block 438 to adjust the T-wave window and/or P-wave detector filter 264 to achieve reliable discrimination of P-waves and T-waves based on amplitude, timing and/or morphology. For example, the sensing module 204 may return to block 438 every 10 seconds, every 30 seconds, every one minute, or other predetermined time interval to attempt adjustments to separate the P-waves and T-waves. If reliable discrimination is achieved (block 432), the control module 206 switches from the temporary VVI pacing mode back to an atrial synchronized ventricular pacing mode in which P-wave sensing is enabled at block 442, and the P-wave sensing criteria are updated by sensing module 204 as needed at block 444. The pace timing and control module 270 of control module 206 sets ventricular pacing escape intervals to AV pacing escape intervals in response to P-sense signals 272 for controlling ventricular pacing pulse delivery by pulse generator 202.

Figure 9:
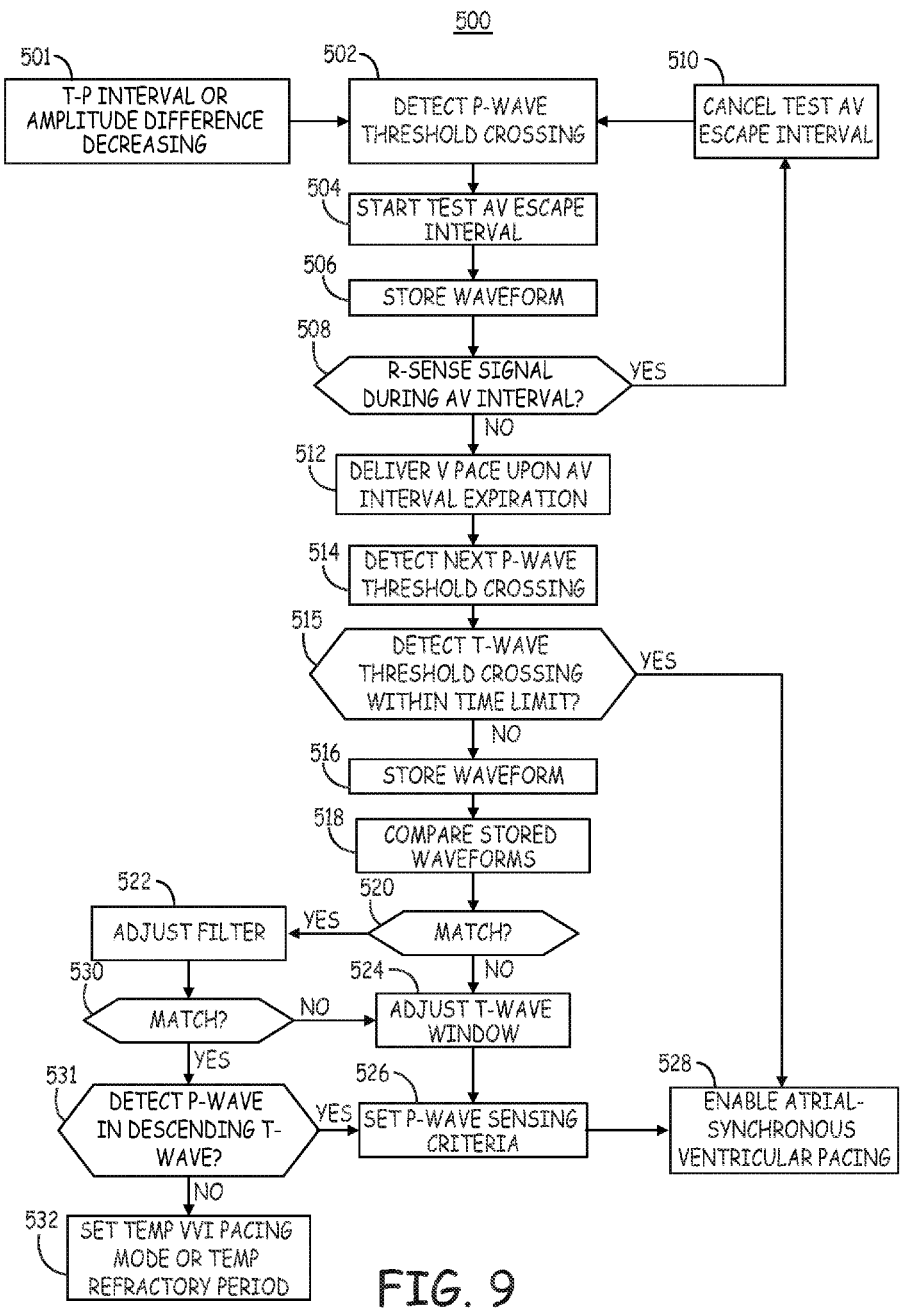
FIG. 9 is a flow chart of a method for establishing P-wave sensing criteria by the RV pacemaker according to one example.

FIG. 9 is a flow chart 500 of a method for controlling P-wave sensing and ventricular pacing by RV pacemaker 14 according to another example. The techniques shown in flow chart 500 may be performed as needed for establishing P-wave sensing criteria by sensing module 202. The techniques of flow chart 500 may be performed for confirming P-wave and T-wave discrimination, e.g., at block 432 of FIG. 8, or during adjustments to the T-wave sensing window or the P-wave detector filter 264 for improving discrimination between P-waves and T-waves. In particular, the techniques of flow chart 500 may be performed when the T-wave and P-wave are determined to be indistinct during R-wave sensing by sensing module 204. The method of flow chart 500 and other flow charts presented herein for setting P-wave sensing criteria and controlling ventricular pacing using sensed P-waves may be performed cooperatively by sensing module 204 and control module 206.

At block 502, the P-wave detector 262 detects a P-wave sensing threshold crossing. A test AV escape interval is started at block 504 in response to the P-wave sensing threshold crossing as long as the EGM signal does not reach the R-wave sensing threshold (or an intermediate T-wave sensing threshold if used) during the time limit (310 in FIG. 5A). The EGM signal waveform associated with the P-wave sensing threshold crossing is stored over an analysis window at block 506. The test AV escape interval set at block 504 may be a shorter interval than a targeted AV interval that is used by the pace timing and control module 270 during bradycardia or rate responsive pacing. The shorter interval is used in order to promote ventricular pacing pulse delivery prior to an intrinsic R-wave during the process of flow chart 500. For example, the AV interval may be shortened by 100 ms. Shortening of the AV interval also promotes temporal separation of the P-wave and the T-wave for facilitating discrimination and analysis of the two separate waveforms.

During the test AV interval, the EGM signal is monitored for an R-wave sensing threshold crossing by R-wave detector 252 at block 508. If the P-wave sensing threshold crossing detected at block 502 is followed by an R-sense signal at block 508 during the test AV interval, the test AV escape interval is cancelled at block 510.

If a V-sense signal does not occur during the AV interval, the test AV interval expires, and a ventricular pacing pulse is delivered at block 512. After delivering the ventricular pacing pulse, the next P-wave sensing threshold crossing is detected at block 514 (outside any relevant ventricular blanking period after the ventricular pacing pulse which may be set to include the pacing-evoked R-wave). In the method shown by flow chart 500, a waveform crossing the P-wave sensing threshold stored prior to the ventricular pacing pulse is expected to be a P-wave and the first waveform crossing the P-wave sensing threshold after the ventricular blanking period is expected to be a T-wave. As such, a comparative analysis of a pre-pace waveform and a post-pace waveform enables P-wave sensing criteria to be established that discriminate P-waves from T-waves.

If a T-wave sensing threshold crossing occurs within the time limit from the second P-wave sensing threshold crossing, as determined at block 515, the T-wave of the pacing evoked response is distinct from the P-wave based on T-wave amplitude. Atrial-synchronous ventricular pacing is enabled at block 528. No further adjustment may be needed to reliably discriminate between P-waves and T-waves.

If a T-wave sensing threshold crossing does not occur within the time limit, the P-wave and pacing-evoked T-wave may be indistinct. Further analysis is required to determine if reliable P-wave and T-wave discrimination can be achieved. The EGM signal is stored during an analysis window at block 516. The analysis windows set at blocks 506 and 516 for storing the EGM signal waveform after a P-wave sensing threshold crossing may be equal in duration and may begin and end at the same times relative to the respective P-wave sensing threshold crossings, which may include buffered sample points stored prior to the P-wave sensing threshold crossing.

The stored waveforms are compared at block 518 by performing a morphology comparison of the overall waveform of all the signal sample points during the analysis window and/or by determining and comparing specific analogous features of the waveforms during the analysis window, such as peak amplitude, signal width, slope etc. If the waveforms do not match, as determined at block 520, the P-waves and T-waves are determined to be distinguishable.

A T-wave sensing window is adjusted as necessary at block 524 based on the timing of the P-wave sensing threshold crossing at block 514 and/or determining the timing of the T-wave sensing threshold crossing during the analysis window of the post-pace (second) stored waveform. The T-wave sensing window may be lengthened, shortened, or shifted in time relative to the ventricular pacing pulse to promote a high likelihood of the second P-wave sensing threshold crossing occurring during the T-wave sensing window following pacing pulses and intrinsic R-waves. It is recognized that the Q-T interval following a pacing pulse may be different than the Q-T interval during an intrinsic ventricular beat. As such, the T-wave sensing window may be set to account for this difference.

At block 526, P-wave sensing criteria are set by sensing module 204 based on the comparison performed at block 518. One or more features may be identified that have the greatest difference between the pre-pace waveform (P-wave) and the post-pace waveform (T-wave). The greatest difference may be identified as a greatest percentage difference or a greatest normalized difference. The P-wave sensing criteria may be set to include a threshold or range that includes the P-wave value for a feature having a greatest difference and excludes the analogous T-wave feature value. The difference between the overall morphologies of the waveform as defined by all of the equally spaced sample points across the analysis windows may be used to set a threshold percentage difference between the P-wave and T-wave morphology for discriminating between P-waves and T-waves.

The T-wave sensing window and the P-wave sensing criteria set at blocks 524 and 526, respectively, may be stored in memory 210 and used by P-wave detector 262 for confirming P-waves during AV escape intervals set in response to detecting P-wave sensing threshold crossings. The P-wave sensing threshold may be included in the P-wave sensing criteria set at block 526. The P-wave sensing threshold may be set as a percentage of the peak amplitude of the waveform stored at block 506. The T-wave sensing threshold may additionally or alternatively be set at block 526 by sensing module 204 based on the amplitude of the post-pace stored waveform and/or a difference between the peak amplitude of the first, pre-pace stored waveform (block 404) and the second, post-pace stored waveform (block 412).

If the two waveforms match at block 520, the T-wave arising from the evoked response to the ventricular pacing pulse may be indistinguishable from the P-wave sensed prior to the ventricular pacing pulse. In this case, P-wave sensing may not be reliable for use in controlling ventricular pacing. The P-wave detector filter 264 may be adjusted at block 522 until the pre-pace P-wave and the post-pace T-wave no longer have matching morphologies as determined at block 530. The process of adjusting the filter may include multiple iterations of adjusting the center frequency and/or bandpass, collecting waveforms of the P-wave and the post-pace T-wave, and comparing the waveforms. In some cases, an analysis of the P-wave frequency or signal width and/or an analysis of the T-wave frequency or signal width may be performed to guide the filter adjustment to reduce the number of times adjustments are made until successful P-wave and T-wave discrimination is made. In other examples, a set of predefined combinations of center frequency and bandpass width may be defined and tested at block 522 until a combination corresponding to a maximum difference in amplitude, signal width or other feature of the P-wave and T-wave is identified.

If successful P-wave and T-wave discrimination is achieved by adjusting the filter properties, based on non-matching waveforms as determined at block 530, the T-wave sensing window may be adjusted at block 524 to include the T-wave. P-wave sensing criteria are set at block 526 based on the features determined from the P-wave and T-wave of the EGM signal after filter adjustments. Atrial-synchronous ventricular pacing is enabled at block 528.

In some cases, filter adjustments may not successfully yield a distinct P-wave and T-wave. The P-wave, however, may cause an inflection point in the descending portion of the T-wave when the P-wave is overlapping the T-wave. An inflection point in the descending portion of the T-wave may be identified as the P-wave in some examples. A P-wave inflection point may be identified based on previously stored T-wave morphology at lower heart rates. The matching waveform comprising indistinct T- and P-waves may be compared to the previously stored T-wave morphology. In one example, the number of inflection points of the T-wave occurring after a maximum peak T-wave of the filtered cardiac signal is stored. During any of the processes disclosed herein, when P-waves and T-waves are determined to be indistinct in a filtered or unfiltered cardiac signal based on time, amplitude or separate P-wave and T-wave morphologies, identifying a P-wave inflection point along a descending portion of the T-wave can be performed for discriminating the P-wave from the T-wave and establishing P-wave sensing criteria.

If a new inflection point can be identified in the descending portion of the T-wave at block 531 that was not present in the T-wave at a lower heart rate, this new inflection point may be evidence of the P-wave and used for setting P-wave sensing criteria at block 526 during high heart rates associated with overlapping P- and T-waves. Atrial-synchronized ventricular pacing may be enabled at block 528 based on the ability to sense a P-wave inflection in the descending portion of the T-wave.

If the filter adjustments do not successfully yield a distinct P-wave and T-wave and a P-wave inflection along the descending portion of the T-wave cannot be identified, the control module 206 sets the pacing mode of the RV pacemaker 14 to a temporary single chamber ventricular pacing mode (VVI) that does not set AV pacing escape intervals using P-wave sensing at block 532. Alternatively, the control module 206 may set a temporary refractory period that encompasses an overlapping T-wave and P-wave so that the overlapping events occurring within the refractory period are both ignored for the purposes of setting an AV pacing escape interval.

A relatively short test AV interval set at block 504 promotes temporal separation of the P-wave and the T-wave since the R-wave and subsequent T-wave will both occur earlier when the test AV interval is shortened. In some examples, the test AV interval may be shortened at block 504 if the P-wave and T-wave are indistinct based on amplitude, time, and/or morphology. Before setting a temporary VVI (or VVIR) mode at block 531, all or a portion of the flow chart of FIG. 9 may be performed with a shortened AV test interval to determine if the P-wave and T-wave are distinct.

An interval between a ventricular pacing pulse and the P-wave sensing threshold crossing can be measured when different test AV escape intervals are applied. As described below in conjunction with FIG. 12, modulating the timing of a ventricular pacing pulse, e.g., by modulating the test AV escape interval, causes the interval between the ventricular pacing pulse and the next P-wave sensing threshold crossing to change when the P-wave sensing threshold crossing is a true P-wave. This interval will not change, however, when the P-wave sensing threshold crossing is a T-wave during a stable heart rate. As such, in some examples, all or a portion of FIG. 9 may be repeated using different test AV pacing escape intervals to separate the P-wave and T-wave for use in establishing P-wave sensing criteria and enabling atrial-synchronous ventricular pacing. If the P-wave sensing threshold crossing after the ventricular pacing pulse is verified as a P-wave based on an altered interval from the ventricular pacing pulse to the P-wave sensing threshold crossing during different test AV escape intervals, atrial-synchronous ventricular pacing may be enabled at block 528.

If the interval to the next P-wave threshold crossing after a ventricular pacing pulse is not altered by modulation of the test AV escape interval, the P-wave threshold crossing detected at block 514 after the ventricular pacing pulse is a T-wave. If amplitude or morphology-based P-wave sensing criteria can be established at block 526 to distinguish the confirmed T-wave from P-waves, atrial-synchronous ventricular pacing can be enabled at block 528. If P-wave sensing criteria cannot be established to distinguish the confirmed T-wave from the P-wave when the AV escape interval is restored to a target AV pacing escape interval, the temporary VVI(R) pacing mode is set at bock 532.

It is recognized that while the process shown in FIG. 9 indicates a single waveform stored at block 506 prior to a ventricular pacing pulse and a single post-pace waveform stored at block 516, the process of collecting pre- and post-pace waveforms may be repeated for multiple pacing cycles to obtain average pre- and post-pace waveforms that are compared at block 518 and/or to obtain multiple differences from comparisons made between multiple pairs of pre- and post-pace waveforms that can be used to determine an average difference.

To illustrate, a pre-pace waveform may be stored at block 506 and a post-pace waveform may be stored at block 516 for a predetermined number of consecutive or non-consecutive ventricular pacing pulses, e.g., three to eight ventricular pacing pulses, delivered at the test AV escape interval. The pre- and post-pace waveforms may be compared for each pacing cycle to determine waveform feature differences. The three waveform features having the greatest differences for all of the paired pre- and post-pace waveforms may be selected as features for discriminating between P-waves and T-waves. The minimum difference determined from all of the comparisons for a selected feature may be used as a basis for setting the P-wave sensing criteria. Examples of waveform features that may be determined include, but are not limited to, signal width, peak amplitude, peak slope, frequency content, and wavelet or Haar transform coefficients.

After establishing the P-wave sensing criteria, the criteria may be verified by testing the criteria against additionally acquired pre- and post-pace waveforms to verify that each of the pre- and post-pace waveforms are correctly confirmed as P-waves and T-waves respectively. After establishing and setting the P-wave sensing criteria at block 526, atrial synchronous ventricular pacing is enabled at block 528. P-wave sensing threshold crossings are used to start AV pacing escape intervals and P-waves confirmed during the AV pacing escape intervals using the P-wave sensing criteria allow the AV pacing escape intervals to time out for triggering ventricular pacing pulse delivery.

Additionally, baseline P-wave and T-wave amplitude measurements and baseline T-P interval measurements may be determined and stored at block 526 after setting the P-sense criteria. As described in conjunction with FIG. 10A, the control module 206 may be configured to use a baseline amplitude difference and/or the baseline T-P interval to detect a decrease in the amplitude difference between P-waves and T-waves or a decrease in the T-P interval.

Figure 10A:
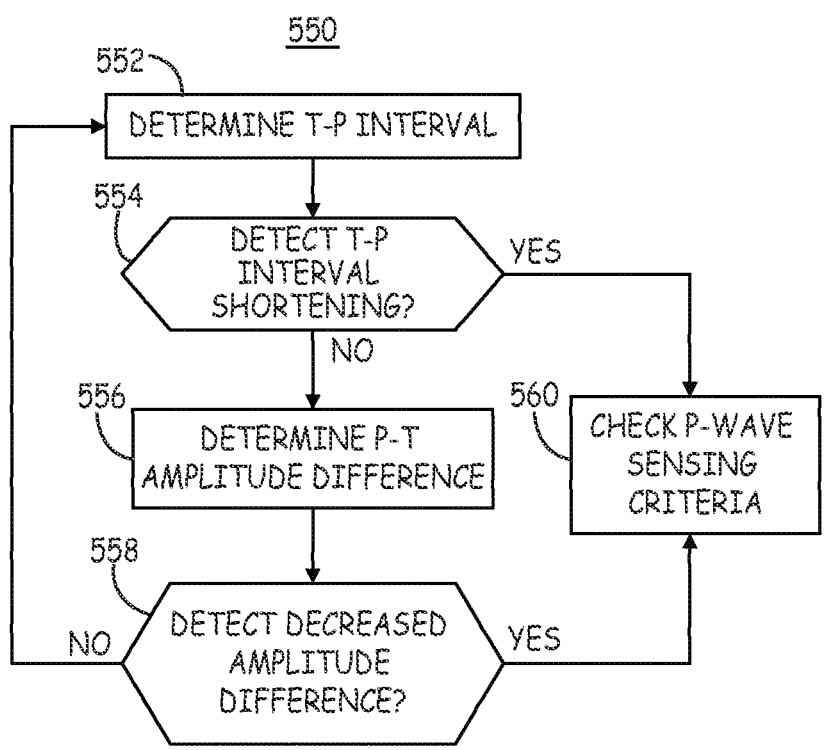
FIG. 10A is a flow chart of a method for determining a need for adjusting P-wave sensing control parameters used by the P-wave detector shown in FIG. 4A.

FIG. 10A is a flow chart 550 of a method for determining a need for adjusting the P-wave detector filter 264 and/or T-wave sensing window. In some examples, control module 206 is configured to determine when the P-wave and T-wave are likely to become indistinguishable before they become indistinguishable. The P-wave and T-wave amplitudes or relative time from each other may change with heart rate, electrode position, patient position, or other factors. Control module 206 may be configured to determine when the T-wave and P-wave are approaching each other in time before they become overlapping and indistinguishable based on time. Control module 206 may additionally or alternatively be configured to determine when the amplitudes of the P-wave and T-wave are approaching each other before they become indistinguishable based on amplitude. In this way, the control module 206 may be enabled to control P-wave detector 262 to adjust filter 264 and/or the T-wave sensing window in advance of the P-wave and the T-wave becoming indistinguishable to maintain reliable P-wave sensing.

At block 552, control module 206 is configured to monitor T-P intervals, i.e., the time interval between the T-wave and the far-field P-wave. For example, a T-P interval may be determined between a cancel P-sense signal 274 produced by P-wave detector 262 (when the R-wave sensing threshold is not crossed within the time limit) and the next P-sense signal 272 (shown in FIG. 4A). As described in conjunction with FIG. 5C, a cancel P-sense signal 274 may be produced in response to a T-wave sensing threshold crossing within time limit 310 of a P-wave sensing threshold crossing. The next EGM signal after a T-wave is expected to be a P-wave. As such, a time interval from the cancel P-sense signal 274 to the next P-sense signal 272 produced in response to the next P-wave sensing threshold crossing may be determined by control module 206 as a T-P interval. In other examples, a T-P interval may be determined from the unfiltered or alternate filtered EGM signal 265 or 267 when the T-wave is substantially filtered from the filtered EGM signal 266.

The T-P interval may be monitored beat-by-beat or on a less frequent basis to detect a shortening of the T-P interval. If the T-P interval is shortening, overlapping T-waves and P-waves may become indistinct from each other. A decrease in the T-P interval is detected at block 554. Detection of a shortened or decreased T-P interval may be based on comparing the T-P interval to a threshold interval or detecting a percentage change in the T-P interval compared to a previously measured or baseline T-P interval. In various examples, a single beat or running average T-P interval may be determined and if the single beat or running average T-P interval is decreasing in value for three or more successive determinations, a shortening T-P interval is detected at block 554. If the T-P interval shortens to a threshold interval or other criteria for detecting T-P interval shortening are met, the P-wave sensing criteria may be checked at block 560.

At block 556, control module 206 is configured to monitor an amplitude difference between sensed far-field P-waves and near-field T-waves. For example, a T-wave maximum peak amplitude may be determined during a signal analysis window after a cancel P-sense signal 274 is produced in response to the filtered EGM signal 266 crossing the T-wave sensing threshold as shown and described in conjunction with FIG. 5C. In other examples, the T-wave may be filtered from the filtered EGM signal 266 such that the T-wave is smaller than the P-wave. In this case, the T-wave maximum peak amplitude may be determined during the T-wave sensing window.

The P-wave maximum peak amplitude may be determined during a signal analysis window applied after the next P-sense signal 272 produced in response to the next crossing of the P-wave sensing threshold when another higher threshold crossing does not occur within time limit 310 (as shown in FIG. 5A). The difference between the T-wave amplitude and the P-wave amplitude may then be determined on a beat-by-beat or less frequent basis or as a running average amplitude difference.

A decreased amplitude difference is detected at block 558. The decreased amplitude difference may be due to a change in one or both of the P-wave amplitude and the T-wave amplitude. The decrease may be detected when the amplitude difference is less than a threshold difference or has decreased a predetermined percentage from a previously measured difference or baseline difference. In some examples a running average amplitude difference is compared to a baseline difference. The decrease may alternatively be detected at block 558 in response to a required number of consecutively determined differences being less than a preceding difference. In response to detecting a decreased amplitude difference, the P-wave sensing criteria are checked at block 560.

Checking P-wave sensing criteria may include performing the process of flow chart 400 (FIG. 8), performing the process of flow chart 500 (FIG. 9), or any portion or combination thereof. In some examples, the P-wave sensing criteria are checked at block 560 by adjusting the P-wave detector filter to increase the amplitude of one of the P-wave or T-wave, decrease the amplitude of one of the P-wave or T-wave, or cause a change in the filtered EGM signal morphology that results in an increase in the T-P interval. If filter adjustments do not provide increased P-wave and T-wave separation based on amplitude or time, the T-wave sensing window may be adjusted at block 560 to improve discrimination between the T-wave and the P-wave based on time. T-wave morphology of the filtered EGM signal 266 may be compared with or without filter adjustments to set new P-wave sensing criteria that provide reliable morphology discrimination for verifying P-waves during the AV interval.

Figure 10B:
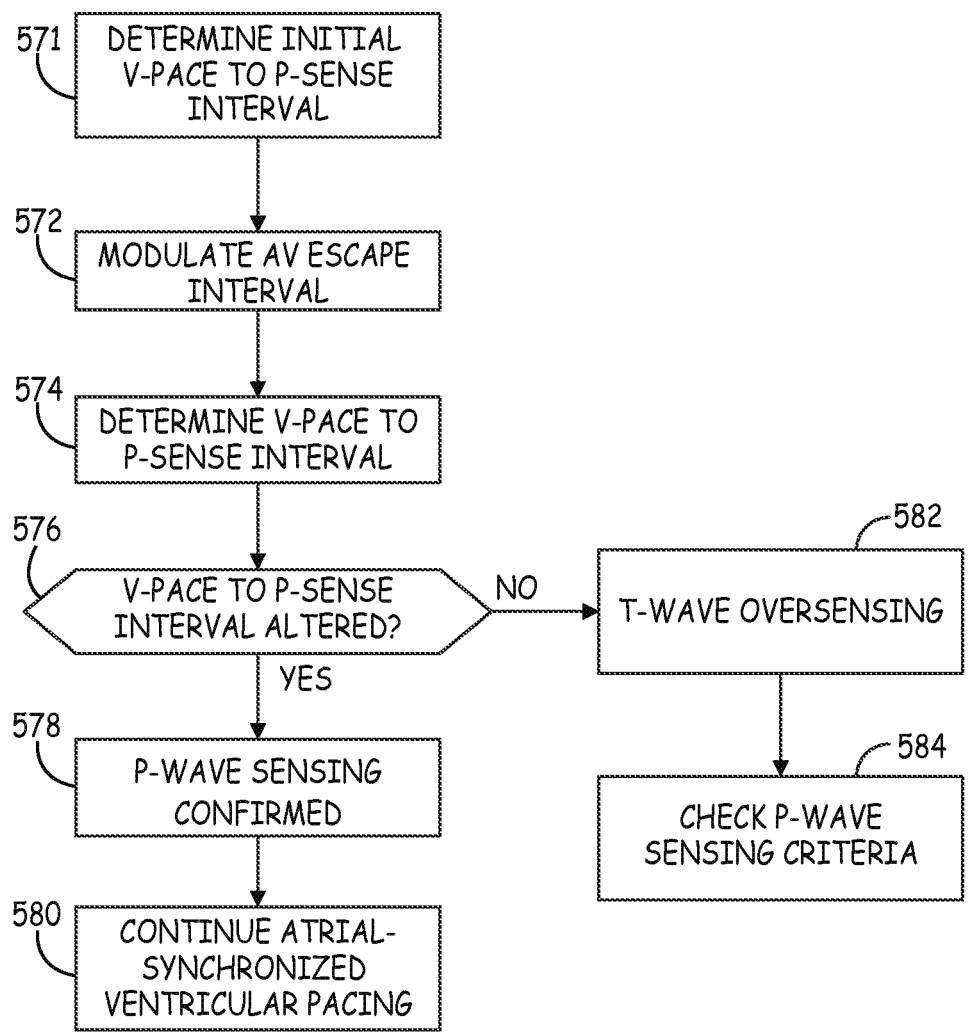
FIG. 10B is a flow chart of a method for determining a need for adjusting the P-wave sensing criteria according to another example.

FIG. 10B is a flow chart 570 of a method for determining a need for adjusting the P-wave sensing criteria according to another example. At block 571, if ventricular pacing is currently being delivered at the target AV pacing escape interval, the V-pace to P-sense interval is determined. The V-pace to P-sense interval is the time interval from a delivered ventricular pacing pulse to the next P-sense signal that is confirmed to be a P-wave during the AV pacing escape interval based on any additionally applied P-wave sensing criteria other than a P-wave sensing threshold crossing (as described above in conjunction with FIGS. 7A and 7B. If ventricular pacing is not currently being delivered when the process of flowchart 570 is started due to R-sense event signals occurring during the AV interval, a shortened test AV interval may be applied at block 571 to establish an initial V-pace to P-sense interval.

At block 572, the AV pacing escape interval is modulated from the target AV pacing escape interval. The AV pacing escape interval may be shorted in one step change, e.g., shortened by up to 100 ms, or modulated in two or more step changes to AV intervals that are shorter than the target AV interval to maintain ventricular pacing pulse delivery. The V-pace to P-sense interval is re-determined at block 574 for one or more altered AV intervals applied at block 572.

At block 576, the control module 206 determines if the V-pace to P-sense interval is altered in response to the modulated AV interval. If the V-pace to P-sense intervals match for two different AV pacing escape intervals, T-wave oversensing is suspected as determined at block 582. Control module 206 initiates a process to check and re-establish the P-wave sensing criteria at block 584, e.g., using the techniques described above in conjunction with FIG. 9. If the V-pace to P-sense interval does change with modulation of the AV interval, as determined at block 576, P-wave sensing is confirmed at block 578. Atrial-synchronized ventricular pacing continues at block 580 using the target AV interval and currently established P-wave sensing criteria.

Figure 11A:
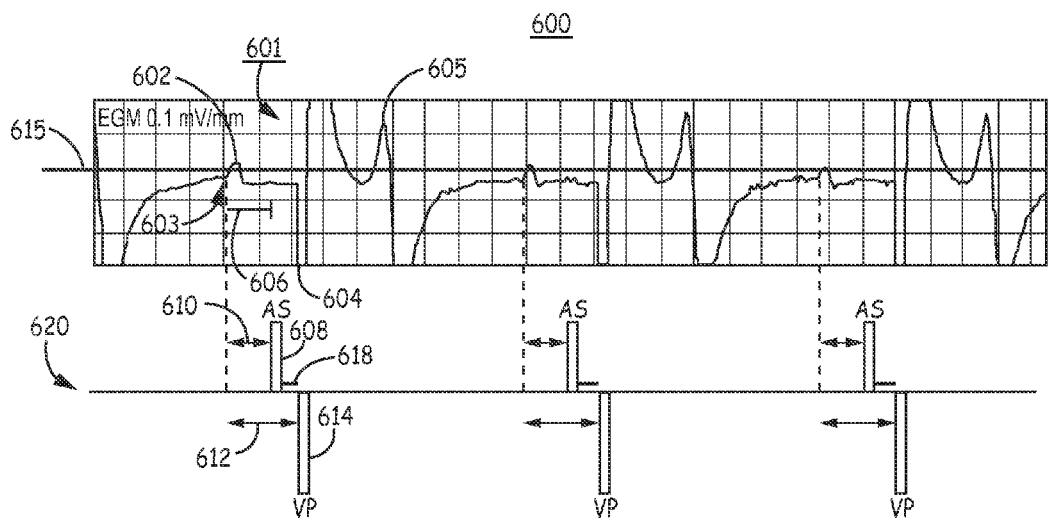
FIG. 11A is a diagram of a cardiac EGM signal and associated marker channel signals that may be produced by the RV pacemaker and transmitted to an external device according to one example.

FIG. 11A is a diagram 600 of a cardiac EGM signal 601 and associated marker channel signals 620 that may be produced by RV pacemaker 14 and transmitted to the external device 20 shown in FIG. 1 according to one example. FIG. 11B is a diagram 650 of the cardiac EGM signal 601 transmitted from the RV pacemaker 14 to the external device 20 and an associated marker channel display 640 that may be produced by a user display of external device 20.

Figure 11B:
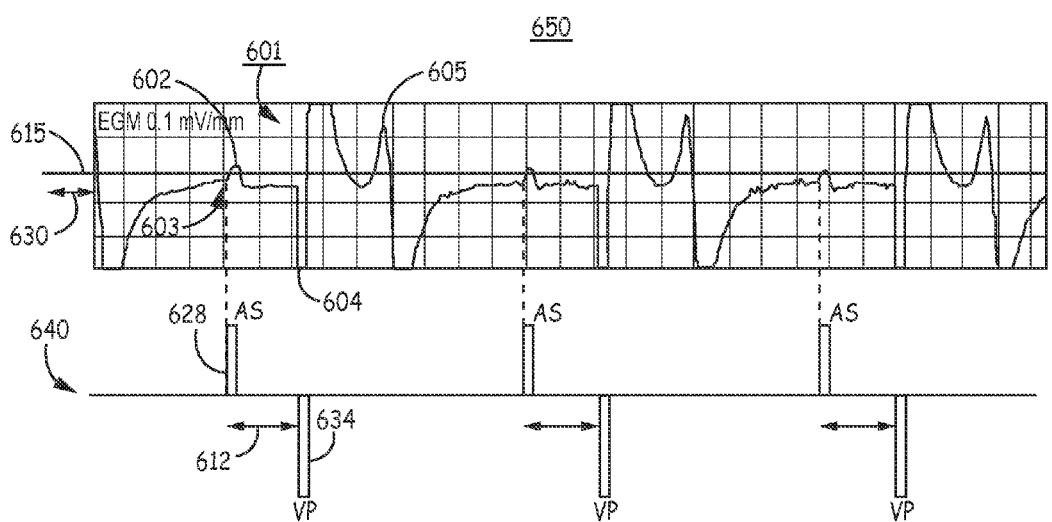
FIG. 11B is a conceptual diagram of a display of the cardiac EGM signal transmitted from the RV pacemaker to the external device and an associated marker channel that may be generated by a user display of the external device.

In FIGS. 11A and 11B, EGM signal 601 includes P-waves 602, ventricular pacing pulses 604 and T-waves 605. A P-wave sensing threshold 615 is indicated but may or may not be displayed graphically in a display produced by external device 20. In some examples, a numerical value of the P-wave sensing threshold may be displayed.

Since R-waves, T-waves 605, noise, and other signals may cross the P-wave sensing threshold 615, the RV pacemaker 14 confirms that a P-wave sensing threshold crossing 603 is a true P-wave 602 by comparing the EGM signal 601 to P-wave sensing criteria. As described above, the EGM signal 601 may be compared to a T-wave sensing threshold and/or an R-wave sensing threshold during a time limit as described in conjunction with FIGS. 5A-5C for use in controlling (maintaining, cancelling or adjusting) an AV pacing escape interval 612 that is started upon the P-wave sensing threshold crossing 603. Additionally or alternatively, the EGM signal 601 may be stored during an analysis window 606 and compared to P-wave sensing criteria to verify that the P-wave sensing threshold crossing is due to a true P-wave 602

Verification that the EGM signal 601 does not cross a T-wave sensing threshold and/or an R-wave sensing threshold during the time limit 310 (shown in FIGS. 5A-5C) and/or storing of the EGM signal waveform during an analysis window 606 and comparing the stored waveform to P-wave sensing criteria will require time after the P-wave sensing threshold crossing 603. Actual confirmation of the P-wave sensing threshold crossing as a true P-wave sensed event is, therefore, delayed in time by a delay time interval 610 after the P-wave sensing threshold crossing 603. The delay time interval 610 required to confirm a P-wave sensed event after the P-wave sensing threshold crossing 603 may be on the order of 20 ms to 120 ms, for example, but is within the AV pacing escape interval 612. The delay time interval 610 may equal the duration of an analysis window 606 or be longer than the analysis window 606.

After P-wave detector 262 verifies that the P-wave sensing threshold crossing 603 is due to a true P-wave 602, the RV pacemaker control module 206 may produce a marker channel P-wave sense event signal 608. The marker channel P-wave sense event (AS) signal 608 is produced after the time delay 610, upon confirming the P-wave sense event.

If the P-wave 602 is confirmed by additional signal analysis after the P-wave sensing threshold crossing 603, the AV pacing escape interval 612 started upon the P-wave sensing threshold crossing 603 is allowed to expire. A ventricular pacing pulse 604 is delivered upon expiration of the AV pacing escape interval 612. The RV pacemaker 14 may produce a marker channel ventricular pacing pulse (VP) signal 614 aligned in time with the ventricular pacing pulse 604.

If the external device 20 produces a display of EGM signal 601 and the AS and VP marker channel signals 608 and 614 in real time, the AS signal 608 appears to occur at the delay time interval 610 after the actual P-wave 602. The ventricular pacing pulse signal 614 appears to occur at a very short AV interval 618 after the AS signal 608 instead of at the actual AV pacing escape interval 612. The relative timing of marker channel signals 608 and 614 to each other and the EGM signal 601 as produced in real time may create user confusion if the EGM signal 601 and marker channel signals 612 and 614 appear in real time in a user display generated by external device 20.

In order to avoid user confusion, the control module 206 delays transmission of the EGM signal 601 by the pacemaker telemetry module 208 by a delay time 630 that is greater than or equal to the delay time interval 610 between P-wave sensing threshold crossing 603 and generation of the marker channel P-wave sense event signal 608. As shown in FIG. 10B, the user display of external device 20 produces a display of EGM signal 601 that is delayed from real time by delay time interval 630.

The marker channel 640 produced by the external device 20 may display the AS event marker 628 in real time when the marker channel P-wave sense event signal 608 is produced and transmitted from RV pacemaker 14. The VP marker 628, however, is displayed at the delay time 630 from the VP signal 614 produced by RV pacemaker 14. In this way, the P-wave sensing threshold crossing 603 and the start of the AV pacing escape interval 612 appear to be aligned with the P-wave sense event marker 628 even though the AS signal 608 is generated by RV pacemaker 14 later than the actual P-wave sensing threshold crossing 603. By delaying the VP marker 634 in real time from the pacing pulse signal 614 by delay time 630, the pacing pulse marker 634 is displayed at the expected AV pacing escape interval 612 after the AS event marker 628 and remains aligned with the pacing pulse 604 appearing on EGM signal 601, which has also been delayed by the same delay time 630. In this way, the markers 628 and 634 are properly aligned with corresponding events, i.e., P-wave 602 and pacing pulse 604, of the EGM signal 601 to enable straight-forward and logical analysis of the sensing and pacing operations of RV pacemaker 14.

Figure 12:
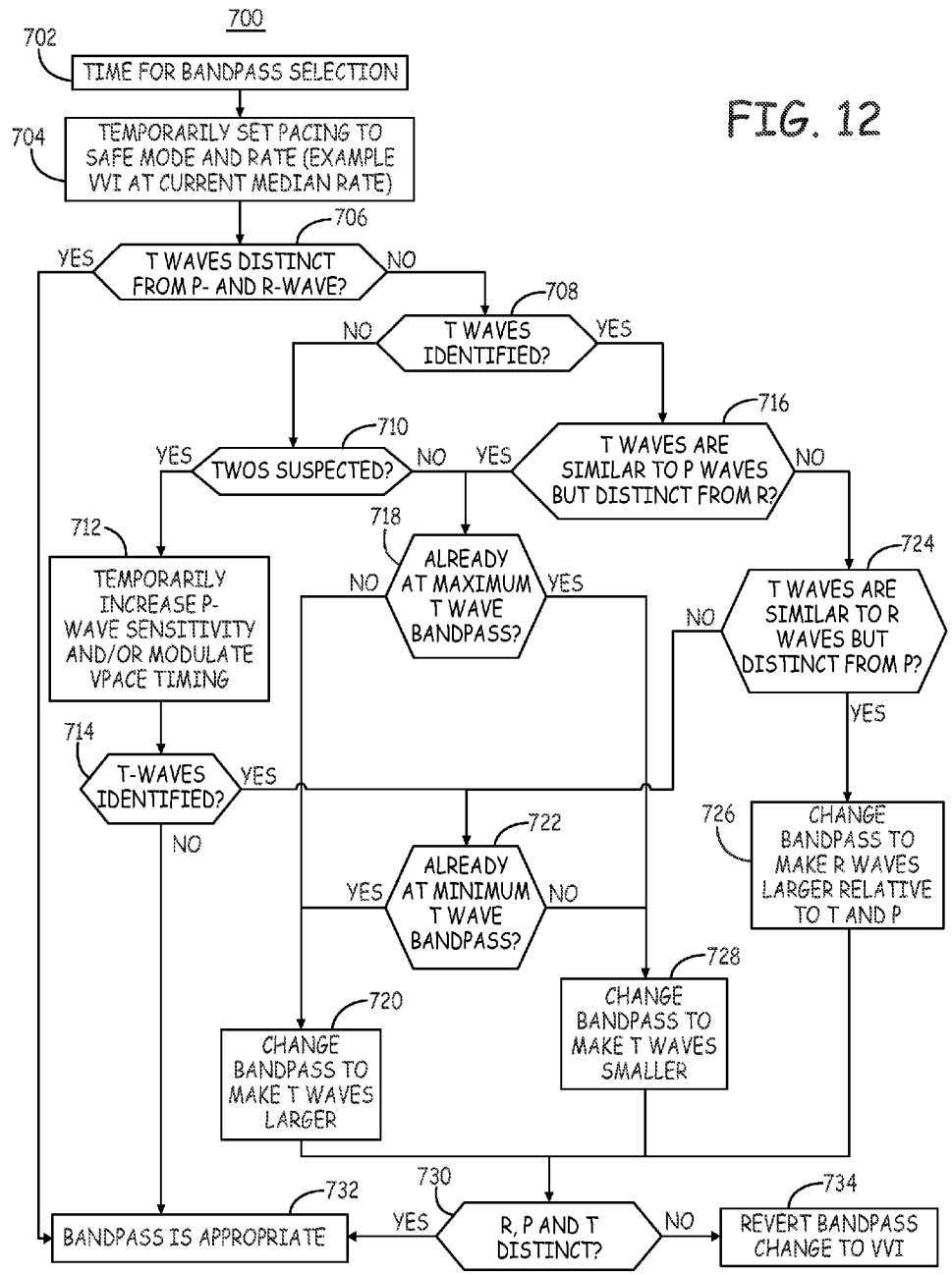
FIG. 12 is a flow chart of a method that may be performed by the RV pacemaker of FIG. 1 for automatically adjusting a P-wave detector filter according to another example.

FIG. 12 is a flow chart 700 of a method performed by RV pacemaker 14 for automatically adjusting the P-wave detector filter 264 according to another example. At block 702, the RV pacemaker control module 206 determines if it is time for selecting or adjusting the bandpass of P-wave detector filter 264. Bandpass selection may be performed according to the method of flow chart 700 on a periodic basis when the heart rhythm is verified to be a normal sinus rhythm, e.g., based on R-wave sense event signals 258 (FIG. 4A). Bandpass selection may additionally or alternatively be performed according to the method of flow chart 700 on a triggered basis. For example, the process shown by flow chart 700 may be entered from block 560 of FIG. 10A or block 584 of FIG. 10B.

At block 704, the control module 206 may control pulse generator 202 in a temporary safe pacing mode, e.g., a VVI pacing mode set at a nominal pacing rate or a rate based on a median or running average of RR intervals between R-wave sense event signals 258. During the process for searching for an optimal P-wave detector filter bandpass, ventricular pacing may be controlled by control module 206 such that pacing pulse delivery is unaffected by over or under sensing of cardiac events that may occur as the P-wave detector filter 264 is adjusted. In other words, pace timing module 270 may be temporarily configured to respond only to R-wave sense event signals 258 from R-wave detector 252 for controlling the timing of ventricular pacing pulses during the process of flow chart 700.

At block 706, the sensing module 204 of RV pacemaker 14 determines if T-waves are distinct from P-waves and R-waves in the filtered cardiac electrical signal 266 at the current filter bandwidth. T-waves are determined to be distinct from both P-waves and R-waves based on predetermined distinction criteria. For example, T-wave distinction criteria may require that the differences between a T-wave feature and the analogous P-wave and R-wave features are sufficiently large enough to confidently set sensing thresholds between these feature values that reliably distinguish P-waves, T-waves and R-waves in the filtered signal 266.

In some cases, T-waves may be identifiable from the filtered cardiac electrical signal 266 but may not meet criteria defined for determining that the T-waves are distinct. For example, T-waves may be identified from the filtered signal 266 based on timing following an R-wave sense event signal from R-wave detector 252, e.g., during a T-wave window. However, in the filtered signal 266, the difference between the T-wave peak amplitude and the P-wave peak amplitude may not meet T-wave distinction criteria. For example, T-wave and P-wave peak amplitudes may be required to have at least a 50% difference to determine that the identified T-wave is distinct from the P-wave. In another example, the T-wave and the P-wave may be identified following the R-wave but may be merged such that T-wave and the P-wave are not separated enough in time or amplitude to meet predetermined criteria for detecting the T-waves as being distinct.

The determination of whether the T-wave is distinct may be made at block 706, for example, based on a comparison of the maximum peak amplitudes of a P-wave, R-wave and T-wave each sensed using respective sensing thresholds according to the methods described in conjunction with FIGS. 5A through 5C. If the maximum peak amplitudes of each sensed event are a predetermined difference away from each other, e.g., at least 50% to 75% away from each other enabling distinct cardiac event sensing threshold amplitudes to be defined, the P-, T- and R-waves may be determined to be distinct at block 706. The relative time of a sensed P-wave and a sensed T-wave from a sensed R-wave may also be used to determine distinctness between the three cardiac events at block 706. In some cases, a T-wave is determined to be distinct from P-waves and R-waves at block 706 based on an absence of a T-wave within a T-wave window following the R-wave and a P-wave occurring outside the T-wave window. In this case, the T-wave may be effectively filtered from the filtered signal 266.

If the T-waves are distinct from P-waves and R-waves at block 706, the current bandpass of the P-wave detector filter 264 is determined to be appropriate at block 732. No adjustment of the filter bandpass is made. The sensing module 204 and control module 206 may exit the process of flow chart 700, and switch from the safe pacing mode set at block 704 to return to atrial-synchronized ventricular pacing using FF sensed P-waves. The pace timing and control module 270 may be re-enabled to respond to P-wave sense event signals 272.

If the T-waves are not distinct from P-waves and R-waves at block 706 according to predetermined criteria for classifying the T-waves as being distinct, the sensing module 204 determines if T-waves can be identified from the filtered cardiac signal 266 at block 708. If T-waves are not identified at block 708, e.g., if only R-waves and P-waves are detected at block 706, the sensing module 204 or the control module 206 may check for evidence of possible T-wave oversensing (TWOS) at block 710.

For example, if a fast ventricular rate is detected at block 710, based on a rate of R-wave sense event signals 258 produced by R-wave detector 252 or based on a rate of R-wave sensing threshold crossings determined by P-wave detector 262, T-wave oversensing may be occurring. In some cases, T-waves may be sensed as R-waves and correctly identified as T-waves due to the T-wave amplitude being indistinct from the R-wave amplitude. A fast rate of sensed R-waves may be evidence of TWOS. A fast rate of sensed R-waves may be detected based on RR intervals less than 400 ms, less than 300 ms, or less than a predefined tachycardia detection interval.

In other instances, T-waves may be oversensed as P-waves due to the timing and amplitude of T-waves and P-waves being indistinct based on currently established P-wave sensing criteria. In this case, the rhythm may be AS-VP-AS-VP occurring at a relatively fast rate, for example at a VP-AS interval of 400 ms. The AS events may be T-waves falsely sensed as P-waves and causing the pace timing and control module 270 to set AV pacing escape intervals in response to the false P-wave sense event signals. The T-waves falsely sensed as P-waves can lead to pacing the ventricle at a relatively fast rate. Accordingly the rhythm pattern of AS-VP-AS-VP at regular short intervals may be evidence of TWOS detected at block 710.

In order to determine if TWOS is occurring in response to determining that TWOS is suspected at block 710, the P-wave detector 262 temporarily increases the P-wave sensitivity and/or modulates the ventricular pacing pulse timing at block 712. P-wave sensitivity may be increased by lowering the P-wave sensing threshold. The ventricular pacing pulse timing may be modulated by adjusting the VV escape interval and/or adjusting the AV escape interval. If the AV escape interval is shortened, the next P-wave sense event is expected to be later after the R-wave, but a true T-wave after the R-wave is expected to move earlier with the earlier ventricular pacing pulse. If an atrial sense event occurs earlier upon shortening the AV escape interval, TWOS is detected. The earlier atrial sense event is identified as an oversensed T-wave at block 714. Bandpass filter adjustment is made at block 720 or 728 as described below to make the T-wave and P-wave distinct.

In another example, the AV escape interval may be lengthened, e.g., by 50 ms or more. The time interval between the ventricular pacing pulse and the atrial sense event is determined at the lengthened AV escape interval. If the time interval from the ventricular pacing pulse to the next atrial sense event stays the same, the atrial sense event is an oversensed T-wave. Bandpass filter adjustment is made at block 720 or 728 as described below to make the T-wave and P-wave distinct. If the interval shortens, the atrial sense event is a true atrial event; the ventricular pacing pulse has been moved later or closer to the next atrial event in time.

T-waves are identified at block 714 if modulation of the ventricular pacing pulse timing does not alter a V-pace to P-Sense interval (in which case the P-Sense is actually a T-wave). T-waves may also be identified if a lower P-wave sensing threshold results in more atrial sense events. True P-waves may be sensed at the increased sensitivity and true T-waves may be identified as being oversensed as P-waves when the sensitivity is lower (sensing threshold higher). If oversensed T-waves are identified, bandpass filter adjustment is made by advancing to block 722.

In other instances, T-waves may be sensed at a lower P-wave sensing threshold when the T-wave has a lower amplitude than the P-waves. If lowering the P-wave sensing threshold reveals low amplitude sensed events consistent with T-wave timing relative to R-wave sense events in addition to true P-wave sense events, T-waves are identified at block 714, and T-wave filtering is deemed appropriate at block 732.

If T-waves can still not be identified at block 714 at the modulated ventricular pacing pulse times and/or reduced P-wave sensing threshold, T-waves may be considered absent from the filtered signal 266. The P-wave detector filter bandpass is deemed appropriate at block 732. No adjustment of the bandpass is required, and atrial-synchronized ventricular pacing may be restored. Additionally or alternatively, T-waves may be identified at block 714 using a differential signal and/or an integrated signal as described above in conjunction with FIG. 7B.

If T-wave oversensing is not suspected based on the ventricular rate at block 710, or if T-waves are identified but are similar to P-waves in amplitude, timing and/or morphology as determined at block 716, the sensing module 204 determines at block 718 if the P-wave detector filter 264 has already been adjusted to maximize the T-wave. The process 700 performed by RV pacemaker 14 takes advantage of the expected bandpass frequencies that will increase the T-wave signal in the filtered cardiac electrical signal 266 in order to intentionally increase T-wave amplitude when the T-wave amplitude and/or morphology is similar to the P-wave.

If the filter has not been adjusted to maximize the T-wave signal, the bandpass of filter 264 is adjusted at block 720 to increase the T-wave signal strength. The bandpass may be adjusted, e.g., by lowering the center frequency and/or increasing or decreasing the bandwidth. If the new bandpass makes P-waves, T-waves and R-waves distinct, as determined at block 730, e.g., based on the criteria described above in conjunction with block 706, the adjusted bandpass is deemed appropriate at block 732. The T-wave may be intentionally increased in amplitude by adjusting the bandpass of P-wave detector filter 264 to provide greater separation of the P-wave and T-wave based on amplitude, time, and or morphology.

While not explicitly shown in FIG. 12, it is understood that the process may repeat the steps at block 718 and 720 to make multiple adjustments to the P-wave detector filter 264 until the T-wave signal is increased enough to make T-waves distinct from P-waves. If the filter has been adjusted to a bandpass that results in a maximum T-wave signal amplitude and/or width at block 718, but the T-waves are still not distinct from P-waves, the bandpass may be adjusted at block 728 to make the T-wave signals smaller in the filtered signal 266.

Similarly, if the T-waves are identified in the filtered signal at block 708, and are distinct from P-waves but are similar to the R-waves in amplitude as determined at block 724, the bandpass may be adjusted at block 728 to make the T-wave signal strength smaller. While not explicitly shown in FIG. 12, the steps at blocks 728 and 722 for adjusting the bandpass to decrease the T-wave signal strength in the filtered signal 266 until the T-wave cannot be made any smaller may be repeated multiple times until a bandpass that results in the minimized T-wave signal is identified.

At block 730, the sensing module 204 determines if the adjusted bandpass makes the R-wave, P-wave and T-wave distinct in the filtered signal by decreasing the T-wave signal, not necessarily to a minimum. If the P-wave, T-wave, and R-wave are now distinct, e.g., by making the T-wave amplitude smaller, the adjusted bandpass is deemed appropriate for enabling P-wave sensing and atrial-synchronized ventricular pacing at block 732. Sensing module 204 may be configured to determine if T-waves are distinct from P-waves and from R-waves within a maximum number of filter adjustments.

If T-waves can be identified from the filtered signal at block 708 but T-wave features are distinct from P-waves but not R-waves based on predetermined distinction criteria ("no" branch of block 724), the bandpass may be adjusted to increase the R-wave amplitude at block 726 to increase amplitude-based separation between T-waves and R-waves in some examples. In some cases, separation of R-waves and T-waves by P-wave detector 262 is not required if the separate R-wave detector 252 is reliably producing R-wave sense event signals 258. However, if all three events are being sensed from filtered signal 266 and used for controlling pacing escape interval, it may be desirable to increase the separation between T-waves and R-waves when these signals are indistinct. If separation between T-waves and R-waves is increased, T-waves and P-waves can be distinguished based on time and/or amplitude relative to a sensed R-wave.

If all adjusted bandpasses tested for either increasing or decreasing the T-wave signal strength or increasing the R-wave fail to make the P-wave, T-wave, and R-wave distinct based on at least time, amplitude and/or morphology, as determined at block 730, according to predetermined distinction criteria, the control module 206 may temporarily suspend atrial-synchronized ventricular pacing at block 734 by setting the pacing mode to a VVI mode. The bandpass of filter 264 may be reverted back to a previous setting until a future attempt at adjusting the bandpass filter is made again.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

For example, the following Items are illustrative of further embodiments:

Item 1. A method, comprising:
 producing a filtered cardiac electrical signal by filtering a raw cardiac electrical signal by an adjustable filter of a sensing module of a medical device configured to receive the raw cardiac electrical signal, the raw cardiac electrical signal comprising R-waves, T-waves and P-waves via electrodes coupled to the sensing module;
 determining if the T-waves are distinct from the P-waves in the filtered cardiac electrical signal;
 adjusting the filter to increase a difference between a feature of the P-waves and a feature of the T-waves in the filtered cardiac signal when the T-waves are not distinct from the P-waves;
 determining P-wave sensing criteria based on the difference;
 sensing a P-wave from the filtered cardiac electrical signal when the P-wave sensing criteria are met; and
 setting a ventricular pacing escape interval in response to sensing the P-wave.

Item 2. The method of item 1, wherein adjusting the filter to increase the difference comprises adjusting the filter to increase a difference between a peak P-wave amplitude and a peak T-wave amplitude in the filtered cardiac electrical signal.

Item 3. The method of any one of items 1-2, wherein adjusting the filter comprises adjusting the filter to increase the peak T-wave amplitude in the filtered cardiac signal.

Item 4. The method of any one of items 1-3, wherein determining the P-wave sensing criteria comprises determining a first threshold less than the maximum P-wave amplitude and a second threshold greater than the first threshold but less than the maximum T-wave amplitude, wherein sensing the P-wave from the filtered cardiac signal comprises sensing a crossing of the first sensing threshold by the filtered cardiac signal, setting a time limit, and not sensing a crossing of the second sensing threshold during the time limit.

Item 5. The method of any one of items 1-4, wherein adjusting the filter comprises adjusting at least one of a center frequency and a bandpass width.

Item 6. The method of any one of items 1-5, further comprising:
determining a plurality of T-P intervals between consecutive pairs of T-waves and P-waves in the filtered cardiac electrical signal;
detecting a decreasing trend in the plurality of T-P intervals; and
adjusting at least one of the filter and a T-wave sensing window in response to detecting the decreasing trend; and
sensing P-waves from the filtered cardiac signal when the P-wave sensing criteria are met outside the T-wave sensing window.

Item 7. The method of any one of items 1-6, further comprising:
detecting a decrease in a difference between a P-wave feature and T-wave feature in the filtered cardiac electrical signal; and
adjusting the filter in response to detecting the decrease.

Item 8. The method of any one of items 1-7, further comprising:
repeating the adjusting of the filter and the determining if the T-waves are distinct from the P-waves in the filtered cardiac electrical signal;
determining if the P-waves and the T-waves of the filtered cardiac electrical signal are distinct based on at least one of time, peak amplitude and morphology within a maximum number of filter adjustments; and
disabling setting the ventricular pacing escape interval when the P-waves and the T-waves of the filtered cardiac electrical signal are not distinct based on at least one of time, peak amplitude and morphology within the maximum number of filter adjustments.

Item 9. The method of any one of items 1-8, further comprising:
periodically adjusting at least one of the filter and a T-wave sensing window;
re-determining if the P-waves and the T-waves are distinct based on at least one of time, peak amplitude and morphology; and
re-determining the P-wave sensing criteria when the P-waves and the T-waves in the filtered cardiac electrical signal are distinct after a periodic adjustment of at least one of the filter and the T-wave sensing window; and
re-enabling setting the ventricular pacing escape interval in response to P-waves sensed by the sensing module when the P-waves and the T-waves are distinct after a periodic adjustment of at least one of the filter and the T-wave sensing window.

Item 10. The method of any one of items 1-9, further comprising:
determining if oversensing of the T-waves by the sensing module is suspected;
lowering a P-wave sensing control parameter to increase a sensitivity of the sensing module for sensing P-waves when T-wave oversensing is suspected;
determining if T-waves can be identified from the filtered cardiac electrical signal after lowering the P-wave sensing control parameter; and
withholding the adjusting of the filter in response to determining that T-waves cannot be identified from the filtered cardiac electrical signal after lowering the P-wave sensing control parameter.

Item 11. An implantable medical device, comprising:
a sensing module comprising an adjustable filter and configured to:
receive a raw cardiac electrical signal comprising R-waves, T-waves and P-waves via electrodes coupled to the sensing module;
filter the raw cardiac electrical signal by the adjustable filter to produce a filtered cardiac electrical signal;
determine if the T-waves are distinct from the P-waves in the filtered cardiac electrical signal;
adjust the filter to increase a difference between a feature of the P-waves and a feature of the T-waves in the filtered cardiac signal when the T-waves are not distinct from the P-waves;
determine P-wave sensing criteria based on the difference; and
sense a P-wave from the filtered cardiac electrical signal when the P-wave sensing criteria are met;
a pulse generator configured to generate and deliver a ventricular pacing pulse via electrodes coupled to the pulse generator; and
a control module coupled to the sensing module and the pulse generator and configured to set a ventricular pacing escape interval in response to the sensing module sensing the P-wave to control the pulse generator to deliver a ventricular pacing pulse when the ventricular pacing escape interval expires.

Item 12. The device of item 11, wherein the sensing module is configured to adjust the filter to increase the difference by adjusting the filter to increase a difference between a peak P-wave amplitude and a peak T-wave amplitude in the filtered cardiac electrical signal.

Item 13. The device of any one of items 11-12, wherein the sensing module is configured to adjust the filter to increase the difference by adjusting the filter to increase the peak T-wave amplitude in the filtered cardiac signal.

Item 14. The device of any one of items 11-13, wherein the sensing module is configured to:
determine the P-wave sensing criteria by at least determining a first threshold less than the maximum P-wave amplitude and a second threshold greater than the first threshold but less than the maximum T-wave amplitude, and
sense the P-wave from the filtered cardiac signal by at least sensing a crossing of the first sensing threshold by the filtered cardiac signal, setting a time limit, and not sensing a crossing of the second sensing threshold during the time limit.

Item 15. The device of any one of items 11-14, wherein the sensing module is configured to adjust the filter by adjusting at least one of a center frequency and a bandpass width.

Item 16. The device of any one of items 11-15, wherein:
the control module is further configured to:
determine a plurality of T-P intervals between consecutive pairs of T-waves and P-waves in the filtered cardiac electrical signal; and
detect a decreasing trend in the plurality of T-P intervals;
the sensing module is further configured to
adjust at least one of the filter and a T-wave sensing window when the control module detects the decreasing trend; and sense P-waves from the filtered cardiac signal when the P-wave sensing criteria are met outside the T-wave sensing window.

Item 17. The device of any one of items 11-16, wherein:
the control module is further configured to detect a decrease in a difference between a P-wave feature and T-wave feature in the filtered cardiac electrical signal; and
the sensing module is further configured to adjust the filter when the control module detects the decrease.

Item 18. The device of any one of items 11-17, wherein the sensing module is further configured to:
repeat the adjusting of the filter and the determining if the T-waves are distinct from the P-waves in the filtered cardiac electrical signal;
determine if the P-waves and the T-waves of the filtered cardiac electrical signal are distinct based on at least one of time, peak amplitude and morphology within a maximum number of filter adjustments; and
the control module is configured to disable setting the ventricular pacing escape interval when the sensing module determines that the P-waves and the T-waves of the filtered cardiac electrical signal are not distinct based on at least one of time, peak amplitude and morphology within the maximum number of filter adjustments.

Item 19. The device of any one of items 11-18, wherein:
the sensing module is further configured to:
periodically adjust at least one of the filter and a T-wave sensing window;
re-determine if the P-waves and the T-waves are distinct based on at least one of time, peak amplitude and morphology; and
re-determine the P-wave sensing criteria when the P-waves and the T-waves in the filtered cardiac electrical signal are distinct after a periodic adjustment of at least one of the filter and the T-wave sensing window; and
the control module is further configured to re-enable setting the ventricular pacing escape interval in response to P-waves sensed by the sensing module when the sensing module determines that the P-waves and the T-waves are distinct after a periodic adjustment of at least one of the filter and the T-wave sensing window.

Item 20. The device of any one of items 11-19, wherein:
the control module is further configured to determine if oversensing of the T-waves by
the sensing module is suspected; and
the sensing module is further configured to:
lower a P-wave sensing control parameter to increase a sensitivity of the sensing module for sensing P-waves when the control module determines that T-wave oversensing is suspected;
determine if T-waves can be identified from the filtered cardiac electrical signal after lowering the P-wave sensing control parameter; and
withhold the adjusting of the filter in response to determining that T-waves cannot be identified from the filtered cardiac electrical signal after lowering the P-wave sensing control parameter.

Item 21. The device of any one of items 11-20, further comprising:
a housing enclosing the sensing module, the pulse generator and the control module;
at least one electrode carried by the housing and coupled to the sensing module for receiving the raw cardiac electrical signal and coupled to the pulse generator for delivering the ventricular pacing pulse.

Item 22. A non-transitory, computer-readable medium storing a set of instructions which, when executed by an implantable medical device cause the device to:
produce a filtered cardiac electrical signal by filtering a raw cardiac electrical signal by an adjustable filter of a sensing module of the medical device configured to receive the raw cardiac electrical signal, the raw cardiac electrical signal comprising R-waves, T-waves and P-waves via electrodes coupled to the sensing module;
determine if the T-waves are distinct from the P-waves in the filtered cardiac electrical signal;
adjust the filter to increase a difference between a feature of the P-waves and a feature of the T-waves in the filtered cardiac signal when the T-waves are not distinct from the P-waves;
determine P-wave sensing criteria based on the difference;
sense a P-wave from the filtered cardiac electrical signal when the P-wave sensing criteria are met; and
set a ventricular pacing escape interval in response to sensing the P-wave.

Thus, various examples of an implantable medical device including a sensing extension having a flotation member have been described. It is recognized that various modifications may be made to the described embodiments without departing from the scope of the following claims.

The invention claimed is:

1. A method for use in an implanted medical device, the method comprising:
producing a filtered cardiac electrical signal using an adjustable filter within a sensing module by filtering a raw cardiac electrical signal received from implanted electrodes operably connected to the sensing module, the raw cardiac electrical signal comprising R-waves, T-waves and P-waves via electrodes coupled to the sensing module;
determining if the T-waves are distinct from the P-waves in the filtered cardiac electrical signal;
adjusting the filter to increase a difference between a feature of the P-waves and a feature of the T-waves in the filtered cardiac signal when the T-waves are not distinct from the P-waves;
determining P-wave sensing criteria based on the difference;
sensing a P-wave from the filtered cardiac electrical signal when the P-wave sensing criteria are met; and
setting a ventricular pacing escape interval in response to sensing the P-wave.

2. The method of claim 1, wherein adjusting the filter to increase the difference comprises adjusting the filter to increase a difference between a peak P-wave amplitude and a peak T-wave amplitude in the filtered cardiac electrical signal.

3. The method of claim 2, wherein adjusting the filter comprises adjusting the filter to increase the peak T-wave amplitude in the filtered cardiac signal.

4. The method of claim 3, wherein determining the P-wave sensing criteria comprises determining a first threshold less than the maximum P-wave amplitude and a second threshold greater than the first threshold but less than the maximum T-wave amplitude,
wherein sensing the P-wave from the filtered cardiac signal comprises sensing a crossing of the first sensing threshold by the filtered cardiac signal, setting a time limit, and not sensing a crossing of the second sensing threshold during the time limit.

5. The method of claim 1, wherein adjusting the filter comprises adjusting at least one of a center frequency and a bandpass width.

6. The method of claim 1, further comprising:
determining a plurality of T-P intervals between consecutive pairs of T-waves and P-waves in the filtered cardiac electrical signal;
detecting a decreasing trend in the plurality of T-P intervals; and
adjusting at least one of the filter and a T-wave sensing window in response to detecting the decreasing trend; and
sensing P-waves from the filtered cardiac signal when the P-wave sensing criteria are met outside the T-wave sensing window.

7. The method of claim 1, further comprising:
detecting a decrease in a difference between a P-wave feature and T-wave feature in the filtered cardiac electrical signal; and
adjusting the filter in response to detecting the decrease.

8. The method of claim 1, further comprising:
repeating the adjusting of the filter and the determining if the T-waves are distinct from the P-waves in the filtered cardiac electrical signal;
determining if the P-waves and the T-waves of the filtered cardiac electrical signal are distinct based on at least one of time, peak amplitude and morphology within a maximum number of filter adjustments; and
disabling setting the ventricular pacing escape interval when the P-waves and the T-waves of the filtered cardiac electrical signal are not distinct based on at least one of time, peak amplitude and morphology within the maximum number of filter adjustments.

9. The method of claim 8, further comprising:
periodically adjusting at least one of the filter and a T-wave sensing window;
re-determining if the P-waves and the T-waves are distinct based on at least one of time, peak amplitude and morphology; and
re-determining the P-wave sensing criteria when the P-waves and the T-waves in the filtered cardiac electrical signal are distinct after a periodic adjustment of at least one of the filter and the T-wave sensing window; and
re-enabling setting the ventricular pacing escape interval in response to P-waves sensed by the sensing module when the P-waves and the T-waves are distinct after a periodic adjustment of at least one of the filter and the T-wave sensing window.

10. The method of claim 1, further comprising:
determining if oversensing of the T-waves by the sensing module is suspected;
lowering a P-wave sensing control parameter to increase a sensitivity of the sensing module for sensing P-waves when T-wave oversensing is suspected;
determining if T-waves can be identified from the filtered cardiac electrical signal after lowering the P-wave sensing control parameter; and
withholding the adjusting of the filter in response to determining that T-waves cannot be identified from the filtered cardiac electrical signal after lowering the P-wave sensing control parameter.

11. An implantable medical device, comprising:
a sensing module comprising an adjustable filter and configured to:
receive a raw cardiac electrical signal comprising R-waves, T-waves and P-waves via electrodes coupled to the sensing module;
filter the raw cardiac electrical signal by the adjustable filter to produce a filtered cardiac electrical signal;
determine if the T-waves are distinct from the P-waves in the filtered cardiac electrical signal;
adjust the filter to increase a difference between a feature of the P-waves and a feature of the T-waves in the filtered cardiac signal when the T-waves are not distinct from the P-waves;
determine P-wave sensing criteria based on the difference; and
sense a P-wave from the filtered cardiac electrical signal when the P-wave sensing criteria are met;
a pulse generator configured to generate and deliver a ventricular pacing pulse via electrodes coupled to the pulse generator; and
a control module coupled to the sensing module and the pulse generator and configured to set a ventricular pacing escape interval in response to the sensing module sensing the P-wave to control the pulse generator to deliver a ventricular pacing pulse when the ventricular pacing escape interval expires.

12. The device of claim 11, wherein the sensing module is configured to adjust the filter to increase the difference by adjusting the filter to increase a difference between a peak P-wave amplitude and a peak T-wave amplitude in the filtered cardiac electrical signal.

13. The device of claim 12, wherein the sensing module is configured to adjust the filter to increase the difference by adjusting the filter to increase the peak T-wave amplitude in the filtered cardiac signal.

14. The device of claim 13, wherein the sensing module is configured to:
determine the P-wave sensing criteria by at least determining a first threshold less than the maximum P-wave amplitude and a second threshold greater than the first threshold but less than the maximum T-wave amplitude, and
sense the P-wave from the filtered cardiac signal by at least sensing a crossing of the first sensing threshold by the filtered cardiac signal, setting a time limit, and not sensing a crossing of the second sensing threshold during the time limit.

15. The device of claim 11, wherein the sensing module is configured to adjust the filter by adjusting at least one of a center frequency and a bandpass width.

16. The device of claim 11, wherein:
the control module is further configured to:
determine a plurality of T-P intervals between consecutive pairs of T-waves and P-waves in the filtered cardiac electrical signal; and
detect a decreasing trend in the plurality of T-P intervals;
the sensing module is further configured to
adjust at least one of the filter and a T-wave sensing window when the control module detects the decreasing trend; and
sense P-waves from the filtered cardiac signal when the P-wave sensing criteria are met outside the T-wave sensing window.

17. The device of claim 11, wherein:
the control module is further configured to detect a decrease in a difference between a P-wave feature and T-wave feature in the filtered cardiac electrical signal; and
the sensing module is further configured to adjust the filter when the control module detects the decrease.

18. The device of claim 11, wherein the sensing module is further configured to:
repeat the adjusting of the filter and the determining if the T-waves are distinct from the P-waves in the filtered cardiac electrical signal;
determine if the P-waves and the T-waves of the filtered cardiac electrical signal are distinct based on at least one of time, peak amplitude and morphology within a maximum number of filter adjustments; and
the control module is configured to disable setting the ventricular pacing escape interval when the sensing module determines that the P-waves and the T-waves of the filtered cardiac electrical signal are not distinct based on at least one of time, peak amplitude and morphology within the maximum number of filter adjustments.

19. The device of claim 18, wherein:
the sensing module is further configured to:
periodically adjust at least one of the filter and a T-wave sensing window;
re-determine if the P-waves and the T-waves are distinct based on at least one of time, peak amplitude and morphology; and
re-determine the P-wave sensing criteria when the P-waves and the T-waves in the filtered cardiac electrical signal are distinct after a periodic adjustment of at least one of the filter and the T-wave sensing window; and
the control module is further configured to re-enable setting the ventricular pacing escape interval in response to P-waves sensed by the sensing module when the sensing module determines that the P-waves and the T-waves are distinct after a periodic adjustment of at least one of the filter and the T-wave sensing window.

20. The device of claim 11, wherein:
the control module is further configured to determine if oversensing of the T-waves by the sensing module is suspected; and
the sensing module is further configured to:
lower a P-wave sensing control parameter to increase a sensitivity of the sensing module for sensing P-waves when the control module determines that T-wave oversensing is suspected;
determine if T-waves can be identified from the filtered cardiac electrical signal after lowering the P-wave sensing control parameter; and
withhold the adjusting of the filter in response to determining that T-waves cannot be identified from the filtered cardiac electrical signal after lowering the P-wave sensing control parameter.

21. The device of claim 11, further comprising:
a housing enclosing the sensing module, the pulse generator and the control module;
at least one electrode carried by the housing and coupled to the sensing module for receiving the raw cardiac electrical signal and coupled to the pulse generator for delivering the ventricular pacing pulse.

22. A non-transitory, computer-readable medium storing a set of instructions which, when executed by an implantable medical device cause the device to:
produce a filtered cardiac electrical signal by filtering a raw cardiac electrical signal by an adjustable filter of a sensing module of the medical device configured to receive the raw cardiac electrical signal, the raw cardiac electrical signal comprising R-waves, T-waves and P-waves via electrodes coupled to the sensing module;
determine if the T-waves are distinct from the P-waves in the filtered cardiac electrical signal;
adjust the filter to increase a difference between a feature of the P-waves and a feature of the T-waves in the filtered cardiac signal when the T-waves are not distinct from the P-waves;
determine P-wave sensing criteria based on the difference;
sense a P-wave from the filtered cardiac electrical signal when the P-wave sensing criteria are met; and
set a ventricular pacing escape interval in response to sensing the P-wave.

* * * * *